(12) United States Patent
Connolly et al.

(10) Patent No.: US 11,236,382 B2
(45) Date of Patent: *Feb. 1, 2022

(54) METHOD AND SYSTEM FOR SAMPLE PREPARATION

(71) Applicant: Integrated Nano-Technologies, Inc., Henrietta, NY (US)

(72) Inventors: Dennis M. Connolly, Rochester, NY (US); Tara Holz, Henrietta, NY (US); Vera Tannous, Penfield, NY (US); Christopher Kilcoin, Boulder Creek, CA (US); Konstantin Aptekarev, Santa Cruz, CA (US); David B. Bailey, Webster, NY (US); Richard S. Murante, Henrietta, NY (US); Nathaniel E. Wescott, West Henrietta, NY (US)

(73) Assignee: Integrated Nano-Technologies, LLC, Henrietta, NY (US)

( * ) Notice: Subject to any disclaimer, the term of this patent is extended or adjusted under 35 U.S.C. 154(b) by 282 days.

This patent is subject to a terminal disclaimer.

(21) Appl. No.: 16/457,602

(22) Filed: Jun. 28, 2019

(65) Prior Publication Data

US 2019/0338346 A1 Nov. 7, 2019

Related U.S. Application Data

(60) Division of application No. 15/586,841, filed on May 4, 2017, now Pat. No. 10,378,045, which is a (Continued)

(51) Int. Cl.
*C12Q 1/6825* (2018.01)
*C12Q 1/6806* (2018.01)
(Continued)

(52) U.S. Cl.
CPC ............ *C12Q 1/6825* (2013.01); *B01L 3/502* (2013.01); *C12M 47/06* (2013.01); *C12N 1/066* (2013.01);
(Continued)

(58) Field of Classification Search
CPC ......... B01L 2200/026; B01L 2200/148; B01L 3/5023; G01N 33/49
See application file for complete search history.

(56) References Cited

U.S. PATENT DOCUMENTS

| 4,068,528 A | 1/1978 | Gundelfinger |
| 5,105,851 A * | 4/1992 | Fogelman ............. F16K 11/083 137/625.11 |

(Continued)

FOREIGN PATENT DOCUMENTS

| DE | 3712625 A1 | 11/1988 |
| EP | 2909346 B1 | 2/2019 |

(Continued)

OTHER PUBLICATIONS

Canadian Patent Office, Examiner's Report issued in CA Patent Application No. 2,888,316, dated Aug. 28, 2019 (4 pages).
(Continued)

*Primary Examiner* — Sally A Merkling
(74) *Attorney, Agent, or Firm* — Barclay Damon LLP

(57) ABSTRACT

A method for preparing a sample by utilizing a shearing force in the presence of a size stabilizer to break apart the sample to obtain nucleic acid molecules in a usable size range. Once nucleic acid molecules are obtained, magnetic nanoparticles are used to concentrate and clean the nucleic acid molecules for further testing.

20 Claims, 51 Drawing Sheets

Related U.S. Application Data continuation of application No. 15/157,584, filed on May 18, 2016, now Pat. No. 9,644,200, which is a continuation of application No. 14/056,603, filed on Oct. 17, 2013, now Pat. No. 9,347,086, which is a continuation-in-part of application No. 12/785,864, filed on May 24, 2010, now Pat. No. 8,663,918, which is a continuation-in-part of application No. 12/754,205, filed on Apr. 5, 2010, now Pat. No. 8,716,006.

(60) Provisional application No. 61/715,003, filed on Oct. 17, 2012, provisional application No. 61/180,494, filed on May 22, 2009, provisional application No. 61/166,519, filed on Apr. 3, 2009.

(51) Int. Cl.

| | | |
|---|---|---|
| *C12M 1/00* | (2006.01) | |
| *C12N 1/06* | (2006.01) | |
| *B01L 3/00* | (2006.01) | |
| *C12N 15/10* | (2006.01) | |
| *C12Q 1/02* | (2006.01) | |
| *G01N 1/28* | (2006.01) | |

(52) U.S. Cl.
CPC ......... *C12N 15/10* (2013.01); *C12N 15/1013* (2013.01); *C12Q 1/02* (2013.01); *C12Q 1/6806* (2013.01); *G01N 1/286* (2013.01); *B01L 2200/0631* (2013.01); *B01L 2300/0681* (2013.01); *C12Q 2531/113* (2013.01); *C12Q 2563/107* (2013.01); *C12Q 2563/143* (2013.01); *C12Q 2565/629* (2013.01); *G01N 2001/2866* (2013.01)

(56) References Cited

U.S. PATENT DOCUMENTS

| | | |
|---|---|---|
| 5,133,385 A | 7/1992 | Kawakami |
| 5,524,496 A | 6/1996 | Nagai et al. |
| 6,245,233 B1 | 6/2001 | Lu |
| 6,374,684 B1 * | 4/2002 | Dority ............ B01L 3/502 |
| | | 73/864.81 |
| 8,716,006 B2 | 5/2014 | Kilcoin |
| 9,347,086 B2 | 5/2016 | Connolly et al. |
| 9,644,200 B2 | 5/2017 | Connolly et al. |
| 10,378,045 B2 | 8/2019 | Connolly et al. |
| 2004/0157343 A1 | 8/2004 | Sandell |

FOREIGN PATENT DOCUMENTS

| | | |
|---|---|---|
| GB | 701963 A | 1/1954 |
| JP | 2000-500331 | 1/2000 |
| JP | 2007-136322 | 2/2008 |
| JP | 2009-148232 | 9/2010 |
| JP | 2010-139491 | 1/2012 |
| JP | 2012/522996 A | 9/2012 |
| WO | WO 2000/060125 | 10/2000 |
| WO | 2010/115192 A2 | 10/2010 |
| WO | WO2001/019428 A2 | 2/2011 |
| WO | 2014/062926 A1 | 4/2014 |

OTHER PUBLICATIONS

Japanese Office Action for JP 2018-116968; dated Jun. 4, 2019; 9 pages.
AU Patent Application 2010232396; Filed Oct. 3, 2011; Integrated Nano-Technologies, Inc.; Examination Report dated Jun. 29, 2018 (3 pages).
JP Patent Application Kokai S63-502454; Filed Jan. 15, 1987; Colter Electronics, Inc.; cover page only.
JP Patent Application Kokai 2002-540803; Filed Apr. 7, 2000; Dennis Michael Connolly; cover page only.
JP Patent Application No. 2015-537824; Filed Oct. 17, 2013; English translation of Office Action dated Feb. 7, 2018; 8 pages.
European Patent Office, Office Action from EP Patent Application No. 13847418.4 dated Jan. 11, 2018 (7 pages).
European Patent Office, Office Action issued in EP Patent Application No. 13847418.4-1404, dated Apr. 4, 2017 (6 pages).
Japanese Patent Office, Office Action issued in JP Patent Application 2015-537824; dated Aug. 8, 2017; 10 pages.
European Patent Office, Extended European Search Report from EP Application No. 10759538.1; dated Aug. 21, 2017; 7 pages.

* cited by examiner

Rectangular Configuration

Rectangular

Approimately 89% yeild

Lysis of spores using ultrasonic bead beating with size stabilizer

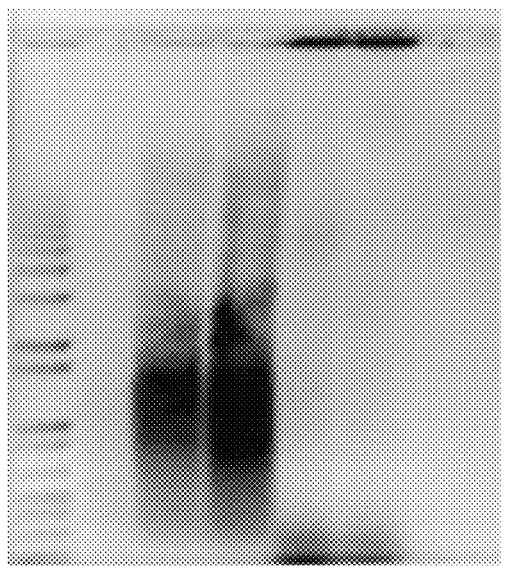

Lane 1: DNA ladder
Lane 2: empty
Lane 3 and 4: Fruit fly extract using a size stabilizer
Lanes 5 and 6: Fruit fly extract using traditional buffer Nucleic acid molecules isolated from fruit flies ultrasonic bead

FIG.34

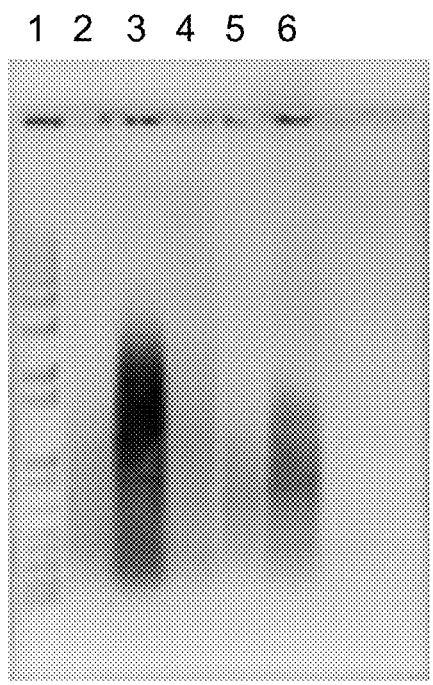

1. 1Kb Plus Ladder
2. B. subtilis genomic DNA. 1 µg
3. E. coli cells
4. B. subtilis spores
5. M13KE Phage
6. Drosophila metanogaster, 3 flies 2 min. sonication, Power Level 2

Universal sample processing

FIG.35

1 Minced ear notch
2 Supernatant from minced ear notch
3 Whole ear notch
4 Minced ear notch Nucleic Acid Isolation from Cattle Ear Tissue Sample Prep of flies with soil

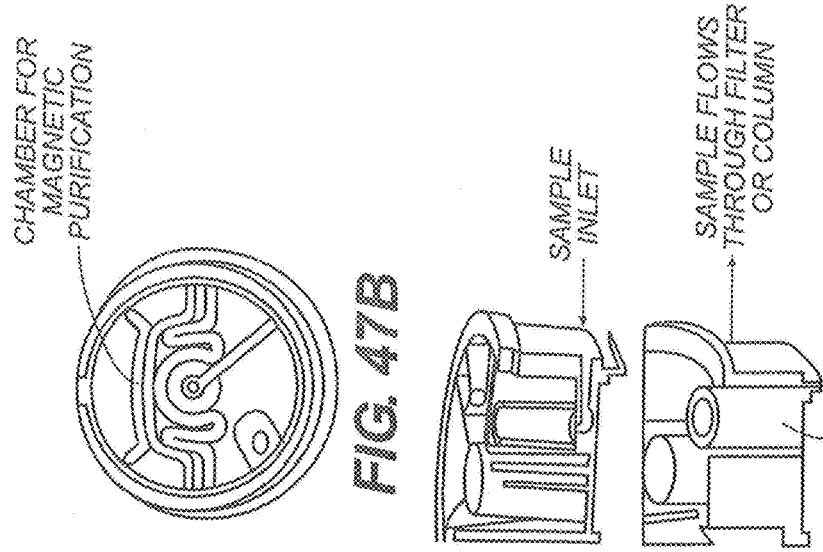
FIG. 47B
FIG. 47C
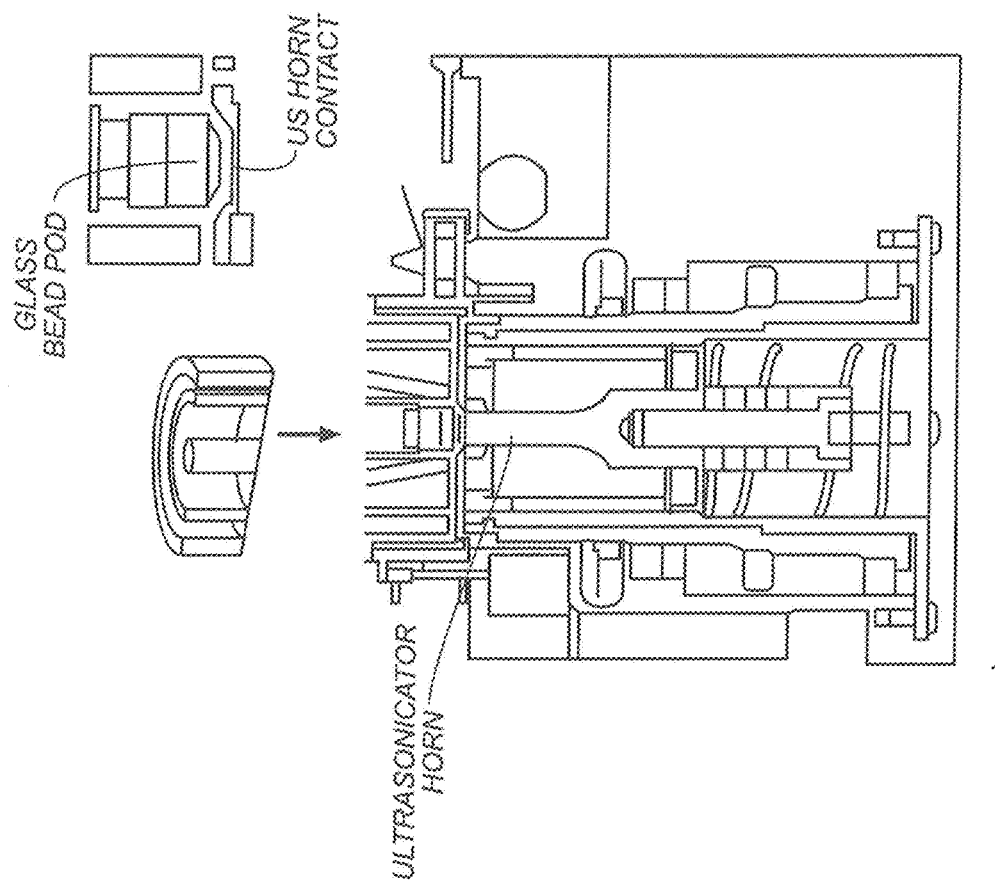
FIG. 47A

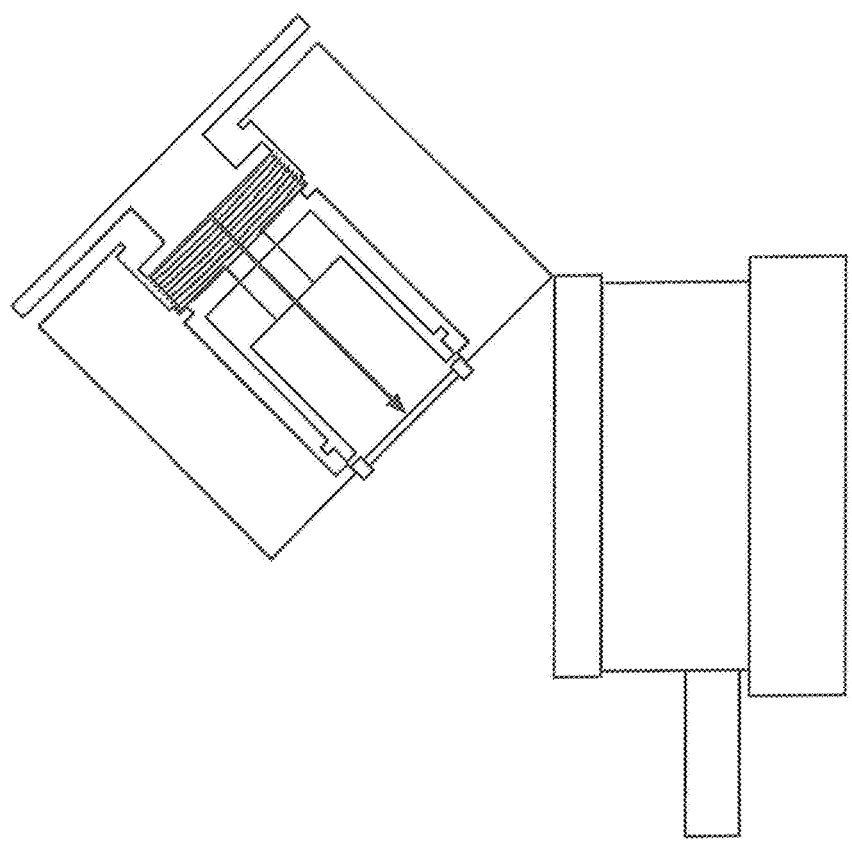
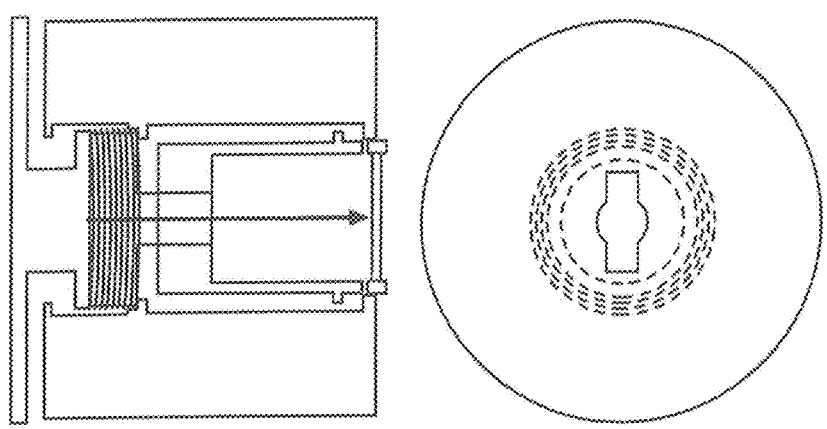
FIG. 53

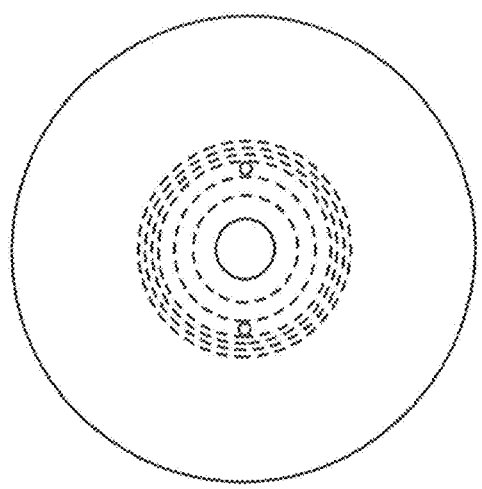
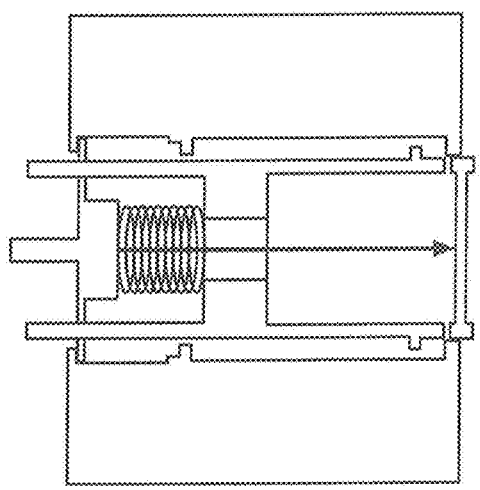
FIG. 54

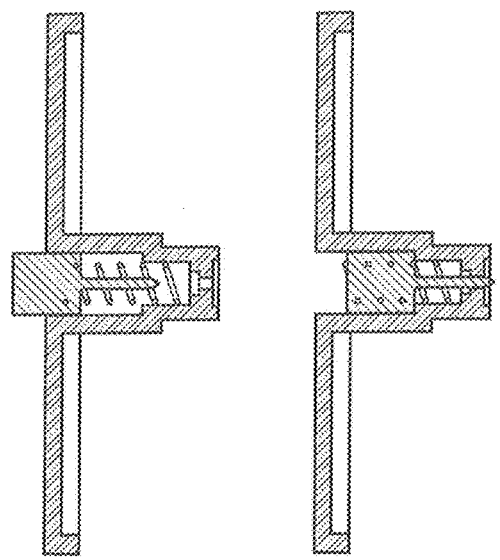
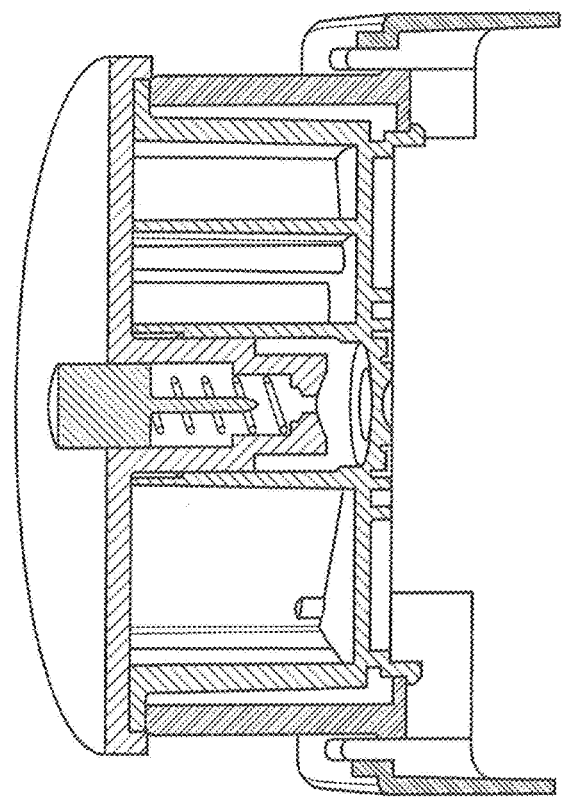
FIG. 56

METHOD AND SYSTEM FOR SAMPLE PREPARATION

CROSS-REFERENCE TO RELATED APPLICATIONS

This application is a divisional application of U.S. Non-Provisional patent application Ser. No. 15/586,841, filed May 4, 2017, which is a continuation of U.S. Non-Provisional patent application Ser. No. 15/157,584, filed May 18, 2016, which is a continuation of U.S. Non-Provisional patent application Ser. No. 14/056,603, filed Oct. 17, 2013, now U.S. Pat. No. 9,347,086, which claims priority from U.S. Provisional Patent Application Ser. No. 61/715,003 (filed Oct. 17, 2012), which is a continuation-in-part of U.S. patent application Ser. No. 12/785,864, filed May 23, 2010, now U.S. Pat. No. 8,663,918, which claims priority from U.S. Provisional Patent Application Ser. No. 61/180,494, filed May 22, 2009, and which is also a continuation-in-part of U.S. patent application Ser. No. 12/754,205, filed Apr. 5, 2010, now U.S. Pat. No. 8,716,006, which claims priority from U.S. Provisional Patent Application Ser. No. 61/166,519, filed Apr. 3, 2009. The contents of the aforementioned applications are hereby incorporated by reference in their entirety.

GOVERNMENT LICENSE RIGHTS

The U.S. Government has a paid-up license in this invention and the right in limited circumstances to require the patent owner to license others on reasonable terms as provided for by the terms of one or more of the following Grant Award Nos. DMI-0450472 and IIP-0450472 awarded by National Science Foundation, Contract No. W81XWH-07-2-0109 awarded by US Army Medical Research and Material Command, Contract Nos. W911NF-06-1-0238 and W911NF-09-C-0001 awarded by US Army RDECOM ACQ CTR.

FIELD OF THE INVENTION

This invention relates to a method and system for analyzing biological samples. More particularly, this invention relates to multi-chamber valves, and more particularly to multi-chamber disposable cartridges for use in biological sample analysis.

BACKGROUND

There is continuing interest to improve testing methodologies and decrease time demands on clinical laboratories. Particular testing requires that a sample be disrupted to extract nucleic acid molecules such as DNA or RNA.

It is estimated that about 30 million molecular diagnostic tests took place in US medical facilities in 2007. This figure is expected to increase to 67 million in 2009. Many, if not all of these assays, could benefit from a rapid sample preparation process that is easy to use, requires no operator intervention, is cost effective and is sensitive to small size samples.

The use of molecular diagnostics and gene sequencing in research and medical diagnostics are rapidly growing. Molecular techniques provide higher levels of specificity and sensitivity than antibody methods. Genetic sequencing allows for the collection of large amounts of information not previously available. However, sample preparation is a major cost component of running PCR (polymerase chain reaction), real-time PCR, gene sequencing analysis and hybridization testing. In addition, it delays test results and limits the ability to run these assays to laboratories with well trained personnel.

Nucleic acid based identification of biological material first requires isolation of the nucleic acid molecules (NAMs) from the sample. In order for a system to effectively and efficiently meet the user's needs, a universal sample preparation process is required. Current sample preparation processes are laborious, time consuming and require laboratory capability.

Therefore, there is a need for an improved testing system and methodology that addresses at least some of these shortcomings.

SUMMARY

The present invention relates to a sample preparation device. The sample preparation module is designed to identify and validate components for ultrasonic disruption and magnetic manipulation of nucleic acid molecules. In one embodiment, all processing steps occur within a disposable cartridge.

In another embodiment, a disposable cartridge is provided for preparing an assay fluid, comprising: cartridge body and a cylindrical rotor rotationally mounted to the cartridge body. The cartridge body includes (i) a cylindrical surface defining a fixed port and (ii) a syringe barrel defining a bore for receiving a moveable plunger. The fixed port is disposed in fluid communication with the bore of the syringe barrel. The rotor includes a surface slideably engaging the cylindrical surface of the cartridge body along a mating interface, a plurality of chambers each configured to facilitate at least one operation on the assay fluid, and a plurality of moveable ports disposed along the surface of the rotor and in fluid communication with at least one of the plurality of chambers. Furthermore, the rotor is rotationally indexed about an axis parallel to the cylindrical surface such that the plurality of moveable ports are selectively aligned with the fixed port of the cartridge body.

BRIEF DESCRIPTION OF THE DRAWINGS

The present invention is disclosed with reference to the accompanying drawings, wherein:

FIG. 34 demonstrates nucleic acid molecules isolated from fruit flies and that the addition of a size stabilizer in lanes two and three protect the nucleic acid molecules from over-shearing, whereas the samples without the denaturants were sheared to a level well below 100 base pairs;

FIG. 35 shows that using this process the nucleic acid molecules from a wide variety of different samples can be treated with the same power levels and time of sonication to give the same size distribution of fragments;

FIG. 47A is a cutaway view of an exemplary drive assembly; FIG. 47B is a bottom view of an insert while FIG. 47C is a cut away view of the insert;

FIG. 48A and FIG. 48B are views of a first exemplary insert pod while

FIG. 53 depicts a cover that uses an absorbing solid to collect a liquid sample;

FIG. 54 depicts an alternate embodiment of a cover that uses an absorbent solid;

FIG. 56 is another embodiment of a lance-based system.

Corresponding reference characters indicate corresponding parts throughout the several views. The examples set out herein illustrate several embodiments of the invention but should not be construed as limiting the scope of the invention in any manner.

DETAILED DESCRIPTION

Figure 1A:
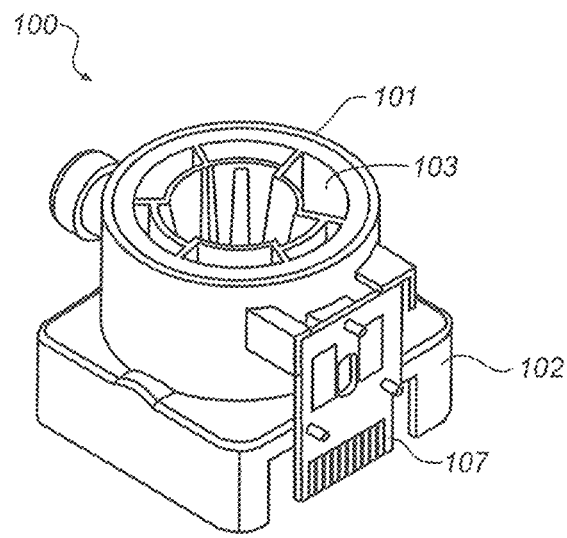
FIGS. 1A-1B show a graphical representation of a disposable cartridge according to one embodiment.
Figure 1B:
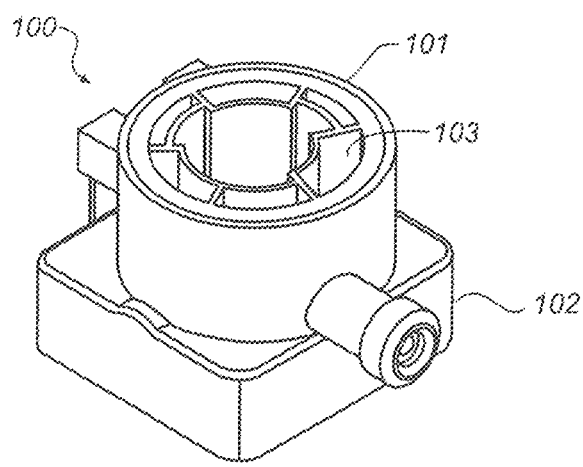

Referring to FIG. 1A and FIG. 1B there is shown an exemplary assembled disposable cartridge 100. The disposable cartridge 100 comprises a rotor 101. The rotor 101 is rotatabily situated within a cartridge body 102. The rotor 101 comprises chambers 103 for containing or treating fluid; a plurality of fluid paths for connecting the chambers 103 to external ports; and fluid through channels for transmitting fluids.

The disposable cartridge 100 provides an automated process for preparing a biological sample for analysis. The sample preparation process of the instant invention can prepare fragments of DNA and RNA in a size range of between 100 and 10,000 base pairs. The exact distribution of sizes can be varied by changing concentrations of surfactants, the surfactants used or the frequency of sonication. The ability to produce fragments in the desired size range obviates the need for electrophoresis or column isolation. This also increases the overall yield of useful fragments by eliminating the need for addition purification steps. A sample preparation module allows for disruption of cells, sizing of DNA and RNA, concentration and cleaning of the material. Additional chambers in the rotor can be used to deliver the reagents necessary for end-repair and kinase treatment. Enzymes can be stored dry and rehydrated in the cartridge or added to the cartridge just prior to use.

The use of a rotating design allows for a single plunger to draw and push fluid samples without the need for a complex valve system to open and close at various times. This greatly reduces potential for leaks and failure of the device compared to conventional systems. Furthermore, the use of a plunger allows for greater configurability in adjusting the amount of fluid drawn. The disposable cartridge 100 can be stored in a rotary position that leaves all ports and vents closed. This allows for long-term storage and shipping of the disposable cartridge 100 with liquid and solid reagents loaded within the disposable cartridge 100. In use, the disposable cartridge 100 is inserted into a detection device that is in electrical communication with a chip 107 (see FIG. 2). The detection device further affixes the cartridge body 102 into a fixed position.

Figure 2:
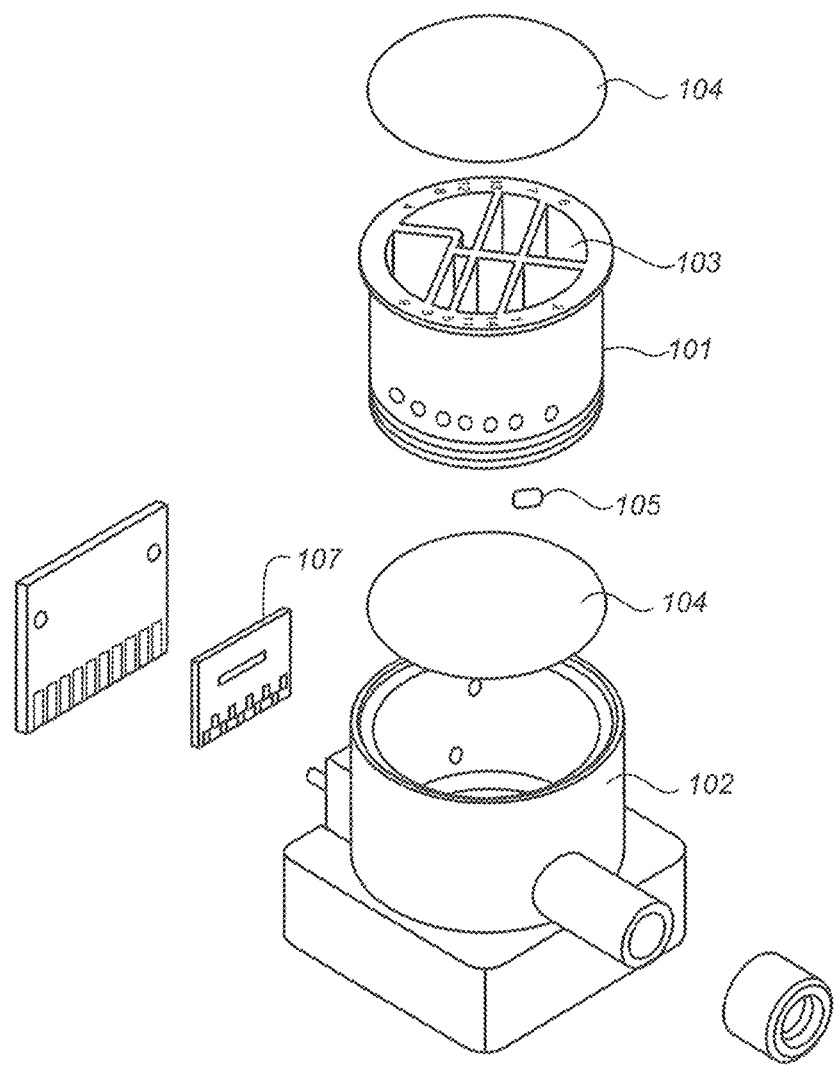
FIG. 2 shows an expanded view of a disposable cartridge according to one embodiment.

Referring to FIG. 2 there is shown an exploded view of the disposable cartridge 100. The rotor 101 is capable of containing a plurality of fluids in the various chambers 103. The exterior of the rotor 101 is cylindrical to allow free rotation about its axis when encased in the cartridge body 102. The interior section of the rotor 101 can be modified to include any size or shape chamber. Customized disposable cartridges retain the same exterior shape and dimensions and can be inserted into existing detection devices. The processing protocol of the detection device is easily modified to account for any new chambers, sample sizes, processing times, or port locations. In one embodiment, the rotor 101 is formed by an injection molding technique. In another embodiment, both the rotor 101 and the cartridge body 102 are formed through injection molding techniques. Injection molding allows for the production of customized disposable cartridges with minimal costs. The disposable cartridge 100 is configured to allow fluid contained in the chambers 103 to pass through certain fluid paths. The design allows for easy manufacturing and assembly. The design further allows for the disposable cartridge 100 to be used in instruments requiring a plurality of fluids. In one embodiment, the disposable cartridge 100 is a single use piece for use in detection devices. The disposable cartridge 100 contains the necessary fluids for biological testing and further is capable of being injected with a field sample.

Referring again to FIG. 2, the heat seal films 104 seal the fluids into the rotor 101 and prevent leaks while allowing for the manipulation of fluid samples. The heat seal films 104 seal the chambers 103 from the outside environment. The heat seal films 104 further allow for fluid to be added to or removed from the chambers 103 without compromising the integrity of the seal. In one embodiment, the heat seal films 104 improve energy transfer into and out of the chambers 103 of the rotor 101. Energy transfer includes but is not limited to heat, ultrasonic and magnetic. In one embodiment, a filter 105 is placed in-line with particular fluid paths to filter large solids from the fluid. In one embodiment, once the heat seal films 104 are sealed onto the rotor 101, the rotor 101 is affixed to the cartridge body 102. In one embodiment, the rotor 101 snaps into the cartridge body 102. It is understood that the heat seal films 104 can be sealed to the rotor 101 after the rotor 101 is affixed to the cartridge body 102.

In one embodiment a chip 107 containing biological probes is affixed to the cartridge body 102. The fluid contained in the chambers 103 is transferred to contact the chip 107 containing biological probes initiating reaction or detection chemistry. The chip 107 is in communication with a detection device, such as a bench-top detection device or portable detection device, to indicate the presence of a target analyte in a sample.

Figure 3A:
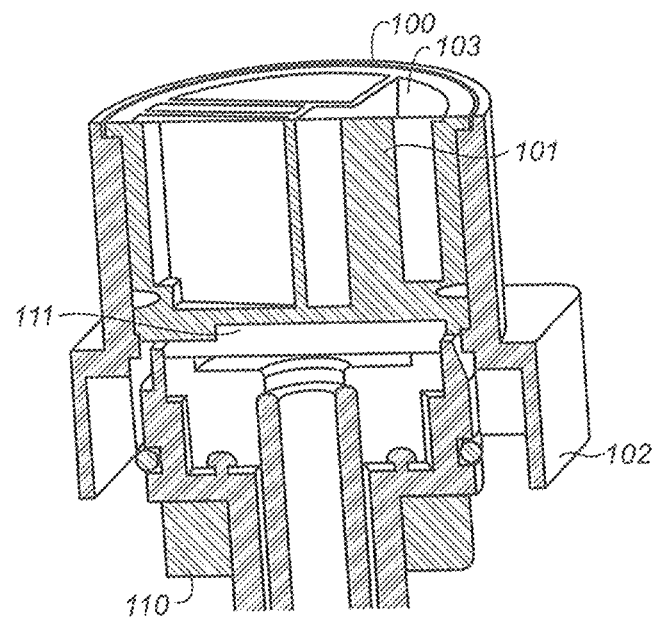
FIG. 3A shows a cross-sectional view of a disposable cartridge according to one embodiment.
Figure 3B:
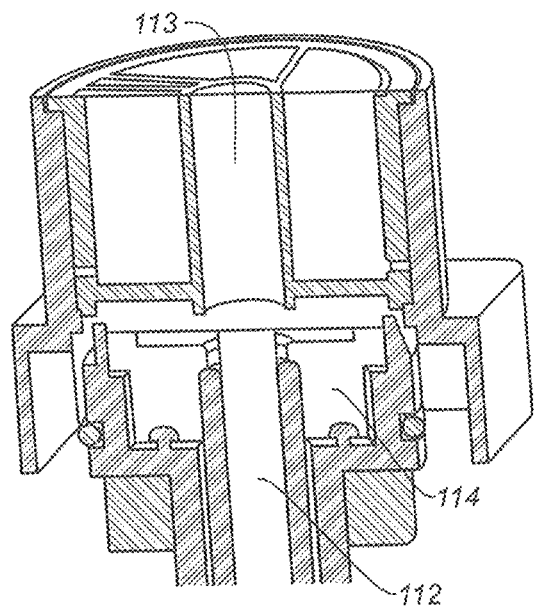
FIG. 3B shows a cross-sectional view of a disposable cartridge according to one embodiment having a magnet and sonicator in the cartridge.

Referring now to FIG. 3A and FIG. 3B there is shown a cross sectional view of the disposable cartridge 100. The disposable cartridge 100 is set onto a cartridge drive 110. The cartridge drive 110 is capable of rotating the rotor 101 to a desired rotary position. The cartridge drive 110 rotates the rotor 101 while the cartridge body 102 remains stationary. In one embodiment the cartridge drive 110 has one or more heaters 111. The heater 111 is capable of heating the fluids contained in the chambers 103 to a desired temperature. Alternatively, heating chambers are strategically positioned above the heater 111 to heat the fluid in the heating chamber without significantly heating the fluids in the chambers 103. In one embodiment, the heat film seals 104 facilitate this heating without significantly heating the fluids in the chambers 103. Various treatment chambers are incorporated into the rotor 101 to facilitate mixing, heating, disrupting, pressurization or any other treatment process. In one embodiment, cartridge drive 110 includes a magnetic 114. The magnet 114 is utilized to generate a magnetic field. The magnet 114 can pull or push magnetic nanoparticles in the rotor 101. The magnet 114 can concentrate a sample of magnetic nanoparticles or speed up the diffusion process by guiding any magnetic nanoparticles. See the section of this specification entitled "magnetic manipulation."

Figure 33:
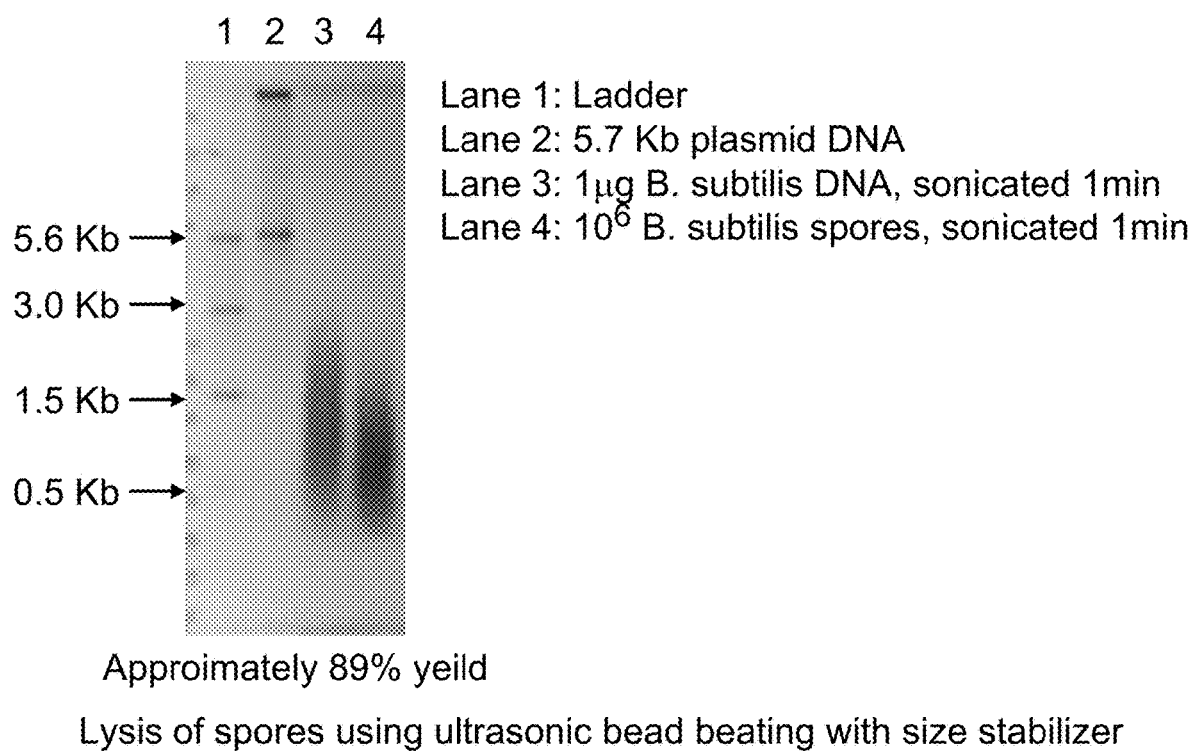
FIG. 33 demonstrates the effective release of nucleic acid molecules from the lysis of spores using ultrasonic bead beating with size stabilizer.

A mechanical force, such as a shearing force, is applied to a biological sample to disrupt the sample and cause it to release nucleic acid molecules. In one embodiment, the sample material is shredded with high speed nanoparticles utilizing sonication. This process disrupts cells, tissue or other materials to release nucleic acid molecules. It is understood that the mechanical force can be any force suitable for tearing apart the sample to release the nucleic acid molecules. Suitable mechanical forces include, but are not limited to sonication, nebulization, homogenization, etc. Bead beating is a process to isolate nucleic acid molecules from samples. It is a robust approach which is well suited for use with spores or tissue samples. In bead beating, glass beads of about 100 microns in diameter are used to crush the sample to release the nucleic acid molecules. The beads are moved using an ultrasonic source. FIG. 33 demonstrates the effective release of nucleic acid molecules from spore samples. In another embodiment, sharpened shards are used in place of, or in addition to, beads. These shards may be useful in releasing the nucleic acids from whole organisms (e.g. insect bodies) or similarly resilient structures.

For example, in one embodiment the cartridge drive 110 has a disruptor 112. The disruptor 112 is capable of mixing or disrupting the fluids contained in the chambers 103 by applying an ultrasonic force. The exemplary disposable cartridge 100 has a disrupting chamber 113 for mixing fluids in a chamber distinct from the chambers 103. In one embodiment small beads are located in the disrupting chamber 113 or in one of the chambers 103 to assist in mixing fluids or breaking down samples. The disrupter 112 applies an ultrasonic force causing the beads to become excited and move through the fluid.

A size stabilizer is present during the disruption step to obtain nucleic acid molecules within a usable size range. In one embodiment, the nucleic acid molecules are reduced to sizes between 200 and 10,000 base pairs in length. In another embodiment the nucleic acid molecules are reduced to sizes between 300 and 3,000 base pair in length. In another embodiment the nucleic acid molecules are reduced to sizes between 400 and 2,000 base pair in length. In another embodiment the nucleic acid molecules are reduced to sizes between 200 and 500 base pair in length. It is understood that the desired base pair length will vary depending on the downstream sample processing technique. Sample processing techniques include, but are not limited to hybridization, PCR, real-time PCR, reverse transcription-PCR, "lab-on-a-chip" platforms and DNA sequencing.

Referring to FIG. 4A to FIG. 4D there are shown various views of one embodiment of the cartridge body 102. It is understood that various designs can be used to house the rotor 101. The cartridge body 102 has an inner cylindrical surface 140. The cylindrical surface 140 houses the rotor 101 (see FIG. 2). The cylindrical surface 140 is smooth to allow the rotor 101 to freely rotate. The cartridge body 102 is constructed from any material that is both ridged enough to support the cartridge body 102 and smooth enough to allow for rotation of the rotor 101. In one embodiment, the cylindrical surface 140 has a slight taper to facilitate attachment of the rotor 101 that also has an outer cylindrical surface with a slight taper.

Figure 4A:
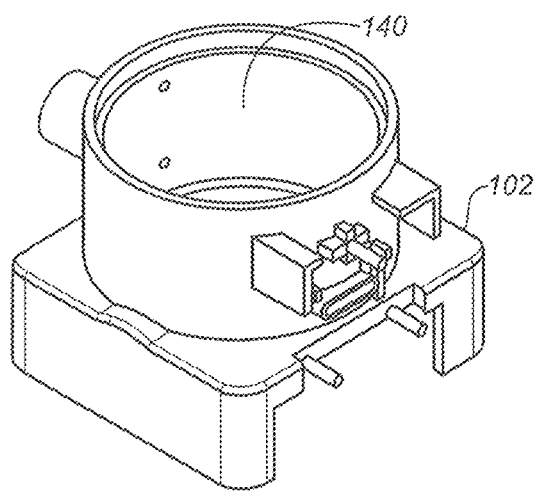
FIGS. 4A-4D show a graphical representation of the cartridge body according to one embodiment.
Figure 4B:
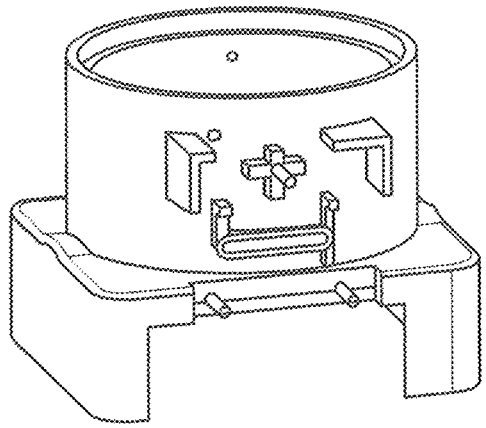
Figure 4C:
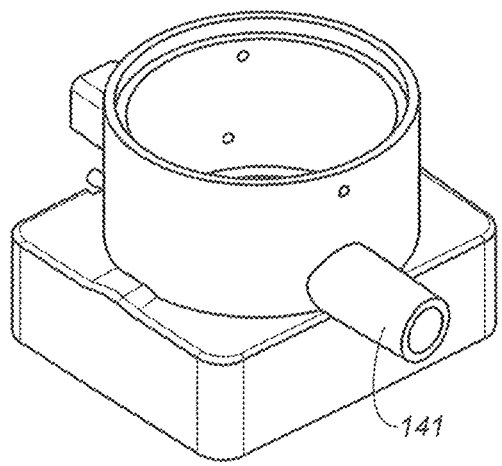

As shown in FIG. 4A to FIG. 4D, in one embodiment the cartridge body 102 has a syringe molding 141. Although only one syringe molding is shown it is understood that a plurality of syringe moldings can be used. In the embodiment of FIG. 4C, the syringe molding 141 is a hollow pipe that extends perpendicular from the vertical edge of cartridge body 102. The syringe molding 141 is capable of housing a plunger. The plunger draws and pushes fluids through the fluid paths of rotor 101.

Figure 4D:
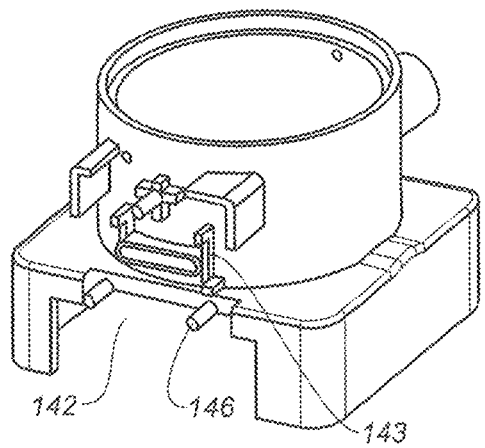
Figure 5A:
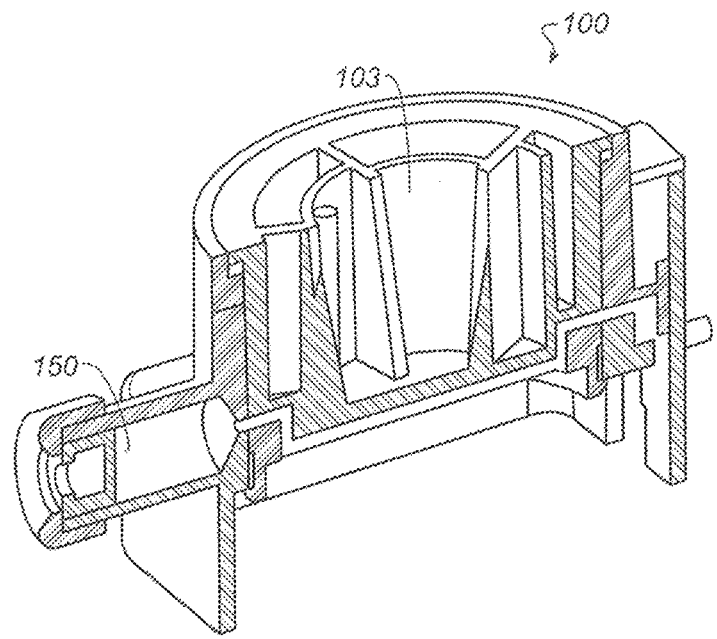
FIGS. 5A-5B show a cross-sectional view of an assembled disposable cartridge according to one embodiment having the multi-chamber insert secured in the cartridge body.
Figure 5B:
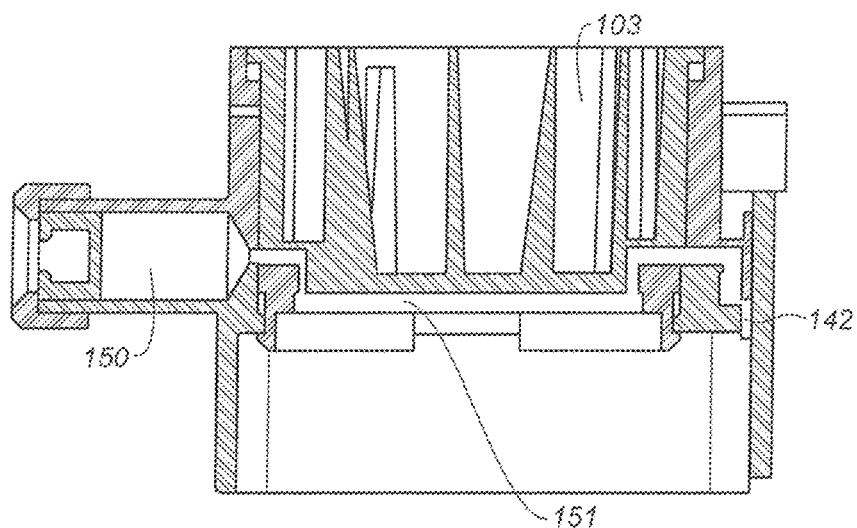
Figure 6A:
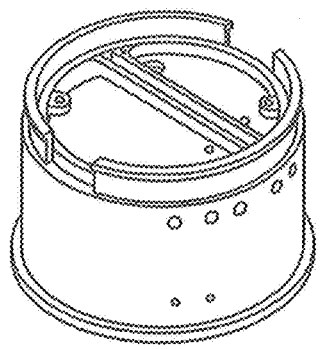
FIGS. 6A-6G show a graphical representation of the multi-chamber insert according to one embodiment.
Figure 6B:
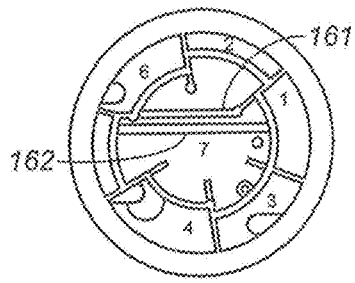
Figure 6C:
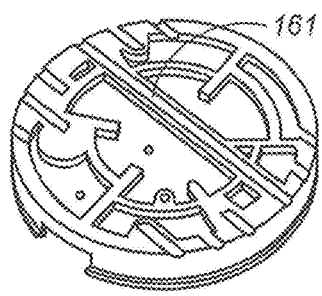
Figure 6D:
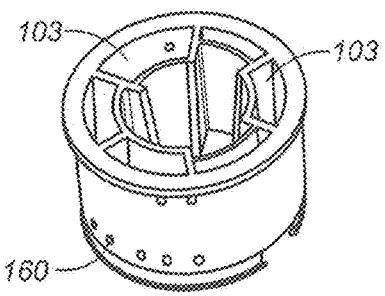
Figure 6E:
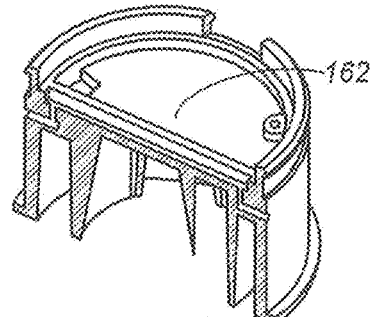
Figure 6F:
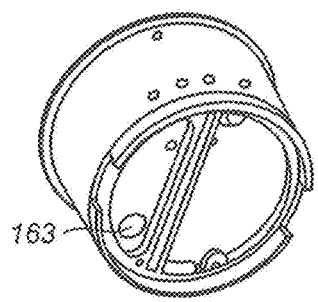
Figure 6G:
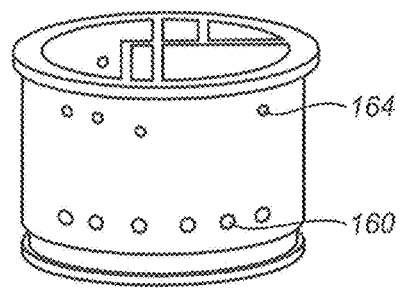

Referring to FIG. 5A and FIG. 5B there is shown a cross sectional view of the assembled disposable cartridge 100 having a plunger 150. The plunger 150 is capable of drawing fluid from the chambers 103. Once the plunger 150 draws the fluid, the disposable cartridge repositions the fluid path to align a distinct port with the syringe molding 141 which is in fluid communication with a reaction chamber 142 or a different chamber 103. The plunger 150 then pushes the fluid through the fluid path 151 into the reaction chamber 142 or the different chamber 103. In one embodiment the plunger 150 is retained within the syringe molding 141. The fluids chemically react with other fluids or devices in communication with the reaction chamber 142 where it contacts the chip 107 (see FIG. 2). In one embodiment the chip 107 has a reactive surface and is mounted on a sensor board. In one embodiment the chip 107 forms one side of the reaction chamber 142. The chip 107 is in electrical communication with a detection device to provide readings and results of the testing. As shown in FIG. 4D, a sensor mount 143 is capable of holding the sensor board. The sensor board is aligned to the sensor mount 143 by the alignment posts 146.

It is understood that a fluid output can be attached to the cartridge body 102 to allow the fluid to transfer from the disposable cartridge 100 to a desired location. Furthermore, a fluid input allows the introduction of fluids to the disposable cartridge 100. While a plunger 150 has been described in this embodiment, it is understood that any suitable fluid delivery device could be substituted to effectively transfer fluids within the cartridge.

Referring to FIG. 6A to FIG. 6G there are shown multiple views of the rotor 101. The chambers 103 of rotor 101 can contain samples, standards, washes, catalysts or any other desirable fluids. In one embodiment the chambers 103 include a waste chamber to hold discharged fluids. The rotor 101 further contains multiple ports 160. Each port 160 has a unique fluid path. Each chamber has a fluid path that is in communication with a port to transfer fluid to or from the chamber. A syringe molding on the cartridge body (not shown) aligns with a port to extract or push fluid. To prevent pressure differentials from forming, pressure relief ports 164 are positioned along the rotor. In addition to the unique fluid paths, the rotor 101 contains at least one fluid through-channel 161. The fluid through channel 161 is an elongated channel that traverses at least a portion of the bottom panel or surface of the rotor 101 and allows the fluid to flow from the one end of the rotor 101 to the other. For example, the fluid can flow from the syringe molding 141, through a fluid through channel, and into the reaction chamber 142 of the cartridge body 102. To prevent fluid interaction in the fluid through channel 161 a plurality of fluid through-channels are used. A secondary fluid through-channel 162 is used to prevent early reactions or other adverse fluid interactions. In one embodiment the rotor 101 contains a heater contact region 163. The heater contact region 163 is positioned below the chambers 103 for which it is desirable to heat the fluid in the chamber. Furthermore, the heater 111 (see FIG. 3A) is capable of heating the fluid through channel 161.

Figure 7A:
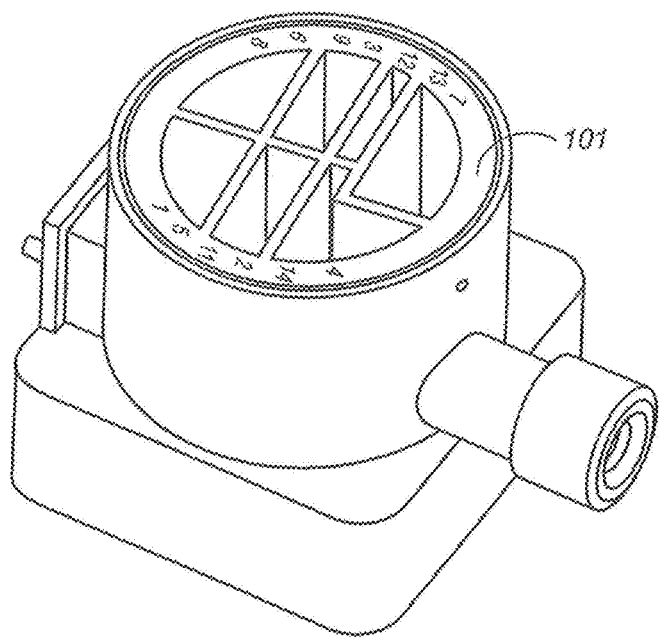
FIGS. 7A, 7B, 8A, 8B, 9A, 9B, 10A, 10B, 11A, 11B, 12A, 12B, 12C, 13A, 13B, 14A, 14B, 14C, 15A, 15B, 16A, 16B and 16C show various graphical representations of an assembled disposable cartridge with the multi-chamber insert positioned for desired fluid flow through the channels and ports according to one embodiment.
Figure 7B:
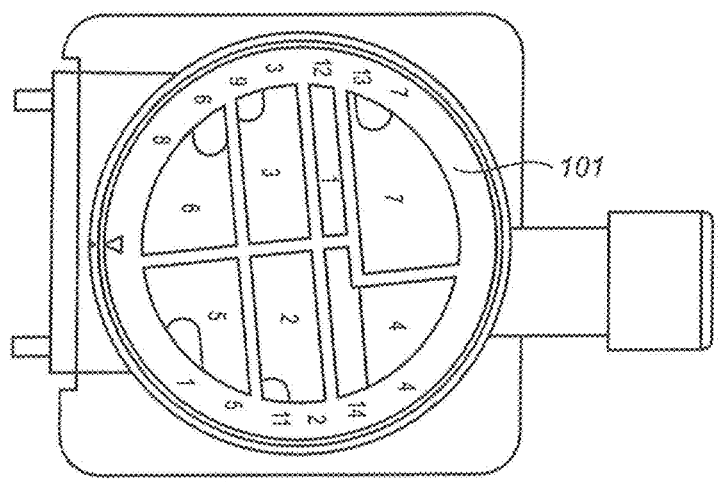

Referring to FIG. 7A to FIG. 16C there are shown multiple of views of an assembled disposable cartridge rotated in various positions. As shown in FIG. 7A and FIG. 7B the rotor 101 is in a closed position. No ports 160 are aligned with the syringe molding 141. This prevents any leakage of fluid from the chambers 103. In one embodiment at least one chamber 103 is a sample chamber. The sample chamber enables the user to inject a fluid sample into the chamber through the heat film seal. In one embodiment the sample chamber contains disrupting objects, such as glass beads, to assist in breaking down samples into testable nucleic acid strands.

Figure 8A:
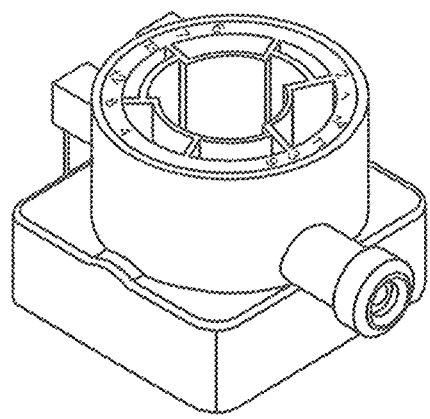
Figure 8B:
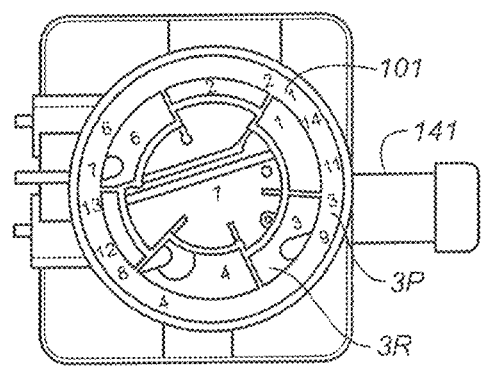

Referring to FIG. 8A and FIG. 8B the rotor 101 has a rotary position such that port 3P is in-line with the syringe molding 141. Once positioned fluid from a chamber 3R that is fluidly connected to port 3P can be drawn through port 3P and into the syringe molding 141. Once fluid is pulled from the chamber 3P, and no additional fluid is required from that chamber, that chamber can be used as an alternative chamber for waste storage.

Figure 9A:
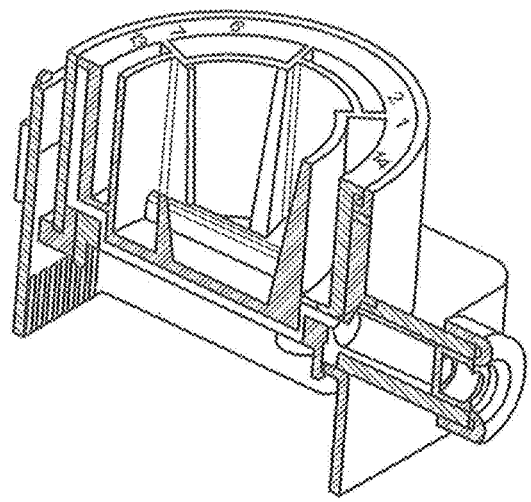
Figure 9B:
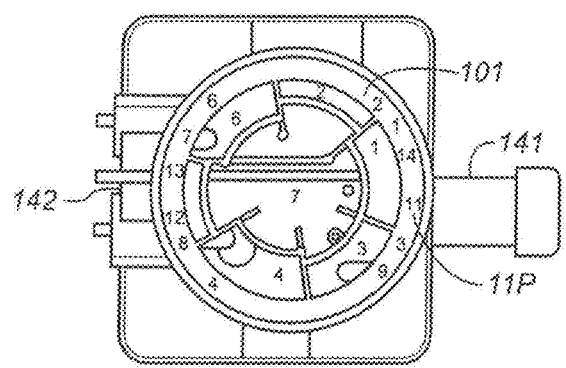

Referring to FIG. 9A and FIG. 9B, the rotor 101 has a rotary position such that port 11P is aligned with the syringe molding 141. In the embodiment depicted, port 11P is fluidly connected to reaction chamber 142. The plunger 150 pushes the fluid within the syringe molding 141 into port 11P and the fluid passes to the reaction chamber 142.

Figure 10A:
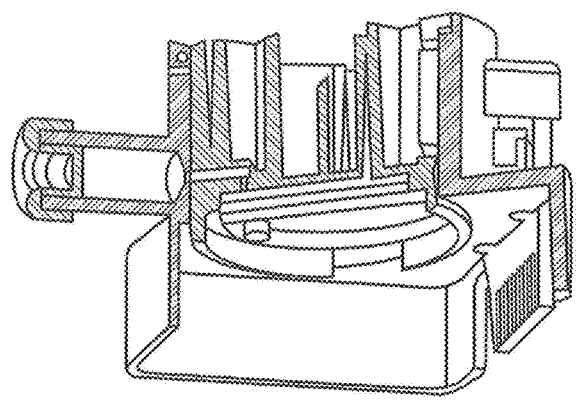
Figure 10B:
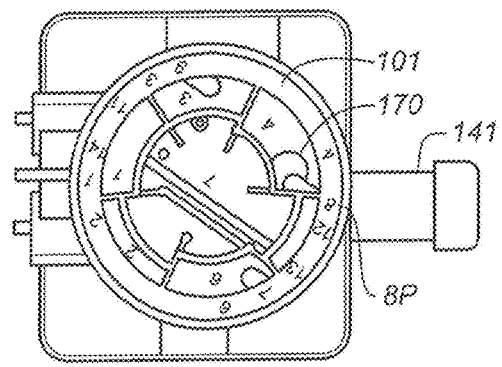

Referring to FIG. 10A and FIG. 10B the rotor 101 is positioned such that port 8P is aligned with the syringe molding 141. In one embodiment fluid is pushed from the syringe molding 141 into port 8P and into a chamber 103 disposed proximate a heating chamber 170. Once in the heating chamber 170 the fluid is heated at the desired temperature for a predetermined amount of time.

Figure 11A:
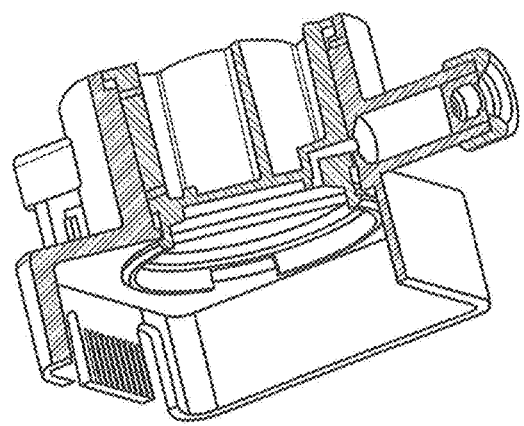
Figure 11B:
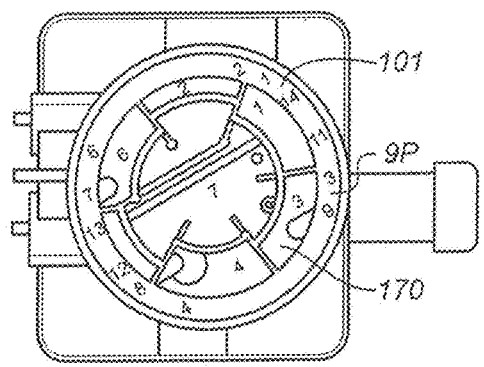

Referring to FIG. 11A and FIG. 11B, once the heating is completed the fluid is drawn back into the syringe molding 141. It is understood that the fluid may be drawn through the same port 8P or unique port in communication with the heating chamber 170. As shown in FIG. 11A and FIG. 11B the fluid is drawn into the syringe molding 141 from a unique port 9P in communication with the heating chamber 170.

Figure 12A:
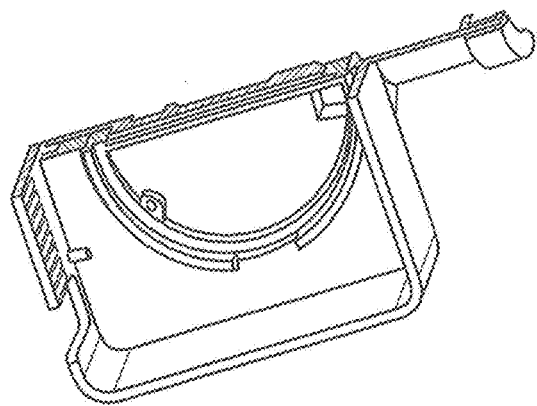
Figure 12B:
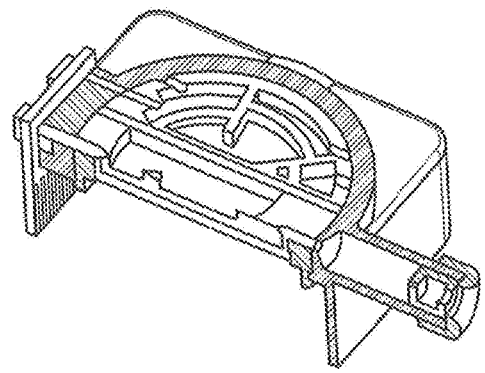
Figure 12C:
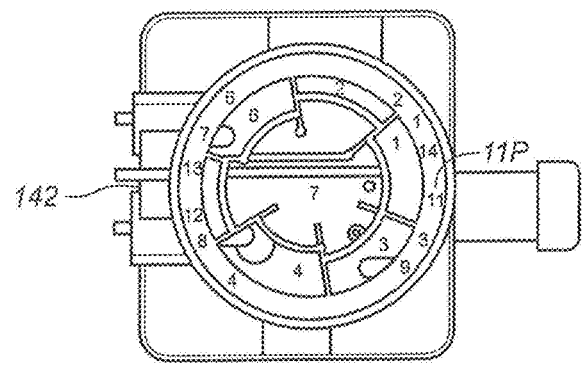

Referring now to FIG. 12A to FIG. 12C there is shown a fluid path from the syringe molding 141 to the reaction chamber 142. In this embodiment the reaction chamber 142 is fluidly connected with port 11P.

Figure 13A:
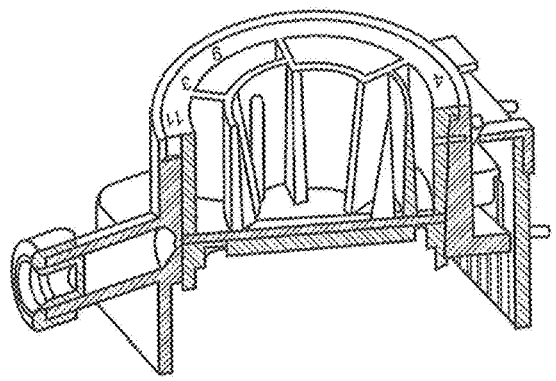
Figure 13B:
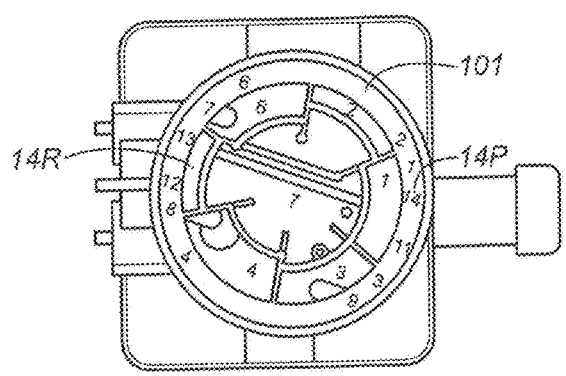
Figure 14A:
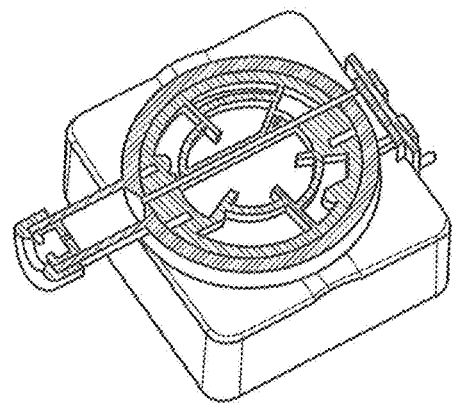
Figure 14B:
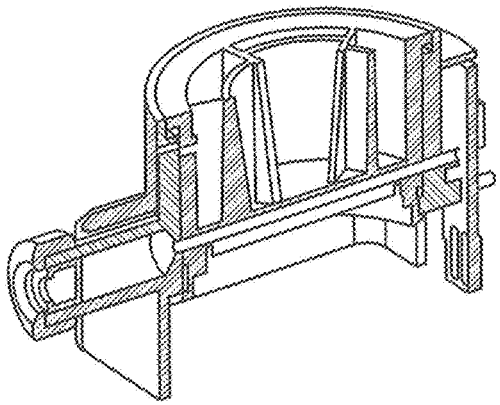
Figure 14C:
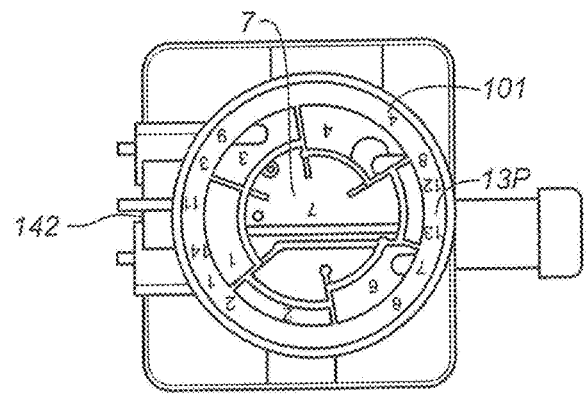

Referring to FIG. 13A and FIG. 13B there is shown the rotor 101 positioned such that port 14P is aligned with the syringe molding 141. Chamber 14R is in communication with port 14P. The fluid contained in chamber 14R is pulled into the syringe molding. The rotor 101 then rotates to port 13P as shown in FIG. 14A and FIG. 14C. The fluid from chamber 14R is then pushed through port 13P to the reaction chamber 142. The fluid passes through a channel that is distinct from the channel associated with port 11P. This prevents fluids from coming in contact with and reacting with each other while in the channels. The fluids first come into contact in the reaction chamber 142.

After the desired reaction time the plunger 150 draws the fluid from the reaction chamber 142 and pushes the fluid into the waste chamber 7. The plunger 150 draws the fluid back through port 11P and the rotor 101 rotates to a port in communication with waste chamber 7. The plunger 150 then pushes the fluid into the waste chamber 7. It is understood that after use any chamber can be utilized as a waste chamber. In an alternative embodiment, the plunger 150 stops pushing fluid once it reaches the reaction chamber 142. Upon completion of the reaction time, the plunger 150 continues to push the fluid through the reaction chamber 142 and into a port in communication with a waste chamber or separate archive chamber. An archive chamber stores the sample for additional testing or verification.

Figure 15A:
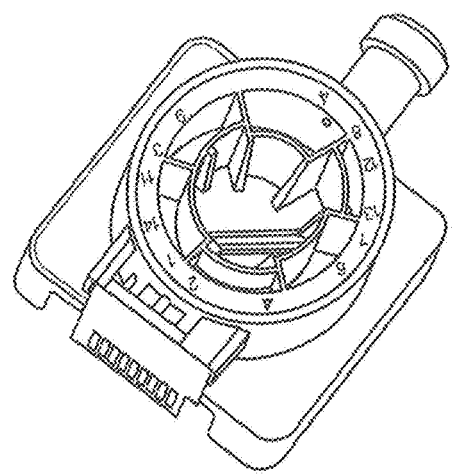
Figure 15B:
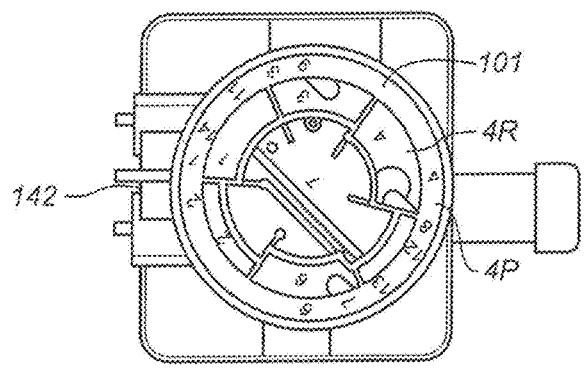

Referring to FIG. 15A and FIG. 15B there is shown the rotor 101 positioned such that port 4P is aligned with the syringe molding 141. Port 4P is in communication with chamber 4R containing a flushing fluid. The flushing fluid is drawn from chamber 4R through port 4P and into the syringe molding.

Figure 16A:
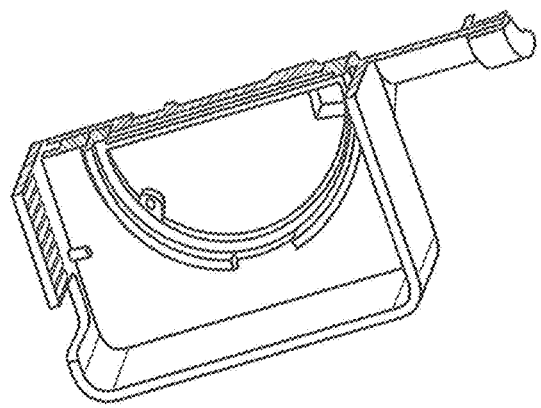
Figure 16B:
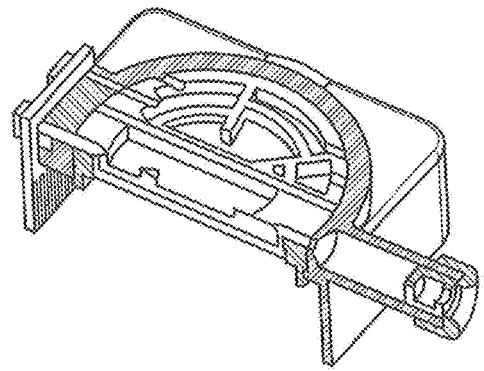
Figure 16C:
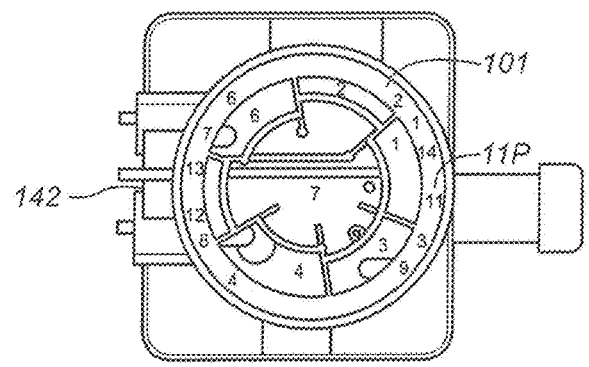

As shown in FIG. 16A, FIGS. 16B and 16C, the rotor 101 rotates to port 11P and the plunger pushes the flushing fluid into port 11P and to the reaction chamber 142.

Once processing is completed the disposable cartridge 100 can be removed from the detection device and disposed. A fresh disposable cartridge with the same or different configuration is then inserted into the detection device in preparation for the next use.

Figure 17:
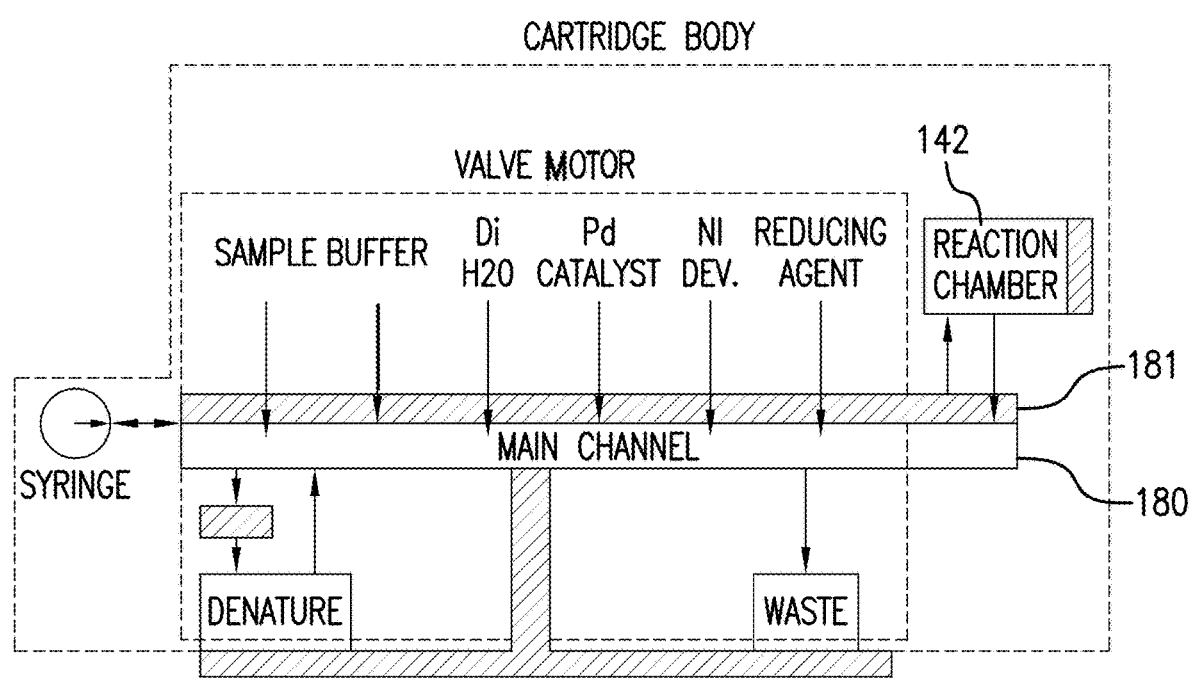
FIG. 17 shows a schematic representation of a disposable cartridge according to one embodiment.

Referring to FIG. 17 there is shown a schematic of a disposable cartridge of one embodiment. The exemplary rotor contains six fluids in various chambers. Five fluids pass from their respective chambers, into the syringe molding, through the main channel 180 and into a reaction chamber, such as reaction chamber 142. One fluid passes from the syringe molding through a secondary channel 181 and into the reaction chamber to prevent any contamination or premature reactions.

Figure 18:
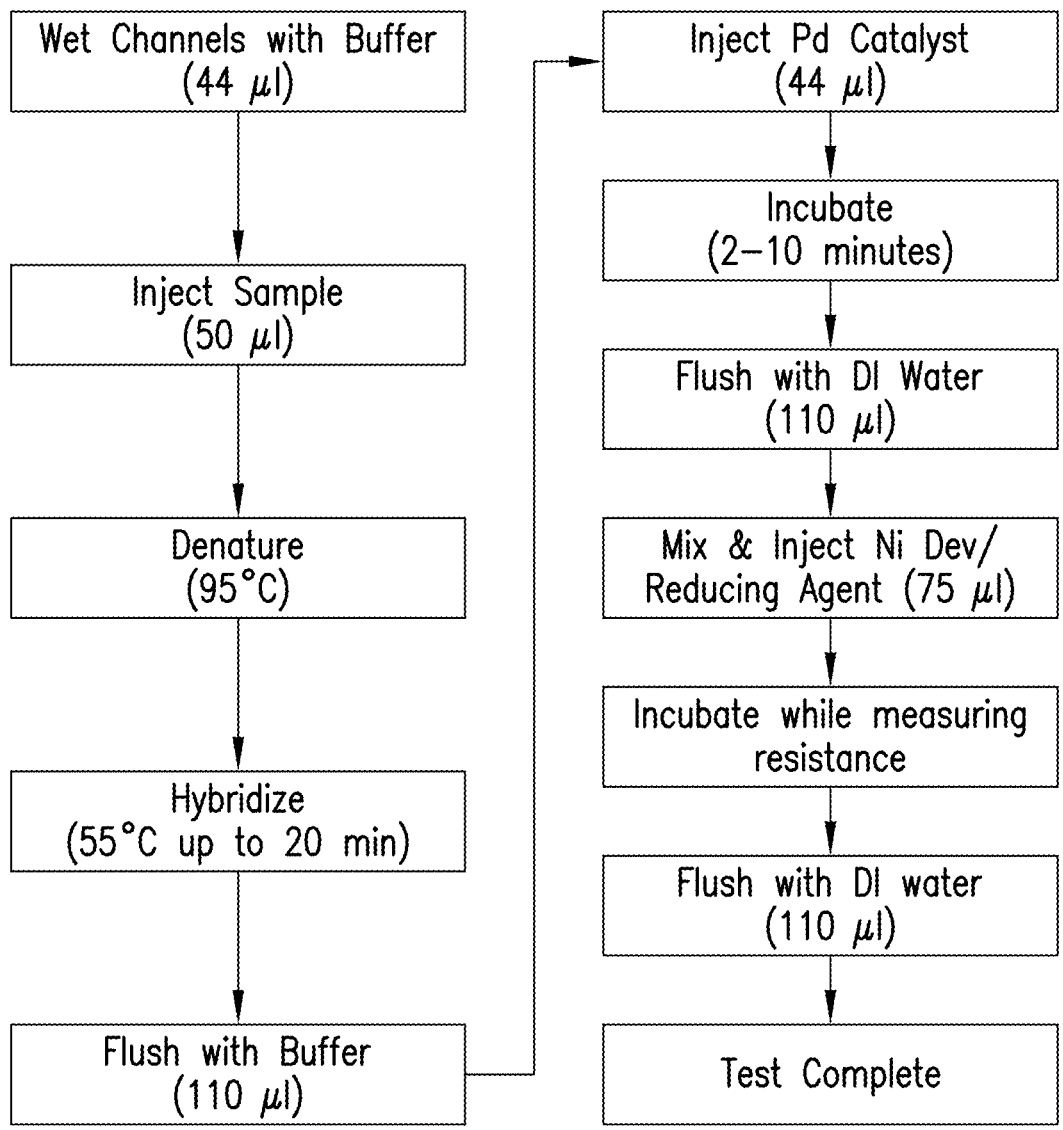
FIG. 18 shows a process flow chart for one use of a disposable cartridge according to one embodiment.

Referring to FIG. 18 there is shown a process flow according to one embodiment. Once a sample is injected into a sample chamber the detection device is activated and the testing begins. The channels are first preconditioned with a small amount of buffer. The sample is then transferred from the sample chamber to a heating chamber and heated at 95° C. for 5 minutes. The heated sample is then transferred to a reaction chamber to hybridize for 20 minutes. The hybridization process enables the sample to chemically bond with biological probes found on a chip in communication with the reaction chamber. The biological probes specifically bind to target nucleic acid molecules found in the sample as described in U.S. Pat. No. 6,399,303 issued to Connolly on Jun. 4, 2002, which is hereby incorporated by reference. It is understood that a single chip may contain a plurality of distinct and redundant biological probes to increase sensitivity and to test for a variety of target nucleic acid molecules. It is further understood that the disposable cartridge can be used in any system requiring the manipulation and transport of a plurality of fluids.

After hybridization, the sample is flushed with buffer to remove any excess compounds. In one embodiment, a catalyst such as palladium is transferred to the reaction chamber and allowed to incubate for 10 minutes. The remaining catalyst is then flushed with water. A mixture of a reducing agent and metal, such as nickel, is pushed into the reaction chamber. The metal coats the target sample creating a conductor on the chip. The excess non-bonded metal is flushed with water. The resistance across biological probes bonded together by a target sample coated in metal dramatically reduces, indicating the presence of the target sample. The detection device writes the results of the test and the test is complete.

Figure 19A:
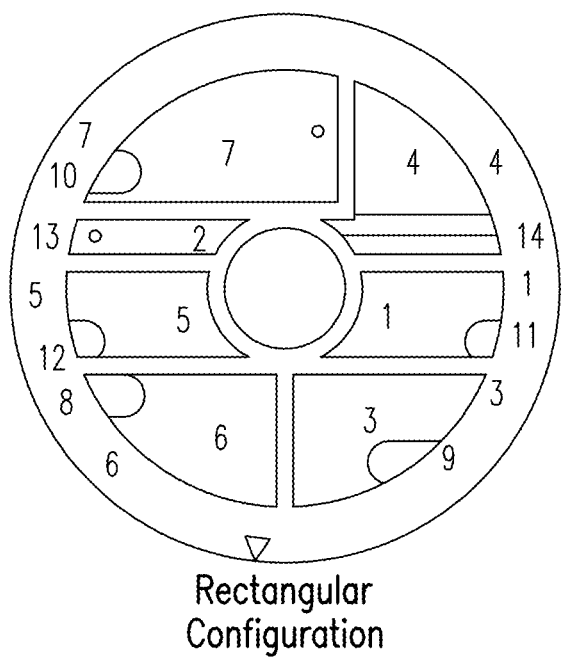
FIGS. 19A, 19B, 20A, 20B, 21A and 21B show a graphical representation of multi-chamber insert configurations according to various embodiments.
Figure 19B:
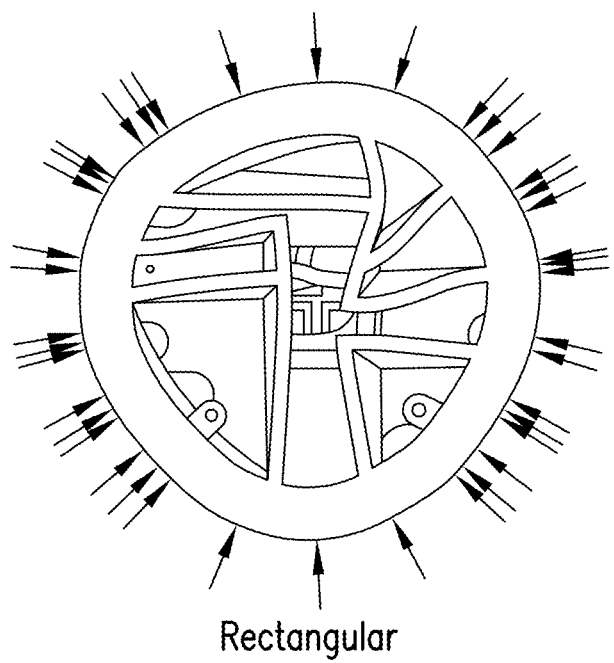

Referring now to FIG. 19A and FIG. 19B there are shown variations of the rotor. The chambers of the insert are shown in a rectangular configuration. Changes to the chamber sizes and shapes can be performed to optimize the particular reagent and waste chamber.

Figure 20A:
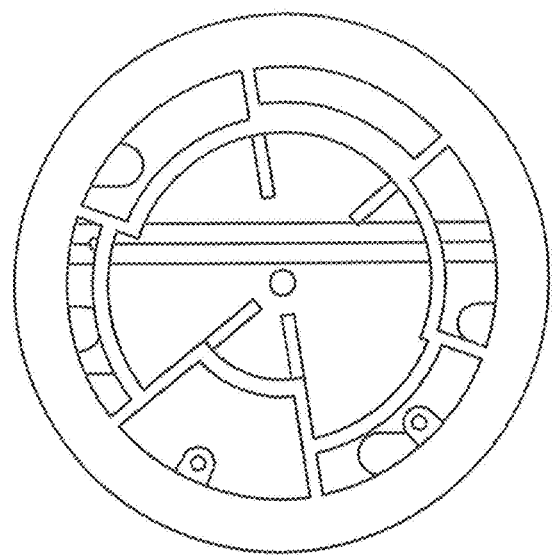
Figure 20B:
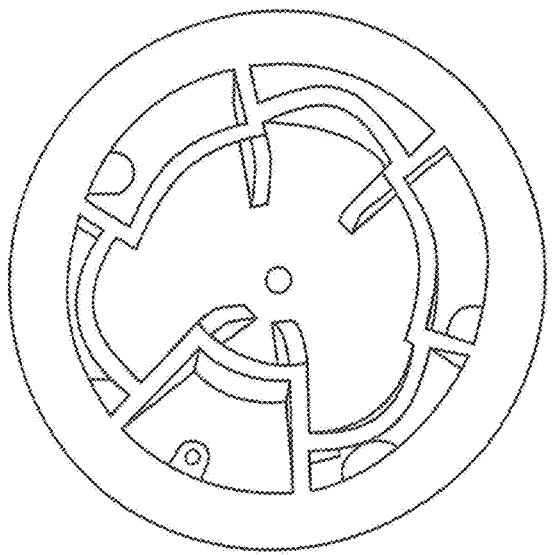

Referring now to FIG. 20A and FIG. 20B there are shown additional variations of the rotor. The chambers of this embodiment are shown to have radial chambers. In one embodiment the chambers are of uniform size and shape around the radius of the insert.

Figure 21A:
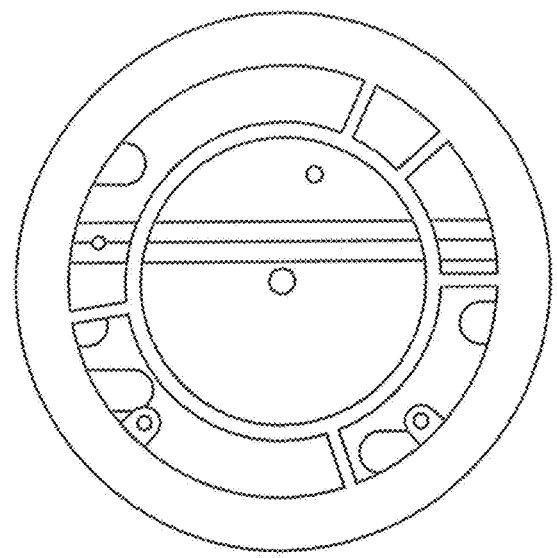
Figure 21B:
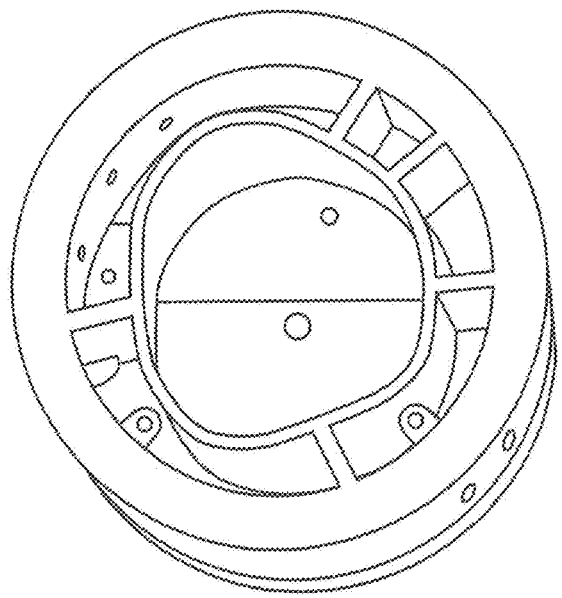

Referring now to FIG. 21A and FIG. 21B there are shown variations of the rotor. The chambers are of various sizes along the radius of the insert to house differing amounts of reagents within each chamber. While variations of the insert are shown in the various embodiments, it is understood that any variation of the rotor containing a plurality of ports and chambers can be used.

Figure 22:
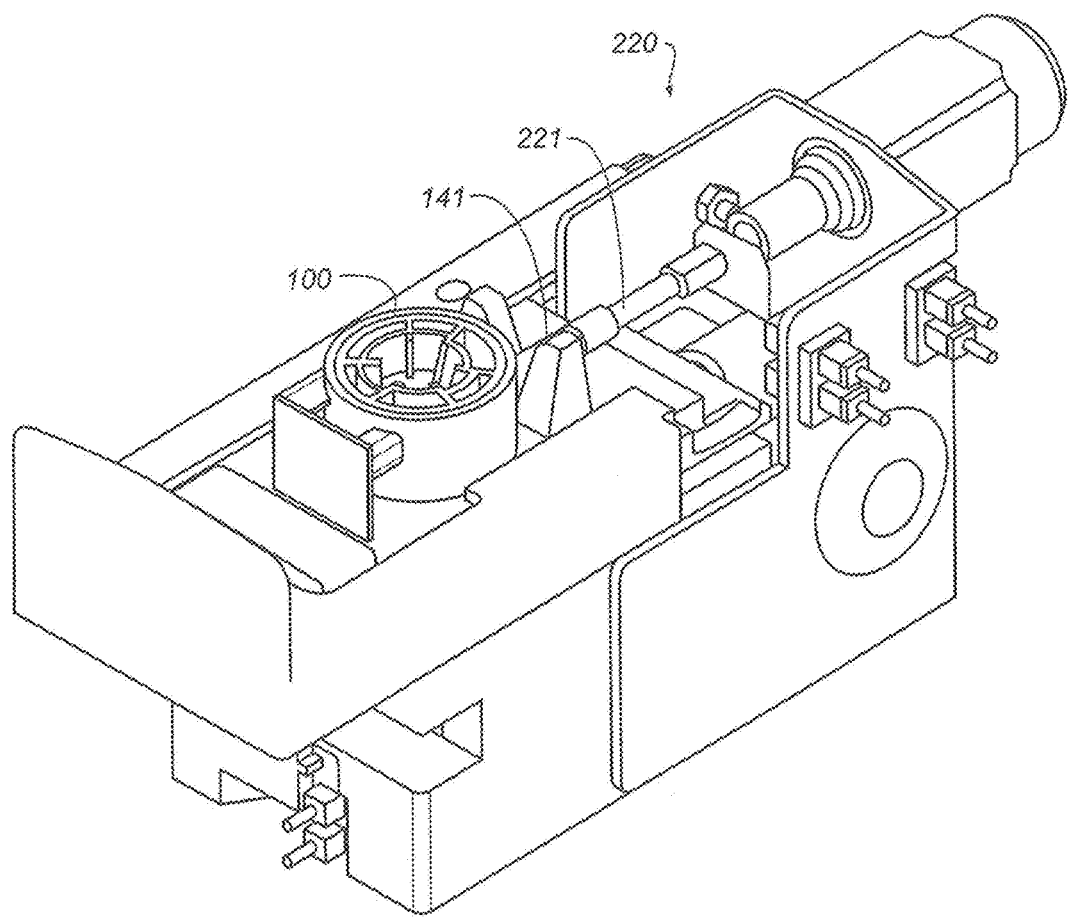
FIG. 22 shows a graphical representation of sampling device containing a cartridge drive and plunger drive according to one embodiment.
Figure 23:
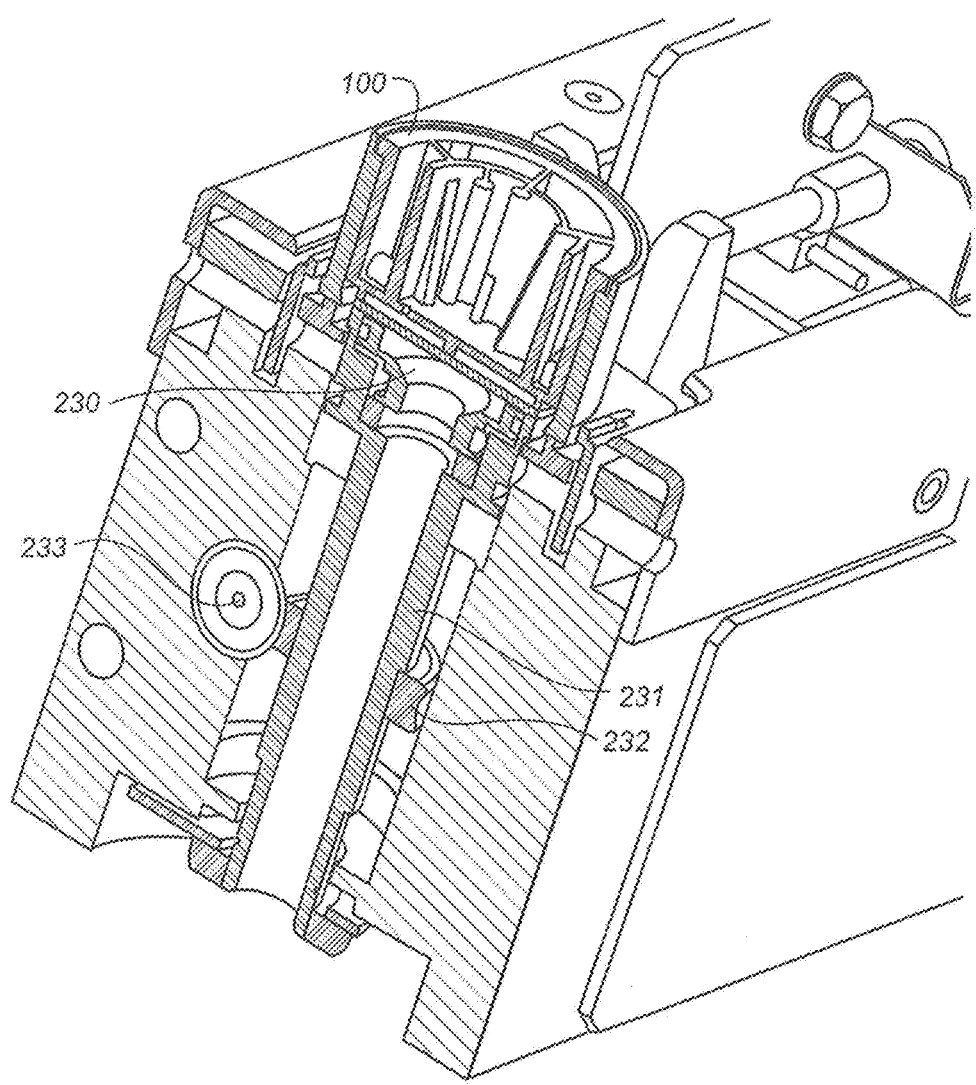
FIG. 23 shows a graphical representation of a cartridge drive with the disposable cartridge removed according to one embodiment.

Referring to FIG. 22 there is shown a sampling device having a plunger drive 220 and a cartridge drive (also see FIG. 23). The plunger drive 220 contains a long cylindrical section 221 having a tip 220. The tip of the plunger drive 220 connects to the plunger inside of the syringe molding 141. In one embodiment the tip of the plunger drive 220 is conical to improve contact with the plunger. The plunger drive 220 moves the cylindrical section 221 axially causing the plunger to either pull or push fluids from the chambers in the disposable cartridge 100. The disposable cartridge 100 sets on top of the cartridge drive.

Referring to FIG. 23 there is shown a cartridge drive according to one embodiment. The disposable cartridge 100 sets atop the contact surface 230. The contact surface 230 rotates to position the rotor 101 to a desired location within the disposable cartridge 100. In one embodiment the contact surface 230 is part of a drive assembly 231. A worm gear 232 is attached to the drive assembly 231. A worm drive 233 engages the worm gear 232 causing the drive assembly 231 to rotate. It is understood that any suitable means to rotate the rotor 101 can be employed.

Figure 24:
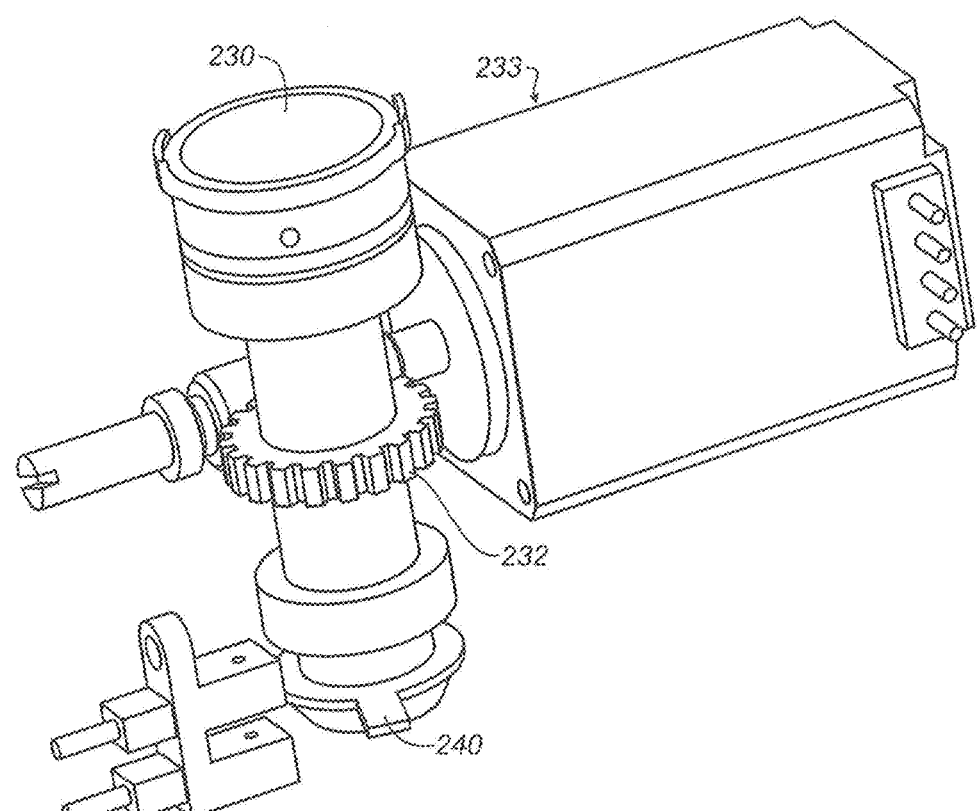
FIG. 24 shows a graphical representation of the stepper motor assembly and worm drive according to one embodiment.

Referring to FIG. 24 there is shown another view of the cartridge drive. The worm drive 233 is a stepper motor positioned to advance the worm gear 232. A home flag 240 is attached to the drive assembly to zero the device. At any time during fluid sampling the home flag can be zeroed allowing the worm drive 233 to advance the appropriate distance.

Figure 25:
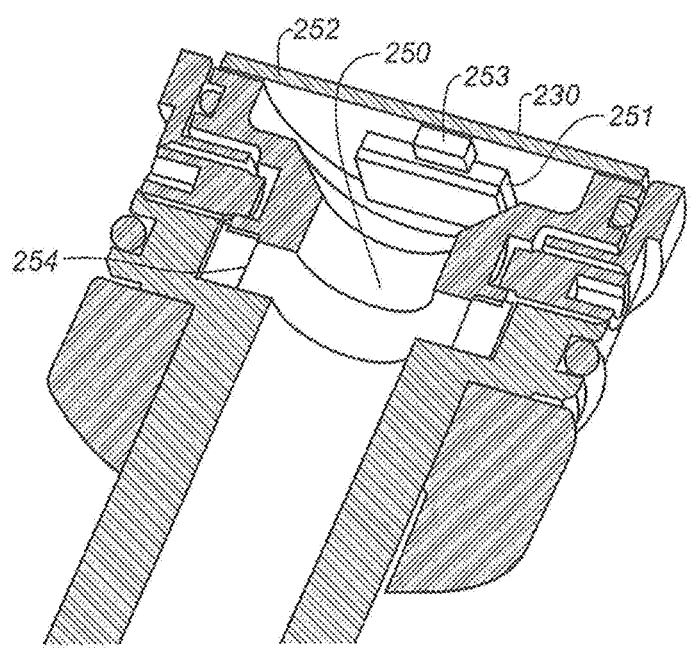
FIG. 25 shows a graphical representation of a heater according to one embodiment.

Referring to FIG. 25 there is shown the contact surface 230 having a heater. The contact surface 230 is spring loaded to improve contact with the disposable cartridge 100. At least one spring 254 is positioned to allow movement of the contact surface 230. In one embodiment the contact surface 230 contains a heater mount 250 to mount the heating elements. At least one resistor 251 is positioned on the heater mount 250. A heating plate 252 transfers heat from the resistor 251 through the heating plate 252 and to a desired location on the disposable cartridge 100. In one embodiment the heating plate 252 is an aluminum heating plate. In one embodiment, a temperature sensor 253 is positioned near the resistor 251 or heating plate 252 to detect the resulting temperature. It is understood that the contact surface 230 can be positioned over the heater plate. The contact surface is made from a material that allows an efficient thermal transfer from the heating plate to the disposable cartridge.

Figure 26:
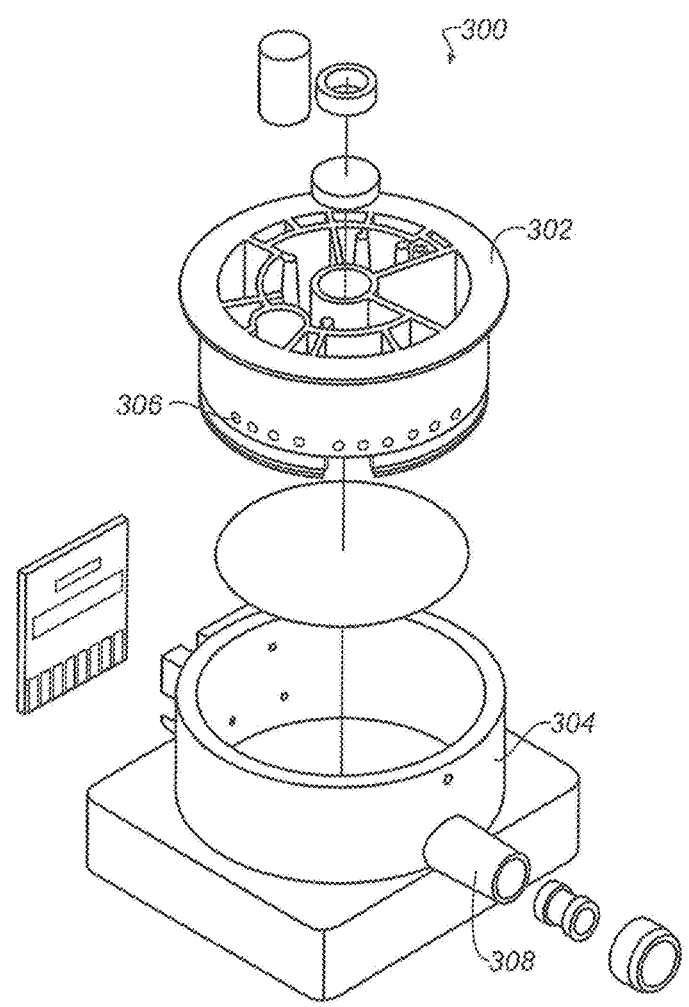
FIG. 26 shows a graphical representation of a disposable cartridge according to one embodiment.

Referring to FIG. 26, disposable cartridge 300 is depicted. Disposable cartridge 300 is similar to disposable cartridge 100 except in that a different rotor 302 is used. The rotor 302 is disposed within an cylindrical surface of cartridge body 304 and is rotatably connected thereto. The rotor 302 comprises a plurality of ports 306, each of which is connected to a corresponding chamber. In the embodiment of FIG. 26, each of the ports 306 are at the same predetermined height along the vertical edge of rotor 302. This permits each of the ports 306 to be selectively aligned with a single syringe mold 308. By rotating the rotor 302 relative to the cartridge body 304, each individual port 306 can be selectively aligned with syringe mold 308, thereby permitting fluid to be selectively injected or withdrawn from a desired chamber. In FIG. 26, the ports 306 are on the vertical edge of the rotor 302. In other embodiments, the ports 306 are disposed on other edges, such as a top or bottom edge.

Figure 27:
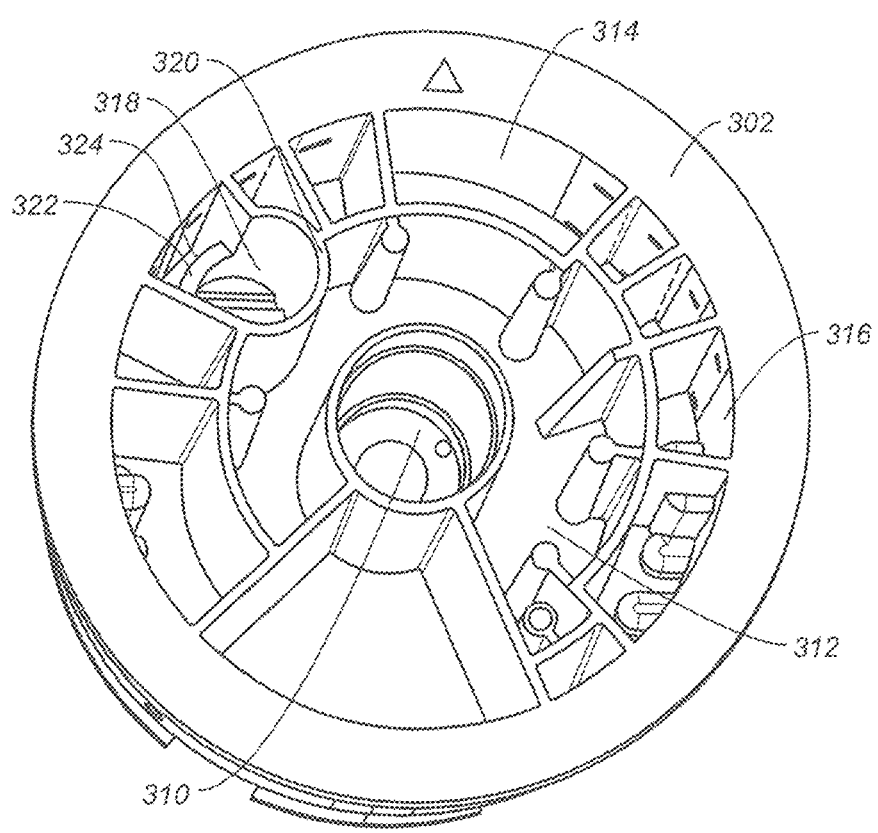
FIG. 27 is a top perspective view of an exemplary disposable cartridge.

Referring to FIG. 27, a top view of the rotor 302 is shown. Rotor 302 comprises a disrupting chamber 310 that is fluidly connected to a first port among the ports 306 (see FIG. 26). The disrupting chamber 310 of FIG. 27 is centered with respect to rotor 302. In other embodiments, the disrupting chamber 310 may be disposed elsewhere in rotor 302. In the embodiment depicted, the first port is connected to disrupting chamber 310 by a first elongated channel that traverses a portion of the bottom panel or surface of the rotor 302. The rotor 302 further comprises at least one additional chamber. Examples of chambers include a waste chamber 312, a sample processing chamber 314 and a catalyst chamber 316. Additional chambers may hold buffer solutions, washing solutions, suspensions of magnetic nanoparticles, developer solutions, enzymatic solutions including PCR reagents, dehydrated reagents and the like. In one embodiment, one chamber is reserved for use as an archive chamber wherein processed nucleic acid molecules may be stored for an extended period of time.

In the exemplary embodiment of FIG. 27, rotor 302 includes a column chamber 318. Column chamber 318 is formed by a first wall 320 and a second wall 322. In the embodiment depicted, second wall 322 is shorter than first wall 320. The column chamber 318 is fluidly connected to at least one port by an elongated channel that traverse at least a portion of the bottom panel or surface of the rotor 302. The column chamber 318 may be filled with a chromatography material, such as silica gel, that is suitable for column chromatography. Fluid may be pushed into the lower portion of column chamber 318 through the elongated channel. The fluid passes through the chromatography material and begins to fill column chamber 318. When the fluid reaches the high of second wall 322, the chromatographed fluid flows into overflow chamber 324 where it may be subsequently withdrawn via another port.

Figure 28A:
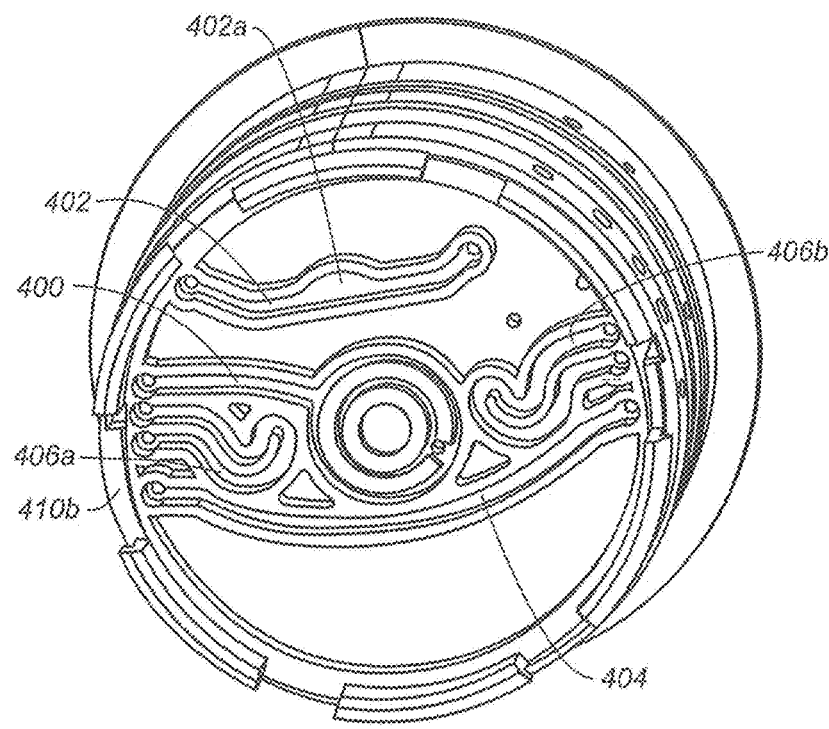
FIG. 28A is a bottom view of the exemplary disposable cartridge of FIG. 27.

FIG. 28A is a bottom view of rotor 302. FIG. 28A shows elongated channels that traverse at least a portion of the bottom panel of the rotor 302. Elongated channel 400 fluidly connects disrupting chamber 310 to a port (not shown) in the edge of rotor 302. Similarly, elongated channels 402, 404 and 406 also traverse at least a portion of the bottom panel. The elongated channels 402, 404 and 406 have a volume which is sufficient to function as chambers but the elongated channels 402, 404 and 406 extend parallel to the bottom surface of the rotor 302 and are therefore proximate the contact surface of the cartridge drive. Other elongated channels are also shown in FIG. 28A.

Figure 28B:
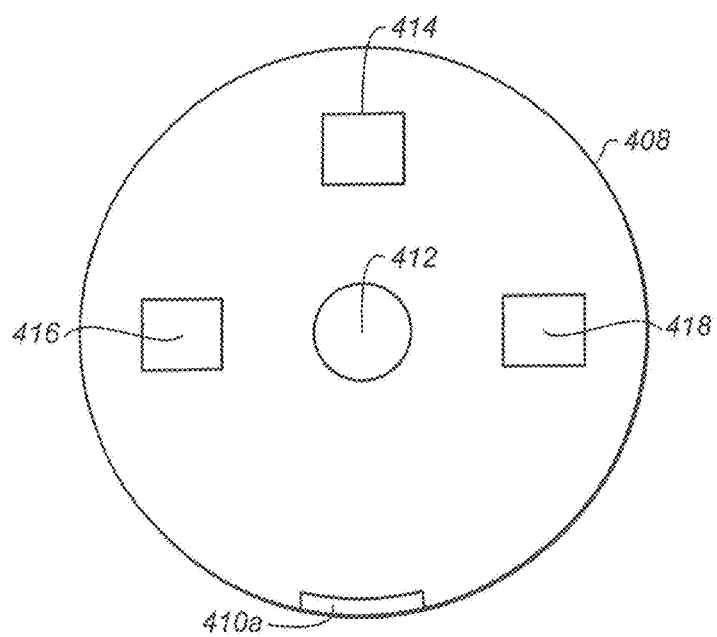
FIG. 28B, FIG. 29A and FIG. 29B are depictions of components that align with the bottom of the exemplary disposable cartridge.

FIG. 28B is a view of the contact surface 408 of the cartridge drive (not shown). The contact surface 408 and the rotor 302 have mated connectors 410a/410b which permit the contact surface 308 and the rotor 302 to become fixedly connected, thereby permitting rotation of the rotor 302 when the contact surface 408 is rotated. The contact surface 408 includes a disruptor 412, such as an ultrasonic disruptor, which is aligned with the disrupting chamber 310. Disposed beneath the rotatable contact surface 408 is magnet 414, first heater 416 and second heater 418. The magnet 414, first heater 416 and second heater 418 are fixedly mounted to the cartridge drive such that they do not rotate when contact surface 408 is rotated. Each is offset from the center of the rotor. Advantageously, this permits specific zones to be disposed near a magnetic field, a first heater or a second heater, simply by rotating the rotor 302.

Figure 29A:
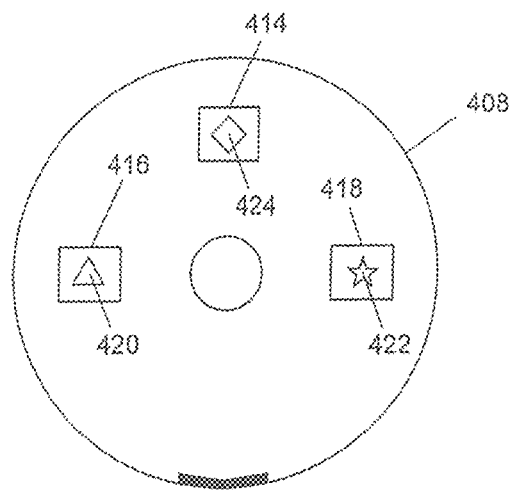
Figure 29B:
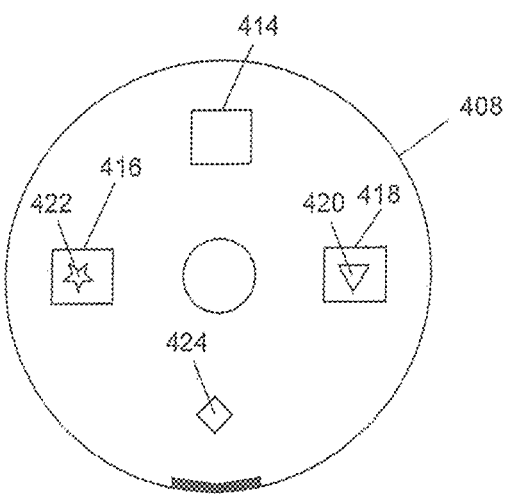

By way of illustration, the rotor 302 of FIG. 28A has a first zone 420, a second zone 422 and a third zone 424. The third zone 424 may be exposed to the magnetic field of magnetic 414 by rotating the rotor 302 into the rotary position shown in FIG. 29A. Conversely, the third zone 424 may be removed from the magnetic field of magnet 414 by rotating the rotor 302 into the rotary position shown in FIG. 29B, which is a 180 degree rotation. In another embodiment, the third zone 424 may be removed from the magnetic field of magnet 414 with a 90 degree rotation to also place the third zone 424 over one of the heaters, 416, 418.

In an analogous fashion, a sample may be introduced into elongated channel 404. Elongated channel 404 traverses both first zone 410 and second zone 422. The first zone 410 may be disposed over first heater 416 (e.g. to achieve a temperature of 50-55° C.) while the second zone 422 may be disposed over second heater 418 (e.g. to achieve a temperature of 90-95° C.) by adopting the rotary position shown in FIG. 29A. The relative positioning of the zones may be reversed by adopting the rotary position shown in FIG. 29B. This configuration is particularly advantageous when a PCR operation is conducted within one or more of the elongated channels. The high and low temperature cycling used in the PCR operation can be produced by rotating the rotor 302 to place the elongated channel over high and low temperature heaters. By repeatedly cycling the rotary positions, the sample within the elongated channels experiences multiple iterations of high and low temperatures.

Figure 30:
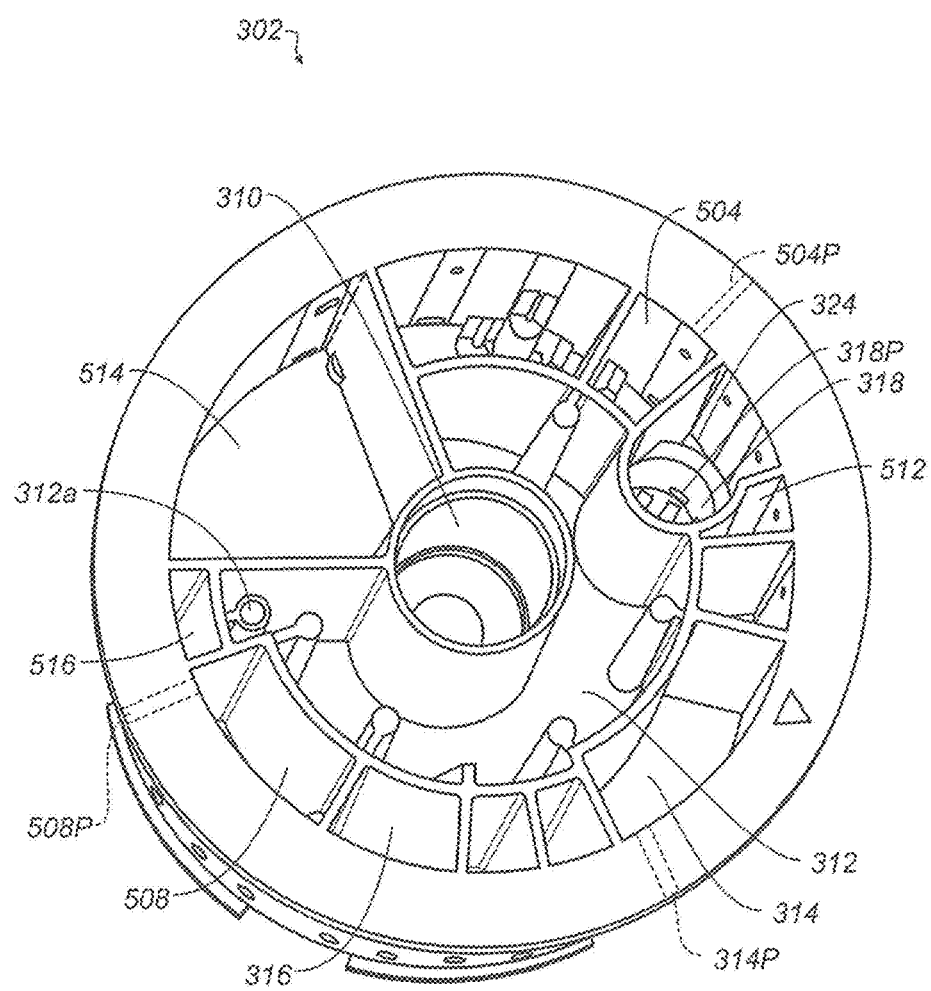
FIG. 30 is an alternate top perspective view of an exemplary disposable cartridge.

In operation, and with reference to FIG. 30, a biological sample is disposed in disrupting chamber 310 of rotor 302. The rotor 302 is rotated to align port 504P with the plunger (not shown). The plunger is activated to withdraw a lysis buffer solution from chamber 504. The rotor 302 is then rotated to align a port with the plunger that is in fluid communication with the disrupting chamber 310. In the embodiment of FIG. 30, the fluid communication is established through elongated channel 400 (see FIG. 28A). The plunger is activated to inject the lysis buffer into the disrupting chamber 310. Ultrasonic force is applied from disruptor 112 to disrupt the biological sample and release the nucleic acids. In one embodiment, a size stabilizer is present to control the size of the fragments produced during the disruption step.

The rotor 302 is then rotated to align the plunger with the port that is in fluid communication with disrupting chamber 310. The port may include an in-line filter, such as a 0.8 micron filter. The plunger is activated to withdrawn the solution from disrupting chamber 310 and simultaneously pass the solution through the filter.

The rotor 302 is then rotated to align port 314P with the plunger. The plunger is activated to inject the solution into processing chamber 314. Processing chamber 314 includes a suspension of magnetic nanoparticles. The solution is exposed to the magnetic nanoparticles for a period of time that is sufficient to allow the nucleic acids to bind to the magnetic nanoparticles. The plunger is thereafter activated to withdraw the suspension of magnetic nanoparticles from processing chamber 314.

The rotor 302 is then rotated to align the plunger with a port that is in fluid communication with elongated chamber 402. The plunger is activated to inject the suspension of magnetic nanoparticles into elongated chamber 402. The elongated chamber 402 traverses at least a portion of a bottom panel of the rotor 302. The elongated chamber 402 is disposed proximate to a magnet, such as magnet 414. This magnet causes the magnetic nanoparticles and the nucleic acids bound thereto, to become concentrated in a particular area within the elongated chamber 402. Advantageously, this holds the magnetic nanoparticles in place while allowing unbound material to be rinsed away. In one embodiment, elongated chamber 402 includes a wide region 402 whose diameter is wider than the diameter of the other portions of elongated chamber 402. When the magnetic field is applied, the nanoparticles concentrate in wide region 402 without clogging the elongated chamber 402, thereby permitting wash solutions to pass over the concentrated nanoparticles.

Wash solutions for washing the magnetic nanoparticles may be withdrawn from other chambers. In one embodiment, the rotor 302 is rotated to align port 508P with the plunger. The plunger is activated to withdraw a wash solution from chamber 508. Examples of suitable wash solutions include water, ethanol, 70% ethanol, buffered solutions, and the like. The rotor 302 is rotated to re-align the plunger with the port that is connected to elongated chamber 402. The plunger is activated to inject the wash solution into the elongated chamber 402. As the wash solution passes over the magnetic nanoparticles, excess liquid passes through elongated chamber 402, out hole 312A and into chamber 312. In the embodiment of FIG. 30, chamber 312 is a waste chamber. This wash step may be repeated as desired.

As a further advantage of the rotary approach, the rotation of the rotor 302 to withdraw the wash solution also moves the elongated chamber 402 away from the magnet. This permits the magnetic nanoparticles to become re-suspended which facilitates the removal of unbound material that could have been caught between clumping nanoparticles. When the rotor 302 is rotated into position to inject the wash solution into the elongated chamber 402 then the elongated chamber 402 is once again proximate the magnet.

In one embodiment, the final wash is a release solution configured to release the nucleic acids from the magnetic nanoparticles. After the release solution has been allowed to contact the magnetic nanoparticles for a sufficient period of time, the plunger is activated to withdraw the release solution and the dissolved nucleic acids. In one embodiment, the release solution is heated to promote release of the nucleic acid molecules using a heater in the cartridge drive.

The rotor 302 is rotated to align the plunger with a port that is in fluid communication with column chamber 318. When the plunger is activated, the solution is injected into of column chamber 318. The solution passes through a gel within the column chamber 318 and accumulates in overflow chamber 324 of the column chamber 318. The gel may be any suitable porous material, such as silica, that is useful for cleaning the solution. For example, column chamber 318 may be used to remove the nanoparticles or desalt the solution. The gel within column chamber 318 may initially be in a dehydrated state. Prior to the injection of the nucleic acid solution, water, buffers, or other solutions may be withdrawn from other chambers and injected into column chamber 318 through port 318P to hydrate the gel. Residual material may be washed out of the column chamber 318 and into overflow chamber 324 by withdrawing a wash solution from another chamber and passing the wash solution through the gel.

After the nanoparticles have been removed, the fee nucleic acids may be subjected to PCR. In one embodiment, PCR reagents are stored in a dehydrated state. Like the gel of column chamber 318, water, buffers, or other solutions may be withdrawn from other chambers and injected into the chamber which holds the PCR reagents to hydrate the reagents. For example, dehydrated PCR reagents may be stored in chamber 512 and water may be stored in chamber 514. By rotating the rotor 302 and operating the plunger, water is withdrawn from chamber 514, injected into chamber 512. The hydrated PCR reagents are then combined with the nucleic acid solution by, for example, injecting the nucleic acid solution into chamber 512. The combined solution is then injected into elongated chamber 404 (see FIG. 28A) that traverses at least a portion of a bottom panel of the rotor 302. The elongated chamber 404 is configured to run a PCR process to amplify the concentration of nucleic acids. In another embodiment, half the combined solution is injected into elongated chamber 406a and the other half of the solution is injected into elongated chamber 406b.

Elongated chamber 404 is similar to elongated chamber 402 described elsewhere in this specification. The elongated chamber includes two zones that are sufficiently distant from one another such that each zone can be placed over two different heaters that are at two different temperatures. A high temperature heater may be held at an elevated temperature (e.g. 90-95° C.) to break the hydrogen bonds in the nucleic acid sample that is disposed proximate that zone. However, these temperatures are too high for the PRC reagents to function. The low temperature heater may be held at an elevated temperature (e.g. 50-55° C.) that is below the high temperature heater but is above room temperature. These temperatures are too low to break the hydrogen bonds in the nucleic acid sample. However, these temperature are sufficient for the PRC reagents to function. By rotating the rotor 302, the two ends of the elongated chamber 404 can be sequentially sent through multiple high/low temperature cycles. For example, this cycle may be repeated about thirty times.

In some embodiments, the nucleic acids are removed from the disposable cartridge and provided to external equipment for subsequent processing. In certain of these embodiments, the nucleic acids are stored in archiving chamber 516 until they are ready to be removed from the disposable cartridge.

In other embodiments, the nucleic acids remain within the disposable cartridge and are subjected to subsequent detection techniques to identify the presence of absence of a target analyte. In such an embodiment, the amplified solution is withdrawn from the elongated channel 402 and subsequently aligned with a port that is in fluid communication with a reaction chamber, such as reaction chamber 142. The plunger is activated and the amplified solution is injected into reaction chamber 142. The reaction chamber 142 comprises a chip for detecting the presence of particular nucleic acid sequences. Exemplary chips are disclosed in U.S. Pat. No. 6,399,303. The catalyst solutions, washing solutions and developer solutions necessary to permit the chip to detect the particular nucleic acid sequence are stored in other chambers. These chambers are accessed in the same rotary fashion as the other chambers.

Figure 31A:
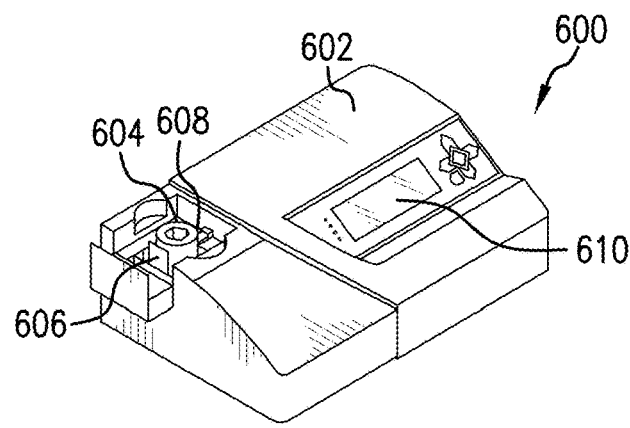
FIG. 31A, FIG. 31B and FIG. 31C are exemplary systems for preparing a nucleic acid sample.

System for Preparing Nucleic Acid Samples:

Referring to FIG. 31A a system for preparing a nucleic acid sample is shown. The system 600 comprises a detection device 602 and a disposable cartridge 604. The disposable cartridge 604 removably attaches to a cartridge drive 606 which is configured to rotate a rotor that is rotatably connected to the disposable cartridge 604. When the disposable cartridge 604 is properly positioned within detection device 602 a plunger, which is operated by a plunger driver, aligns with syringe mold 608. Additionally, a chip on disposable cartridge 604 electrically connects to a chip receptacle in the detection device 602. This chip receptacle places the chip in electrical communication with a microprocessor in the detection device 602 such that electrical signals from the chip can be processed to detect the presence of a target analyte. Data may be stored on data storage media in the detection device 602. Examples of data storage media include hard drives, flash memory drives, and the like.

In one embodiment the disposable cartridge 604 includes a barcode label that encodes the specific disposable cartridge with identifying information. This information includes, for example, information concerning the identification of the chip on that particular disposable cartridge. Manufacturing information, such as manufacturing location, lot number, and the like may also be included. In one embodiment, a unique identifier is provided in the barcode that permits the disposable cartridge to be specifically correlated with a particular test (e.g. test for disease X, on date Y for patient Z). The barcode may be a one-dimensional or two-dimensional barcode.

The detection device 602 may comprise a barcode scanner positioned to read the barcode on the disposable cartridge 604. This information may be used by the microprocessor. For example, the barcode scanner may read a barcode on a particular disposable cartridge and determine this disposable cartridge is for testing for condition X. The detection device 602 may display on screen 610 a message asking the user to confirm condition X is the intended test. Additionally or alternatively, the detection device may detect that this particular disposable cartridge has already been used by querying a database for the unique identifier associated with that disposable cartridge. In some embodiments, the previous test results are then loaded.

Figure 31B:
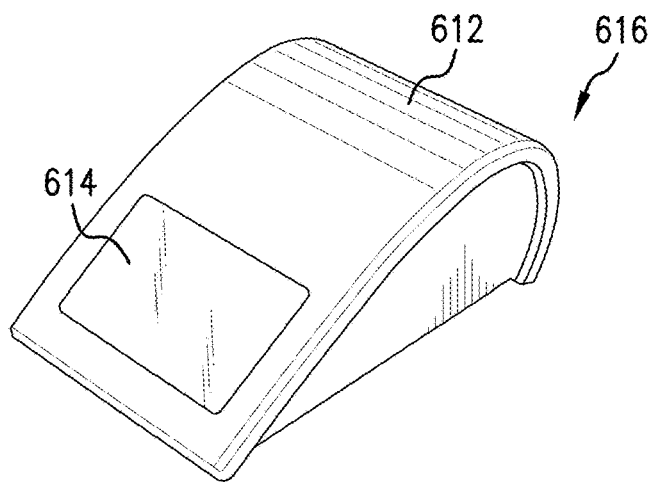
Figure 31C:
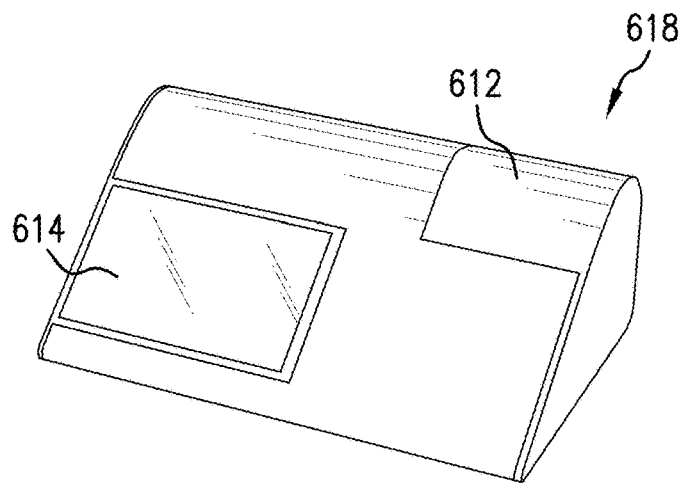

In the embodiments of FIG. 31B and FIG. 31C, two portable detection devices 616, 618 are shown. The portable detection devices are sized to permit an individual to transport the device into, for example, a field condition. Such a portable detection devices are particularly useful in remote locations and find particular utility in military applications. A lid 612 opens to reveal a cartridge drive for receiving a disposable cartridge. A touch screen 614 provides a display and a user-interface. In other embodiments, a keyboard or button control is provided as a user-interface.

Figure 32:
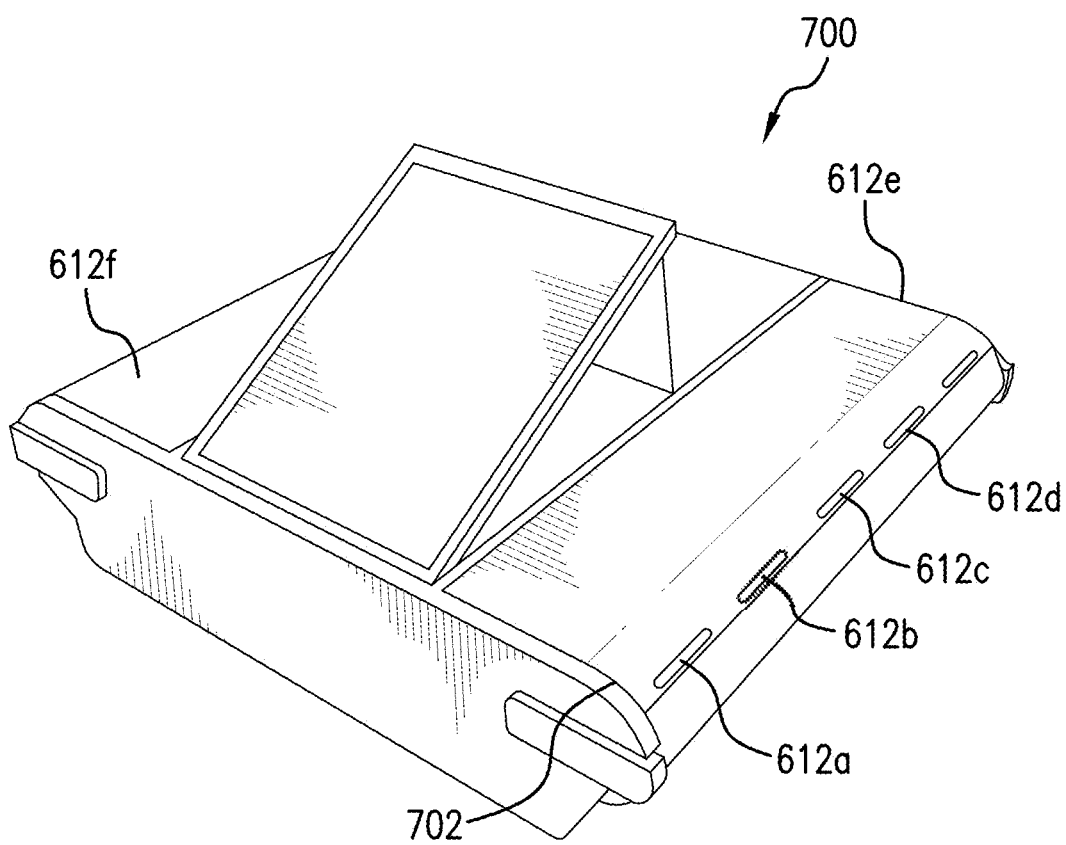
FIG. 32 is an exemplary systems for preparing a nucleic acid sample.

In the embodiment of FIG. 32 a bench-top detection device 700 is shown. The single detection device is configured to receive multiple disposable cartridges, each under a lid 612a-f. A light 702 is provided for each lid that indicates when a test is completed and the receptacle is ready for use. For example, a red light may indicate the chamber is in use while a green light indicates the test is complete.

In one embodiment, the detection device, such as detection device 600, 616, 618, or 700, can be connected to a computer network. In one such embodiment, this connection is a wireless connection. The data obtained may be transmitted over the computer network to a server for subsequent processing. For example, the data obtained, including the positive or negative detection of the analyte, the unique identifier of the disposable cartridge, the date and time, as well as other pertinent information, may be sent to a server. In one embodiment, the detection device is equipped with a global positioning system (GPS) and the geographic location of the detection device is transmitted as well. Advantageously, this permits a server to compile data from one or more detection devices and analyze the data as a function of both time and geography. This feature is particularly useful when used in conjunction with field detection devices such as 616 and 618. Since this information can be transmitted with no user intervention, compliance with data transmission protocols is increased. In certain embodiment, the data is stored in the data storage media until such time as the detection device can successful connect to the network. When a successful connection is established, the accumulated data is sent to the server.

Sample Types Processed

Numerous types of biological samples can be processed. The sample preparation process is suitable for use on liquids, solids, soil samples, animal tissue, insect carcasses, DNA, bacterial cells, spores and viruses. Biological samples include all biological organisms which contain nucleic acids. Including but not limited to bacteria, spores, blood, tissues, fungi, plants and insects. As shown in FIG. 35, several disparate samples were processed using identical parameters. Samples of purified DNA, bacterial cells, spores, viruses and fruit flies were all treated using the following technique: each sample was subjected to sonication treatment for two minutes in the presence of magnetic nanoparticles and 100 micron glass beads. As shown in FIG. 35, all sample types provided a similar fragment distribution.

As a variety of types of biological samples can be used, a single system can be used with a wide variety of target organisms without the need to modify the preparation process. Furthermore, even if a sample contains two different targets, nucleic acid molecules can be purified from both components. For example, standard procedures may not work with a sample containing both a virus and a spore—either the parameters must be set to efficiently lyse the spores, in which case viral material is lost, or set to maximize the viral sample, in which case the spores are not lysed. Thus the benefits of the inclusion of a size stabilizer is evident.

By utilizing a single sample preparation technique the potential for false negatives is reduced. As the size stabilizer limits the range of base pair lengths for the nucleic acid molecules, the potential for material loss due to over-sonication is decreased. In one embodiment, the sample preparation system works with small quantities and produces a narrow distribution of nucleic acid molecule fragments. In one embodiment, the preparation system passes sample through steps that filter the sample prior to applying a shear force.

Sample Disruption

In one embodiment the mechanical force used to release the nucleic acid molecules is sonic vibration accomplished by contacting a container of the fragments suspended in protective buffer with source of sonic vibrations. Such a source may be a commercial ultrasonic transducer or a piezo electric crystal activated by an AC voltage. Such devices are well known to those skilled in the art. Shearing frequencies can be from 10,000 Hz to 10 MHz. In one embodiment, the frequency is between 20 KHz and 4 MHz. In another embodiment, the frequency is between 20 KHz and 40 KHz. To assist the shearing of protected nucleic acid molecules samples such as, for example, spores, small beads may be added to the sample. The sonic induced movement of the beads breaks the spore walls to release the nucleic acid molecules contained within. The beads may range in size from about 1 micron to about 1 mm. In one embodiment, the size is between about 10 microns to about 500 microns. In another embodiment, the size is between about 50 microns to about 200 microns. The beads may be a metal such as stainless steel, glass or a dense metallic oxide such as zirconium oxide. The time required for shearing the nucleic acid molecules depends partly on the size of the sample and power transmitted from the transducer to the sample. However, when the sheared sample reaches a steady state, which depends on the composition of the protective buffer, there is no further change in the nucleic acid molecules size distribution with further sonication. In practice, sonication times of 15 seconds to 2 minutes at a power level of 1 to 2 watts with a sample size of 100 μL of buffer containing 1 microgram of nucleic acid molecules are sufficient to reach a steady state.

In one embodiment, disrupting beads such as glass beads of about 100 microns in diameter are used to disrupt a sample and release nucleic acid molecules. The beads are vibrated using an ultrasonic source to generate a shearing force on the sample. In one embodiment, for sample suspensions from about 0.1 ml to 0.5 ml of water, containing from about 0.1% to 1% nucleic acid, an ultrasonic power level of about 3 to 7 watts is used for a period of from about 1 to 3 minutes. The volume of glass beads used in the sample is, in one embodiment, between about 10% to 50% of the volume of the total suspension. The ultrasonic frequency used to agitate the glass beads is conventionally 20 KHz, from a commercial device such as the Branson Sonifier 150. It is understood that frequencies from about 10 KHz to 100 KHz could be suitable depending on the sample parameters. In another embodiment, the shearing force is applied by a nebulizer or a homogenizer.

Figure 40:
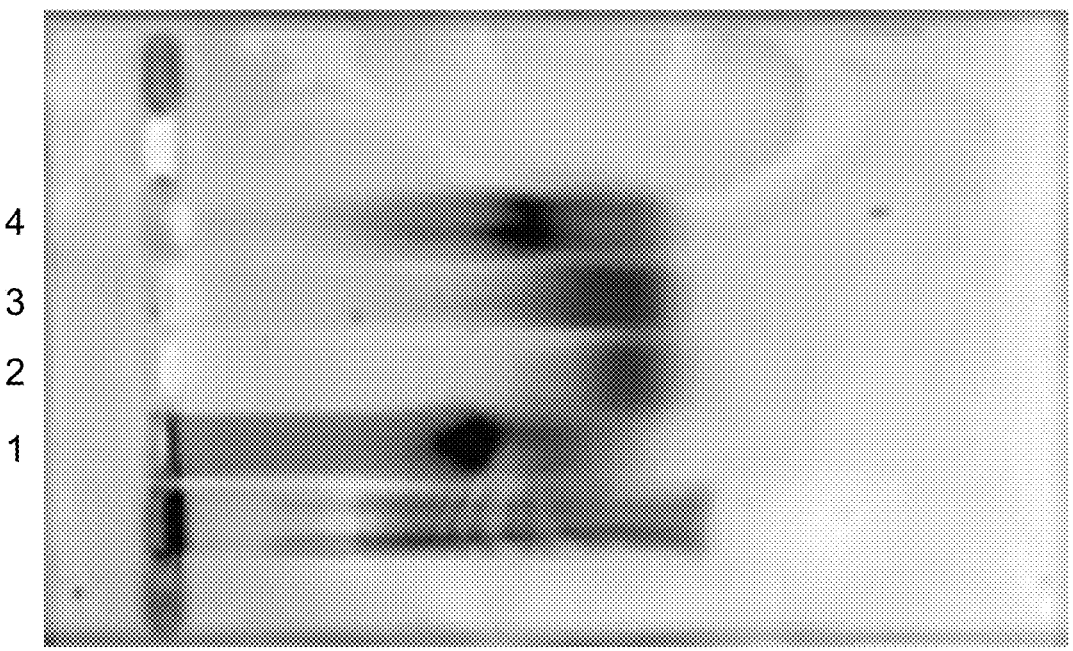
FIG. 40 demonstrates DNA recovered from fruit flies using various buffers.

FIG. 40 demonstrates the effective release of nucleic acid molecules from spore samples. To determine efficiency of spore lysis, the maximum amount of nucleic acid output expected from the spores was estimated and compared to the amount measured on the gel in FIG. 40. Utilizing this technique, the method provided an estimate of 85-90% efficiency. Alternatively, spore lysis efficiency can be measured by determining spore survival after sonication. As shown in Table 1, based upon survival assays, the efficiency after two minutes of sonication during experiments was 86% of spores were opened.

Efficiency of Spore Lysis as Determined by Spore Survival (Spore Basis)

TABLE 1

| Sonication time | # spores survived | % efficiency |
|---|---|---|
| No sonication | 235 | |
| 30 sec. | 105 | 55% |
| 1 min. | 61 | 74% |
| 2 min. | 32 | 86% |

For mechanical shearing such as bead disruption to be used as a universal sample preparation approach, it is necessary to characterize and optimize operating parameters with respect to different target material (DNA, RNA or protein) and their source (environmental, blood, or tissue). Although a single system is suitable for disruption different sample types, to optimize results parameters such as power input and the duration of applying sonic agitation may vary with respect to different cell types. Furthermore, it is understood that the concentration of the size stabilizer, the size of the glass beads and the inclusion of enzymes such as collagenase and hyaluronase are all further embodiments of the invention and are no way limiting.

It is understood that magnetic nanoparticles, glass beads or a combination of both can be used for disruption without departing from the invention. In one embodiment the magnetic nanoparticles are formed of iron oxides. In one embodiment the magnetic nanoparticles are in the 40-200 nm size range. The magnetic nanoparticles can be accelerated using an ultrasonic force and can shred the sample. In one embodiment, glass beads are used in the extraction mixture for efficient lysis of spores.

In another embodiment, the sample preparation process further includes the addition of RNase inhibitors to prevent sample degradation. In one embodiment, the sample preparation process includes diethylpyrocarbonate (DEPC), ethylene diamine tetraacetic acid (EDTA), proteinase K, or a combination thereof.

Size Stabilizers

In one embodiment, a buffer is mixed with the biological sample during the disruption step. To retain the desired sample size the buffer serves as a size stabilizer. The size stabilizer is a water solution which may contain salts, detergents, co-solvents or polymers. The size stabilizer prevents the subsequent shearing step from producing fragments of nucleic acid molecules that are too small to be useful in operations such as hybridization, sequencing and polymerase chain reaction (PCR) amplification. For hybridization, fragments of nucleic acid molecules that are smaller than about 18 base pairs lose specificity and are unstable at ambient temperatures. For genetic sequencing and PCR applications, nucleic acid molecule fragments from about 200 to about 500 base pairs are desirable. Use of a pure water buffer gives nucleic acid molecule fragments less than about 100 base pairs, which are too small for many applications.

The addition of size stabilizers in the sample preparation of this invention results in a high yield of nucleic acids of limited size range. The size stabilizers of this invention include detergents, surfactants and soaps. Examples of suitable stabilizers include anionic surfactants, sodium dodecylsulfate, and sodium dodecylbenzenesulfonate. The size stabilizer is present in the sonicated suspension in an amount between about 0.1% and 10%. In another embodiment, the size stabilizers is present in an amount between about 0.2% and 2%. In yet another embodiment, the size stabilizers is present an amount between about 0.5 and 1.5%.

Use of the size stabilizer allows the gathering of nucleic acid molecule fragments in a desired base pair range. In traditional bead beating processes the mechanical shearing force is turned off after a particular time to maximize the amount of nucleic acid molecule fragments in the desired base pair range. However, because the process is time sensitive a large range of base pair lengths remain present in the sample. By utilizing a size stabilizer the base pair length of most of the sample can be fragmented to the desired base pair range. In one embodiment, at least 60% of the nucleic acid molecule fragments are within 50% of the length of the median nucleic acid molecule fragment base pair length in the sample. Said another way, if the median nucleic acid molecule fragment has 400 base pairs, 60% of the sample would have between 200 and 600 base pairs. In another embodiment, at least 75% of the nucleic acid molecule fragments are within 50% of the length of the median nucleic acid molecule fragment base pair length in the sample. In yet another embodiment, at least 75% of the nucleic acid molecule fragments are within 30% of the length of the median nucleic acid molecule fragment base pair length in the sample.

Figure 42:
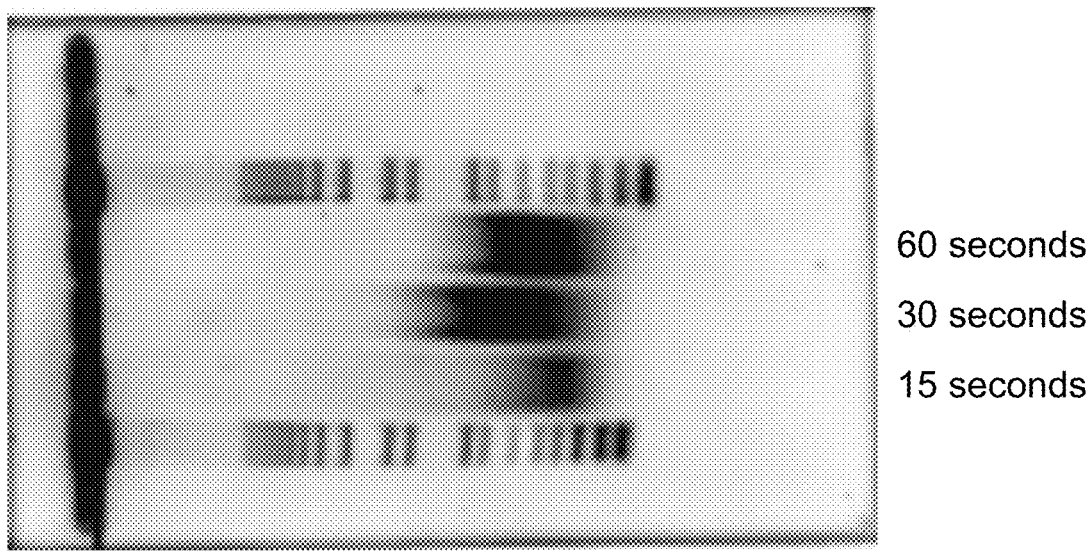
FIG. 42 demonstrates the recovery of nucleic acid molecules from *E. coli* showing longer sonication times do not change the size distribution.

Without a size stabilizer present, the nucleic acid molecules tend to degrade when applying a mechanical force such as sonication. The ultrasonic bead beating with a size stabilizer present shears the nucleic acid molecules into short fragments that are less than 100 bases long (See FIG. 34, lanes 5 and 6). For most applications, fragments need to be larger than 100 bases. As shown in FIG. 42, a series of tests were performed to sonicate purified DNA and RNA sheared polymers to no smaller than 400 bases, even under lengthy sonication times. In complex samples, nucleic acid molecules stick to membranes and proteins while continuing to break down to smaller fragments. To overcome this problem, the lysis buffer is modified to contain a size stabilizer such as a detergent like sodium dodecyl sulfate (SDS). As shown in FIG. 34, the addition of the size stabilizer shown in lanes 3 and 4 protects the nucleic acid molecules from over shearing. The samples without the size stabilizer were sheared to well below 100 bases, as shown in lanes 5 and 6.

The size stabilizer is contained in a protective buffer solution. It is understood that the protective buffer may contain numerous size stabilizers to achieve the desired base pair range. Salts which may be used in the protective buffer include, sodium phosphate, guanidinium hydrochloride and dextran sulfate. The protective buffer may further contain detergents such as sodium dodecyl sulfate, sodium dodceyl benzene sulfate, and polyethyleneglycol. Many commercial anionic surfactants such as ALKANOL® XC may also be used. In another embodiment the protective buffer includes co-solvents. Co-solvents include dipole aprotic solvents such as dimethylsulfoxide, dimethyl formamide, dimethyl acetamide, hexamethyl phosphoramide and tetramethylurea. In another embodiment the protective solution contains polymers such as poly vinyl alcohol, polyethylenimine, poly acrylic acid and other polymeric acids. The concentration of the salts, detergents, co-solvents and polymers may range from 10 mM to 5M. In one embodiment, the concentration is between about 100 mM to about 1M. Other size stabilizers of this invention include chaotropic salts such as guanadium thiocyanate. Such salts are known to disrupt the normal folding of proteins associated with nucleic acids, thereby releasing the nucleic acids in free form.

In another embodiment, the presence of a size stabilizer also stabilizes RNA. The SDS and guandinium thiocyanate disrupt the RNAses in the sample thus preserving the RNA.

Cleaning of Fragmented Nucleic Acids

In one embodiment, the process further comprises the steps necessary to clean the nucleic acid molecules. After release of the nucleic acid molecules and shearing to a useful size range, it is advantageous to clean the nucleic acid molecules from cell debris, proteins, sonication beads and the protection buffer to provide a purified nucleic acid molecule solution in a buffer compatible with subsequent nucleic acid molecule operations and procedures.

In one embodiment, additional rinse steps are used to purify the sample. The rinsing removes compounds which could inhibit binding of nucleic acid molecules. Suitable rinse solutions include, but are not limited to alcohol solutions such as ethanol. The sample can be washed with additional precipitation buffer, or a washing buffer that does not disturb the complex. After washing, the buffer is drained from the sample resulting in a purified, concentrated sample.

In one embodiment, the nucleic acid molecules are cleaned by magnetically separating them from the reminder of the sample. The nucleic acid molecules bind to magnetic nanoparticles. In one embodiment, the binding occurs in a high salt/alcohol condition and the nucleic acid molecules are eluted using a low salt chelating buffer such as sodium citrate at increased temperature. In one embodiment the sample is heated to at least 60° C. to increase the yield from elution.

Once the magnetic nanoparticles are attached to the nucleic acids a magnetic field is applied to the reaction chamber. The application of the magnetic field causes the magnetic nanoparticles and any attached target analytes to concentrate in one portion of the reaction chamber. The sample is pulled from the concentrated region of the sample chamber providing a large amount of target analytes compared to the amount of volume extracted. By concentrating the sample more sensitive tests can be preformed.

In another embodiment, the magnetic field holds the magnetic nanoparticle steady as the remaining sample is removed from the chamber. The binding force between the magnetic nanoparticle and the target analyte is sufficient to prevent the target analyte from being removed. A magnet is utilized to generate an magnetic field. The magnet can pull or push magnetic nanoparticles. The magnet can concentrate a sample of magnetic nanoparticles or speed up the diffusion process by guiding any magnetic nanoparticles.

In one embodiment, magnetic nanoparticles are located in a sample chamber along with a target analyte. The magnetic nanoparticles have an affinity for the target analyte. By attaching the magnetic nanoparticles to the target analyte and applying a magnetic field the target analyte is manipulated to desired locations within the sample chamber.

In one embodiment, a precipitation buffer is in solution with the target analyte fragments and the magnetic nanoparticle. The precipitation buffer precipitates the target analyte out of solution and the target analyte is drawn to the magnetic nanoparticles. The precipitation buffer can be any buffer that precipitates the target analyte from the solution. For proteins, examples of suitable precipitation buffers include, but are not limited to organic precipitants such as, ammonium sulfate, trichloroacetic acid, acetone, or a mixture of chloroform and methanol. For nucleic acid molecules suitable precipitation buffers include, but are not limited to, water miscible organic solvents, acetone, dioxane and tetrahydrofuran. While examples of precipitation buffers are provided, it is understood that any suitable precipitation buffer can be utilized without deflecting from this claimed invention.

In one embodiment a dispersion of magnetic nanoparticles is added to the sample. The mixture is then incubated at about 60° C. to facilitate the binding. A precipitation buffer is then added to the mixture. The bound complex of nucleic acid molecules and magnetite is then collected in a magnetic field. In one embodiment, the complex is collected on a side wall of the container so any unbound solids can fall to the bottom of the container for easy removal. The buffer and any unbound solids are then removed from the sample.

For further processing of the nucleic acid molecules, for some processes, it is necessary to remove the magnetite nanoparticles. In one embodiment the nucleic acid molecule is eluted from the complex of nucleic acid molecules and magnetite by heating a mixture of an elution buffer and the complex to 95° C. The magnetite can be collected by a magnetic field, or by centrifugation, providing purified nucleic acid molecules in elution buffer. In one embodiment the elution buffers contain a salt which interacts strongly with iron oxide surfaces. In one embodiment, the buffers are selected from phosphate and citrate salt solutions.

In another embodiment, the magnetic nanoparticles contain superparamagnetic nanoparticles. The superparamagnetic nanoparticles include metal oxides, such as iron oxides. In one embodiment the magnetic nanoparticle is a magnetite nanoparticle ($Fe_3O_4$). Magnetite particles are common in nature, and can be collected from beach sands at the edge of the ocean by screening with a magnet. Grinding these particles will produce a relatively coarse magnetic powder. Smaller sized particles can be produced by adding a solution of mixed ferric and ferrous chloride to a stirred aqueous alkaline solution of sodium or ammonium hydroxide. Even smaller sized particles are produced by thermal decomposition of iron acetonylacetonate in dibenzyl ether in the presence of hexadecanediol, oleyl amine and oleic acid. Numerous methods for making magnetite are known. For example, Sun et al. discloses slowly adding a mixture of ferric and ferrous chloride into stirred ammonia. *Langmuir*, 2009, 25 (10), pp 5969-5973. U.S. Pat. No. 4,698,302 teaches mixing ferrous and ferric chloride with sodium hydroxide. Samanta et al, discloses adding ammonia to a stirred mixture of ferric and ferrous chloride in an inert atmosphere. Journal of Materials Chemistry, 2008, 18, 1204-1208. Duan et al. teaches dissolving iron oxide in oleic acid to form a complex that forms magnetite nanoparticles when heated to 300 degrees C. *J. Phys*. nucleic acid molecule *Chem. C*, 2008, 112 (22), pp 8127-8131. Additionally, Yin et al. discloses thermally decomposing iron pentacarbonyl in the presence of oleic acid, *Journal of Materials Research*, 2004, 19, 1208-1215.

Suitable binding buffers may be added to the solution. Binding buffers for the nucleic acid molecule/magnetite complex are, for the most part, buffers in which nucleic acid molecules are insoluble. Precipitation of the nucleic acid molecules promotes binding of the nucleic acid molecules to the magnetite nanoparticles. The binding buffer for nucleic acid molecules and magnetite nanoparticles may contain water, sodium acetate, sodium chloride, lithium chloride, ammonium acetate, magnesium chloride, ethanol, propanol, butanol, glycogen or other sugars, polyacrylamide or mixtures thereof. In one embodiment the binding buffer is isopropanol.

Binding of the nucleic acid molecules to the magnetite nanoparticles is not instantaneous. In one embodiment the mixture is incubated above room temperature to speed the binding process.

Magnetic Manipulation:

In one embodiment, a magnet 114 is utilized to generate an electric field. The magnet can pull or push magnetic nanoparticles in the rotor. The magnet 114 can concentrate a sample of magnetic nanoparticles or speed up the diffusion process by guiding any magnetic nanoparticles.

Magnetic nanoparticles are located in a sample chamber along with a target analyte (e.g. a target nucleic acid). The magnetic nanoparticles have an affinity for the target analyte. By attaching the magnetic nanoparticles to the target analyte and applying a magnetic field the target analyte is manipulated to desired locations within the sample chamber.

In one embodiment, the target analyte binding element is attached to the magnetic nanoparticle via at least one intermediate connecting group such as, but not limited to linkers, scaffolds, stabilizers or steric stabilizers.

The magnetic nanoparticles exhibit magnetic properties. In one embodiment cobalt, nickel, iron or a combination thereof is used to create a magnetic nanoparticle. In one embodiment, the magnetic nanoparticle further contains a catalytic particle. In one embodiment the catalytic particle is palladium, platinum, silver or gold.

In one form, a nickel-palladium nanoparticle, stabilized by a surface layer of 4-dimethylaminopyridine as described in Flanagan et al, *Langmuir*, 2007, 23, 12508-12520, is treated by adsorption with a plurality of ethidium bromide intercalator molecules to create nucleic acid binding sites. The ethidium moiety bonds to the nucleic acid polymer thereby attaching the nickel-palladium nanoparticle to the nucleic acid polymer.

In another form, a simple straight-chain scaffold molecule, such as oligoethylene glycol (PEG), is affixed with a nucleic acid binding element at one end and a linker at the other end. The nucleic acid binding element binds to the nucleic acid polymer and the linker binds to the magnetic nanoparticle. The nucleic acid binding element is an intercalator, such as ethidium bromide, or a minor groove binder such as distamycin. The linker is a phenanthroline derivative. Hainfeld, *J. Structural Biology*, 127, 177-184 (1999) reports the advantage of phenanthroline derivatives in creating palladium particles. The scaffold may be a simple difunctional straight chain as shown, or may be a multifunctional branched scaffold connecting multiple magnetic nanoparticles or nucleic acid binding elements. The nucleic acid binding element bonds to the nucleic acid polymer, thereby attaching the nanoparticle to the nucleic acid polymer. It is understood that additional nucleic acid binding elements and intermediate connecting groups are within the scope and may be used.

Concentration of Target Analyte:

The sample containing the target analyte is located in a reaction chamber. The reaction chamber contains both the sample and magnetic nanoparticles. The magnetic nanoparticles bind to the target analyte. In one embodiment the reaction chamber further contains disrupting beads to assist in breaking apart samples to provide access to the target analyte.

Once the nucleic acid molecules have been released, the nucleic acid molecules can be magnetically separated from the reminder of the sample. The nucleic acid molecules bind to magnetic nanoparticles. In one embodiment, the binding occurs in a high salt/alcohol condition to form a complex. The complex is eluted using a low salt chelating buffer such as sodium citrate with increased temperature. In one embodiment the complex is heated to at least 95° C. to increase the yield from elution.

Once the magnetic nanoparticles are attached to the target analyte a magnetic field is applied to the reaction chamber. The application of the magnetic field causes the magnetic nanoparticles and any attached target analytes to concentrate in one portion of the reaction chamber. The sample is pulled from the concentrated region of the sample chamber providing a large amount of target analytes comparative the amount of volume extracted. By concentrating the sample more sensitive tests can be preformed.

In another embodiment, the magnetic field holds the magnetic nanoparticle steady as the remaining sample is removed from the chamber. The binding force between the magnetic nanoparticle and the target analyte is sufficient to prevent the target analyte from being removed. In some embodiments, additional rinse steps are used to purify the sample.

Rapid Movement and Increased Sensitivity:

Typically in solution a target analyte is limited in movement by fluid flow and diffusion rates. To speed the movement of a target analyte through the system a magnetic field is applied to progress the magnetic nanoparticle to the desired location. The application of the magnetic field allows for rapid transport of the target analyte from one chamber to another.

An array of sensors are used to rapidly detect the target analyte. A magnetic field is applied to guide the magnetic nanoparticles and attached analytes to the vicinity of a first sensor. A distinct magnetic field then guides the magnetic nanoparticles and any attached target analytes to a second sensor. The magnetic field is manipulated to move the target analytes to each sensor in the array. In one embodiment, the sensor binds a particular target analyte with enough force to prevent the magnetic field from breaking the bond. By systematically applying magnetic fields the analysis time is greatly reduced compared to normal diffusion analysis.

Magnetic Nanoparticles:

Use of sols or clusters in the form of magnetic nanoparticles allows for the attachment of magnetic material to a target nucleic acid polymer or other target analyte. By applying a magnetic field to the sample the nucleic acid polymer can be manipulated via the attached paramagnet material.

The paramagnet nanoparticles are formed in solution with a stabilizer. In one embodiment a metal salt is used. A reducing agent, such as dimethylamineborane or sodium borohydride, is added to the solution. If needed, solvents and excess salts can be removed by centrifugation, decantation, washing, and resuspension of the metal clusters. Alternatively, a magnetic field can be applied to the solution holding the magnetic nanoparticles in place as a drain and rinse is applied.

Target Analyte Binding Element:

The target analyte binding element attaches to the magnetic nanoparticle, either directly or by way of an intermediate connecting group. The target analyte binding element further binds to the nucleic acid polymer. In one embodiment the target analyte binding element is a nucleic acid binding element such as a molecule, fragment or functional group that binds to nucleic acid polymers. Potential nucleic acid binding elements comprise intercalators, minor groove binders, cations, amine reactive groups such as aldehydes and alkylating agents, proteins, and association with hydrophobic groups of surfactants. In addition, functional groups such as aldehydes are used to create a connection by reaction with free amines in the nucleic acid. Other amine reactive groups such as electrophiles for use in Michael addition reactions are suitable.

Examples of structures that form the basis for intercalating and minor groove binder structures are:

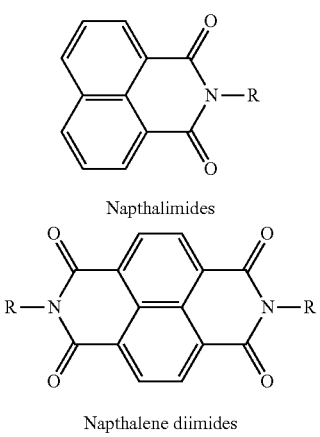

Napthalimides

Napthalene diimides

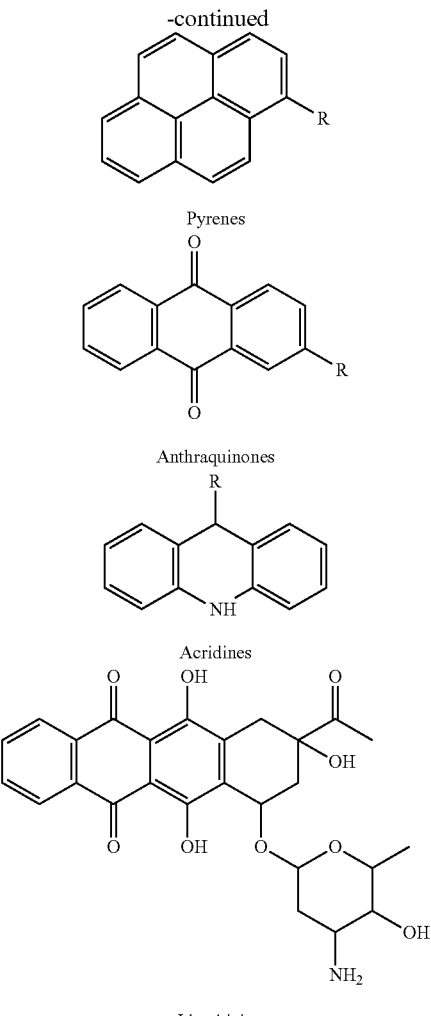

Pyrenes

Anthraquinones

Acridines

Idarubicin

The range of specific intercalator and minor groove binder structures is enormous as the field has been the subject of intense study for over 50 years. See R. Martinez and L Chacon-Garcia, *Current Medicinal Chemistry*, 2005, 12, 127-151. Therefore, the R groups include a broad range of organic functional groups. In many cases, interaction can be enhanced if R contains hydrogen bonding, cationic or hydrophilic character.

In addition, compounds such as cationic polymers, such as polyethyleneimine, interact with nucleic acid and have been proposed as gene carriers as evidenced by Xu et al, *International Journal of Nanoscience*, 2006, 5, 753-756 and Petersen et al, *Bioconjugate Chemistry*, 2002, 13, 845-854. Proteins are another well known class of materials that offer useful nucleic acid interaction and can be the basis for attaching nanoparticles to nucleic acids. Direct reaction with functional groups on the nucleic acid is also within the scope of this invention. For example, amine groups can be reacted with aldehydes to create a bond (Braun et al, Nano Letters, 2004, 4, 323-326)

In one embodiment the nucleic acid binding elements are specific binding agents that specifically target double-stranded nucleic acid molecules while not binding with single-stranded nucleic acid molecules. For example, minor-groove binding compounds specifically bind hybridized double-stranded DNA molecules, but do not bind to single-stranded oligonucleotide capture probes. In contrast, palladium chloride reagent indiscriminately binds to both the target molecules and capture probes. The binding element binds specifically to the target nucleic acid molecule while having little or no affinity towards non-target molecules. It is understood that the specific binding elements can include but are not limited to intercalators, minor-groove binding compounds, major-groove binding compounds, antibodies, and DNA binding proteins. The specific binding element binds to a specific site on a target nucleic acid without binding to non-desired areas. In one embodiment, the specific binding element is ethidium bromide. In alternative embodiments, the specific binding element is distamycin, idarubicin, or Hoescht dye.

In one embodiment the nucleic acid binding element also serves as a stabilizer as described elsewhere in this specification.

Stabilizers:

In one embodiment, the magnetic nanoparticles are surface functionalized with stabilizers to impart desirable properties. These stabilized magnetic nanoparticles demonstrate colloid stability and minimal non-specific binding. Furthermore, the presence of the stabilizer in solution while forming the magnetic nanoparticle controls the nanoparticle size.

The stabilizer provides colloid stability and prevents coagulation and settling of the magnetic nanoparticle. The stabilizer further serves to limit the size of the magnetic nanoparticle during the formation process. In one embodiment, metal magnetic nanoparticle are formed in a solution containing stabilizer and metal ions. In one embodiment the stabilizers are chelating compounds. Large magnetic nanoparticles are undesirable as they are more likely to precipitate out of solution. Therefore, the magnetic nanoparticle shall be small enough to remain in solution. In one embodiment, the magnetic nanoparticle is generally spherical in shape with a diameter from about 0.5-1000 nm. In one embodiment, the magnetic nanoparticle is generally spherical in shape and has a diameter from about 1-100 nm.

Suitable stabilizers include, but are not limited to, polyethyloxazoline, polyvinylpyrollidinone, polyethyleneimine, polyvinylalcohol, polyethyleneglycol, polyester ionomers, silicone ionic polymers, ionic polymers, copolymers, starches, gum Arabic, surfactants, nonionic surfactants, ionic surfactants, fluorocarbon containing surfactants and sugars. In one embodiment the stabilizer is a phenanthroline, bipyridine and oligovinylpyridine of the following formulas:

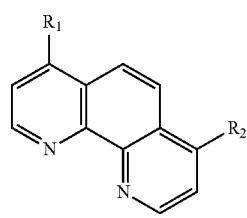

Phenanthroline

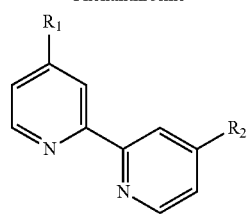

Bipyridine

-continued

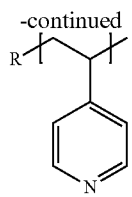

Oligovinylpyridine where $R_1$ is COOH, $CH_2OH$, $CH_2NH_2$, or $CH_2NHCH_3$; and $R_2$ is H, COOH, $CH_2OH$, $CH_2NH_2$, NH or $CH_2NHCH_3$.

In one embodiment where the magnetic nanoparticle contains palladium, these stabilizers link by acting as ligands for palladium ions and are therefore closely associated with the particle formation. In addition to linking, the stabilizers have hydrophilic groups that interact with the water phase. The linking and stabilization function of molecules such as phenathrolines in palladium particle formation is further described in Hainfeld, *J. Structural Biology*, 127, 177-184 (1999).

It is understood that particles derived from a broad class of materials (plastics, pigments, oils, etc) in water can be stabilized by a wide array of surfactants and dispersants that don't rely on specific coordination. These classes of stabilizers are also within the scope of this invention.

In one embodiment the stabilizer stabilizes the magnetic nanoparticle from precipitation, coagulation and minimizes the non-specific binding to random surfaces. In another embodiment, the stabilizer further functions as a nucleic acid binding element as described below.

Linker:

The linker is bound directly to the magnetic nanoparticle to allow the attachment of other intermediate connecting groups or target analyte binding elements. It is understood that the linker can also serve as a stabilizer or scaffold.

The linker can be bound through various binding energies. The total binding energy consists of the sum of all the covalent, ionic, entropic, Van der Walls and any other forces binding the linker to the magnetic nanoparticle. In one embodiment, the total binding energy between the linker and the magnetic nanoparticle is greater than about 10 kJ/mole. In another embodiment the total binding energy between the linker and the magnetic nanoparticle is greater than about 40 kJ/mole. Suitable linkers include, but are not limited to ligands, phenanthrolines, bidentates, tridentates, bipyridines, pyridines, tripyridines, polyvinylpyridines, porphyrins, disulfides, amine acetoacetates, amines, thiols, acids, alcohols and hydrophobic groups.

Scaffold Compositions:

The magnetic acid binding element may be connected directly to the magnetic nanoparticle or a linker. Alternatively, the nucleic acid binding element is attached to a scaffold, either individually or as a multiplicity. In either case, the final conjugate is endowed with the two essential properties—nucleic acid specific recognition-binding and an attached magnetic nanoparticle. Attaching the nucleic acid binding element to the scaffold may be by way of any of the common organic bonding groups such as esters, amides and the like.

Attachment to a common scaffold creates an enormous range of possible sizes, shapes, architectures and additional functions. In one embodiment the scaffold composition is a linear chain with the two functional groups at the ends. The chain itself can be of any composition, length and ionic character. In an alternative embodiment, often used in biological applications, polyethylene glycol with a reactive amine, acid or alcohol end groups is utilized as included in the following example.

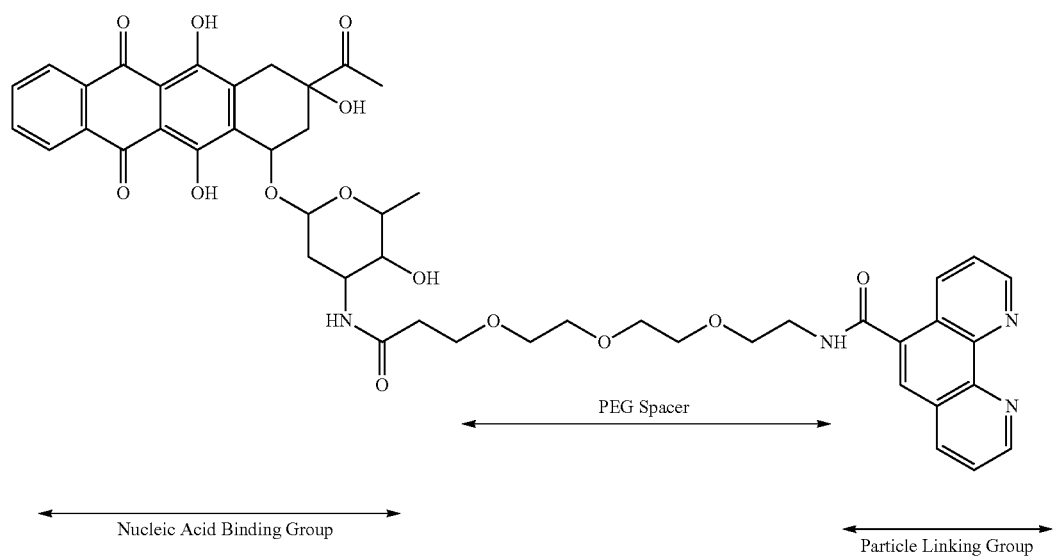 [SMILES: CC(=O)C1(O)Cc2c(O)c3c(c(O)c2C(OC2CC(NC(=O)CCOCCOCCOCCNC(=O)c4cc5cccnc5c5ncccc45)C(O)C(C)O2)C1)C(=O)c1ccccc1C3=O]
Linear short spacers with cationic character can be desirable as they can enhance intercalation performance.
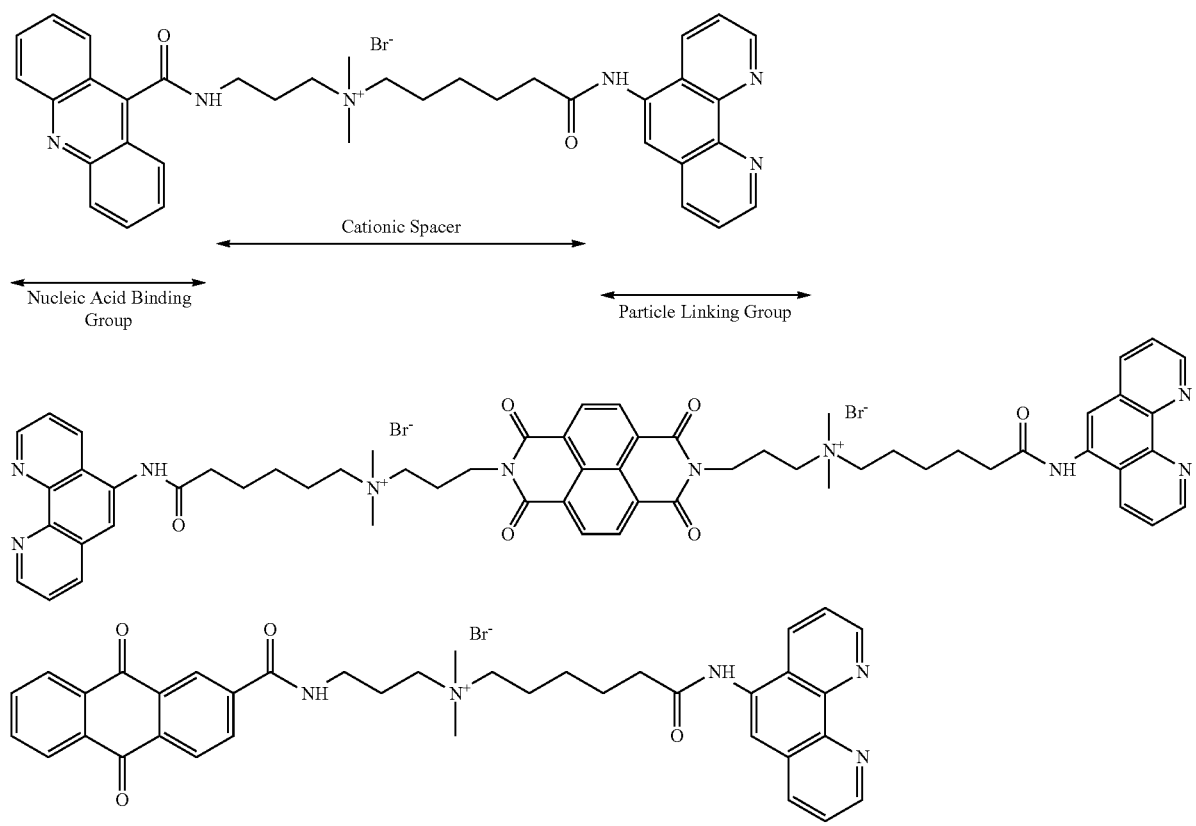
A polymeric or oligomeric scaffold allows for multiple groups to be joined in the same structure where the number of groups is limited only by the size of the chain.

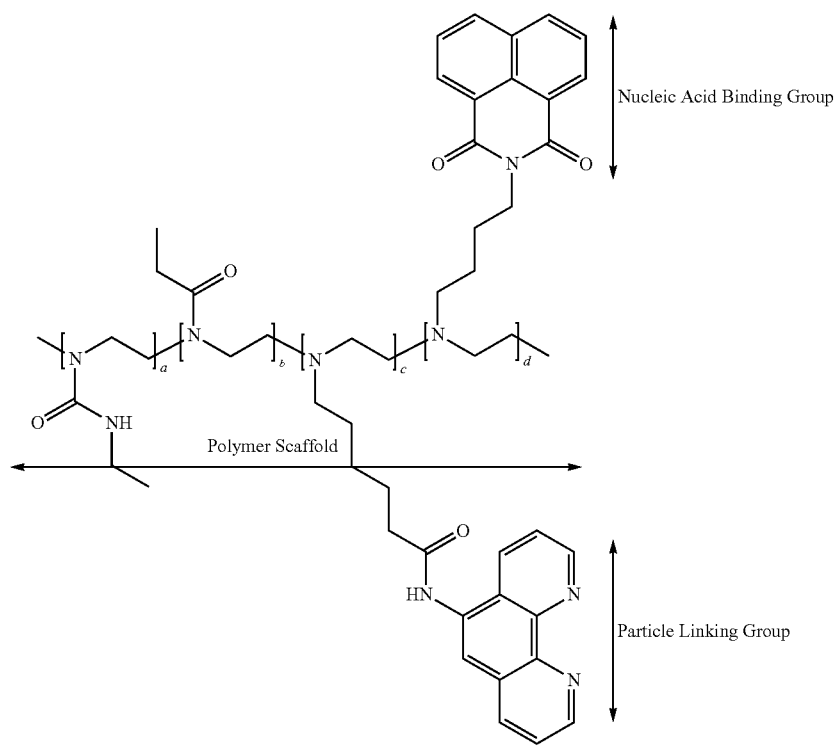

In addition to short and long chain structures scaffolds can be built with branched or very highly branched architectures. Furthermore, scaffolds can be a microgel particle with nanoparticles bound to a swollen polyvinylpyridine interior and peripheral nucleic acid binding elements are illustrated. In another embodiment the scaffold is a core-shell latex particle with magnetic nanoparticles centers and peripheral nucleic acid recognition groups populating the surface. It is understood that any scaffold compositions can be incorporated to connect intermediate connecting groups, magnetic nanoparticles or nucleic acid binding elements.

Steric Stabilizers:

In one embodiment a steric stabilizer is used to attach the target analyte binding element to the magnetic nanoparticle. The steric stabilizer is capable of functioning as a stabilizer, linker and scaffold as described above. In one embodiment the steric stabilizer is polyethylenimine, polyethyloxazoline or polyvinylpyrrolidone. The steric stabilizer binds to the magnetic nanoparticle with a total binding energy of at least 10 kJ/mole. In another embodiment the steric stabilizer binds to the magnetic nanoparticle with a total binding energy of at least 40 kJ/mole. The use of steric stabilizers eliminate any need for distinct stabilizers, linkers, or scaffolds. One or multiple nucleic acid binding elements can be attached to the steric stabilizer. Furthermore, one or multiple magnetic nanoparticles can be bound to the steric stabilizer.

Target Analyte Binding Substance:

In one embodiment for forming the target analyte binding substance on a magnetic nanoparticle, the magnetic nanoparticles are formed in solution with a stabilizer such as dimethyaminopyridine (DMAP). The stabilized magnetic nanoparticles are purified to retain clusters of the desired size. The nanoparticles are then treated directly with a nucleic acid binding element such as ethidium bromide or with a nucleic acid binding element connected to a linker or with a scaffold composition containing the nucleic acid binding element. The scaffold composition can be a polymer containing nucleic acid binding elements such as napthalimide or acridine. The polymer displaces some of the DMAP and attaches to the particle. It is understood that the nucleic acid binding element can be chemically attached to the scaffold composition prior to the attachment of the scaffold composition to the particle.

In another embodiment for forming the target analyte binding substance on a magnetic nanoparticle, the magnetic nanoparticles are formed in solution in the presence of a nucleic acid binding element such as ethidium bromide or in the presence of a nucleic acid binding element connected to a linker or in the presence of a scaffold composition containing the nucleic acid binding element. The scaffold composition can be a polymer containing nucleic acid binding elements such as napthalimide or acridine. It is understood that the nucleic acid binding substance connects to the particle during the particle formation process and may offer some colloidal stability to the dispersion. In addition, stabilizers in the form of ionic surfactants, non ionic surfactants, water soluble oligomers and polymers may also be added to enhance colloid stability and control particle size.

In one embodiment, the nucleic acid molecules are used for PCR application after preparation. It is known that PCR applications do not work successfully in the presence of detergents and alcohol. Therefore, for PCR application and additional filtering or cleaning step is utilized to prepare the sample prior to testing.

EXAMPLES

Sonication Bead Disruption

Spores were prepared and isolated from *Bacillus subtilis* from sporulation media+. To a 100 ul aliquot of the spores taken from the culture, an equal volume of 0.1 mm glass beads were added in a microfuge tube. The tip of the microfuge tube was placed in the socket of a Branson Ultrasonic sonicator. Using a power setting of 2, the beads within the tube were agitated for two minutes. Afterwards, gram staining showed that greater than 90% of the spores were disrupted by this process. This was confirmed with plating assays by counting colonies formed from spores surviving the process. Estimation of the amount of DNA released was accomplished by spotting an aliquot of the lysate onto the surface of a 1% agarose gel containing 1 mg/ml ethidium bromide. A Bio-Rad Fluor-S imager compared the intensity of the sample fluorescence against known standard amounts of DNA also spotted onto the gel surface. Using this technique, approximately 10 ng of DNA can be isolated from $2.5 \times 10^5$ spores.

Magnetic Examples:

Metal salts (nickel, cobalt, iron) with a small amount of palladium salt are dissolved in a solvent (water and/or polar organic solvent) along with a stabilizer (phenanthroline, bipyridine, polyvinylpyrrolidinone). A reducing agent is added (dimethylamineborane, sodium borohydride) and the mixture is held until the metal clusters are formed. If needed, solvents and excess salts can be removed by centrifugation, decantation, washing, and resuspension of the metal clusters.

Solution A—24 g of nickel chloride hexahydrate and 44 g of sodium citrate were dissolved in 500 ml of water.

Solution B—24 g of ethanolamine were dissolved in 500 ml of water.

Solution C—5 g of cobalt chloride hexahydrate were dissolved in 100 ml water.

Solution D—2 g of potassium tetrachloropallidate and 6 g of potassium chloride were dissolved in 100 ml of water.

Solution E—1 g of bathophenanthroline-disulfonic acid, disodium salt hydrate was dissolved in 100 ml water.

Solution F—3 g of dimethylamine borane were dissolved in 100 ml water.

Magnetic Example 1

In a 20 ml glass vial, 1 ml solution A and 1 ml of solution B were mixed. 0.1 ml of solution D was added, followed immediately by 0.2 ml of solution E. Then 0.5 ml of solution F was added and the mixture was held at 60 degrees C. for 30 minutes. After cooling to room temperature, the mixture was placed in a strong magnetic field for 10 seconds (the magnetic field was from the permanent magnetic removed from a discarded computer hard drive) and it was observed that most of the metal clusters moved to the wall of the vial nearest the magnet.

Magnetic Example 2

In a 20 ml glass vial, 0.2 ml solution A, 0.8 ml solution C and 1 ml of solution B were mixed. 0.1 ml of solution D was added, followed immediately by 0.2 ml of solution E. Then 0.5 ml of solution F was added and the mixture was held at 60 degrees C. for 30 minutes. After cooling to room temperature, the mixture was placed in a strong magnetic field for 10 seconds (the magnetic field was from the permanent magnetic removed from a discarded computer hard drive) and it was observed that most of the metal clusters moved to the wall of the vial nearest the magnet.

Preparation of Magnetite Clusters Example

A first solution of ferric chloride (0.8M), ferrous chloride (0.4M) and hydrochloric acid (0.4M) was mixed and 0.2 micron filtered. A second solution was prepared with 72 ml of ammonium hydroxide (30%) with water to make 1 liter.

1 ml of the ferric/ferrous chloride solution was added with stirring to 20 ml of the ammonium hydroxide solution. Stirring was continued for 15 seconds. The solution (in a 20 ml vial) was placed on a strong magnet and allowed to stand for 1 minute, after which all the product was pulled to the bottom of the vial. The clear supernatant liquid was decanted, replaced with water, mixed, and placed near the magnet. Again the product was pulled to the bottom of the vial. This process was repeated three times to wash the product free from any residual ammonium and iron salts. The vial was then filled with 20 ml of water and ultrasonicated for 5 minutes at 4 watts power. The suspension was then filtered through a 1 micron glass filter to give a stable suspension of magnetite nanoparticles that remain in suspension until pulled down by magnetic forces or centrifugation.

Attachment of Magnetic Nanoparticles Example

Nucleic acid molecules were purified from fruit flies, then lysed with ferrite nanoparticles followed by magnetic separation and elution. The magnetic beads captured more than 90% of available nucleic acid molecules.

Hybridizing to Capture Probes Example

Once the nucleic acid molecules are prepared, they are hybridized to capture probes on sensor electrodes. Samples of nucleic acid molecules from *Bacillus* cells were prepared through ultrasonic lysis and magnetic concentration. The eluted DNA was bound to probes on the sensor chip to demonstrate that there are no inhibitors of hybridization.

Sample Cleaning:

In one embodiment, the sample is cleaned to remove compounds which could potentially inhibit the binding of nucleic acid molecules to sensors. By attaching magnetic nanoparticles to the sample and manipulating the sample with a magnetic field the sample is both concentrated and cleaned from impurities.

Cleaning Example

Bacterial and spore samples mixed with soil were processed to evaluate complex samples. Soil is a complex medium which is known to inhibit PCR-based systems. Soil was added to samples containing six whole fruit flies. The flies are intended to represent insects that might be evaluated for carrying a disease like malaria. Up to 320 micrograms of the soil were added per milliliter of sample. The fruit flies were lysed and the DNA and RNA were captured using ferrite nanoparticles with the addition of ethanol. The magnetic nanoparticles were collected magnetically, washed with buffer and ethanol to remove contaminants then concentrated with magnetics. The nucleic acid molecules were then eluted in hybridization buffer at 90° C. to denature the DNA component. The ferric nanoparticles worked well in the presence of soil. Minimal loss was seen until the level of soil in the sample reached 32 milligrams per 100 micro liters where the solution becomes viscous and particle movement is difficult.

DNA from Complex Samples Example

*Bacillus* cells were mixed with cattle ear tissue or whole fruit flies and the mixtures were taken through the sample preparation process. The resulting nucleic acids were hybridized to probes on sensor chips. The chips were then treated with YOYO-1 dye to detect hybridized DNA. The target DNA sequences in the cells hybridized to the sensor chips at levels comparable to *Bacillus* cells processed separately. Negative controls without *Bacillus* showed no hybridized DNA. The experiment was repeated with dirt added to the samples as described above. Hybridization efficiency remained at least 60% of the hybridization seen in the sample without eukaryotic cells and dirt.

Washing Magnetic Nanoparticles with a Flow Example

Magnetic nanoparticles were bound to DNA and then the solution introduced into a clear plastic tube with a 2 mm diameter. A magnet was placed under the center of the tube. A wash buffer was pushed through the tube using a syringe pump. The magnetic nanoparticles visually remained in place through the washing. After washing the magnet was removed and the magnetic nanoparticles were rinsed out of the tube. DNA was eluted at high temperature and run on a gel. No apparent loss of DNA was observed.

Efficiency of Binding and Release of Magnetic Nanoparticles Example

Figure 36:
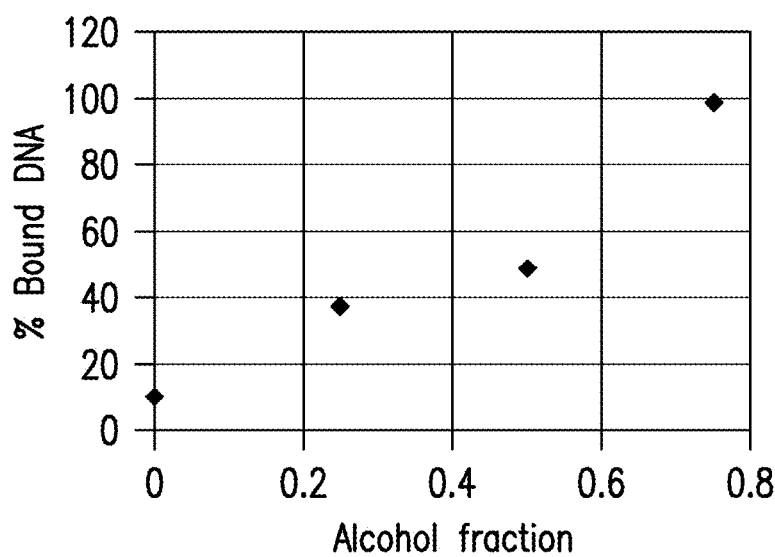
FIG. 36 is a graphical representation showing the release of the nucleic acid molecules from the magnetic nanoparticles.

Radiolabled DNA was used to determine the efficiency of binding to ferrite and the release of the nucleic acid molecules. Radiolabeled DNA with the magnetite suspension and three volumes of ethanol were mixed. The magnetite was pulled to the bottom of the tube using a magnet. The supernatant fluid was removed from the pellet and both fractions were counted in a scintillation counter. Binding was measured as a function of the fraction of ethanol in the mix. The results are shown in FIG. 36.

To determine the release efficiency, the bound DNA pellet is suspended in 100 µL of buffer as indicated in the table below, incubated for 10 minutes at 95° C., then collected on the magnet. The supernatant was separated from the pellet and both were counted.

| Buffer | Supernatant cpm | Pellet cpm | % Free |
|---|---|---|---|
| 500 mM Phosphate | 43,450 | 1925 | 96% |
| 50 mM Phosphate | 18,409 | 684 | 96% |
| 60 mM Citrate | 33,276 | 2164 | 94% |
| 100 mM Tris 0.2% SDS 1.5% Dextran sulfate | 911 | 35,878 | 3% |

The Tris buffer with SDS can be used for hybridization with magnetite bound DNA in order to allow for magnetic concentration of DNA or RNA near the sensor.

Rapid Movement of Magnetic Nanoparticles Example

Microchips were fabricated with metal coils having line widths of one micron. A current was run through the coils to produce a magnetic field. A solution containing magnetic nanoparticles was then spotted over the coils. The chip was placed under a microscope and current turned on through the coil. Within 10 seconds, clusters were congregating at the corners within the coil. Once the current was turned off the magnetic nanoparticles demagnetize and begin to diffuse back into solution.

Tissue Samples

Figure 37:
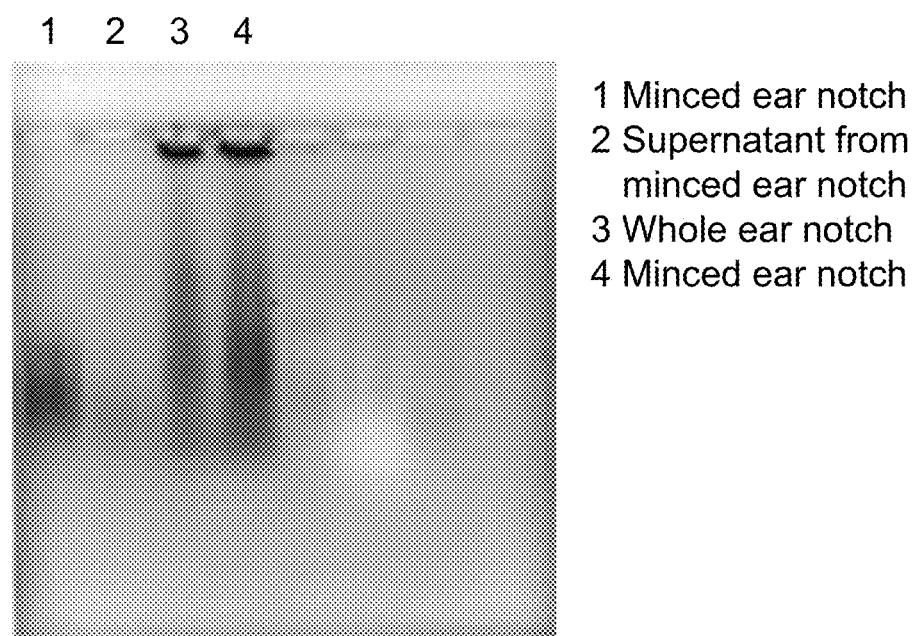
FIG. 37 demonstrates the nucleic acid molecule isolation obtained from using tissue from the ear of a cow.

As shown in FIG. 37, for diagnostic samples, an approach using tissue from the ear of a cow was evaluated. Ear tissue is often taken from cattle for evaluation and has skin, hair, large amounts of cartilage and is rich in blood. Ear plugs of about 3 mm in diameter were tested. A robust sample of about 1 microgram of nucleic acid molecules was isolated from an earplug using ultrasonication and 40 nm ferrite nanoparticles. The nucleic acid molecules were in the expected size range. Glass beads were not required for extraction from the tissue and subsequent treatment of an ear plug with bead beating did not result in additional nucleic acid molecule extraction. Sonication power and time settings were identical to those used in the previous examples.

Samples Contaminated with Soil

Figure 38:
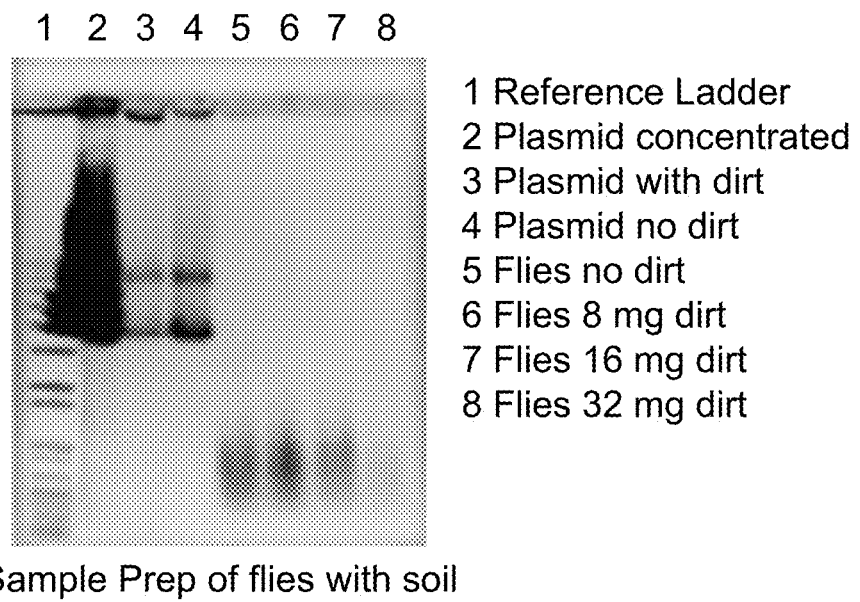
FIG. 38 demonstrates the nucleic acid molecule isolation obtained from using fruit flies contaminated with soil.

As shown in FIG. 38, to evaluate complex samples, bacterial and spore samples mixed with soil were processed. Soil is a complex medium which is known to inhibit PCR-based systems. Soil was added to samples containing six whole fruit flies. The flies are intended to represent insects that might be evaluated for carrying a disease like malaria. Up to 32 milligrams of the soil were added per milliliter of sample. The fruit flies were disrupted using ultrasonication in the presence of ferrite nanoparticles for two minutes. DNA and RNA were captured using ferrite nanoparticles with the addition of ethanol. The nanoparticles were collected magnetically, washed with buffer and ethanol to remove contaminants then concentrated with magnetics. The nucleic acid molecules were then eluted in hybridization buffer at 90° C. to denature the DNA component. Minimal loss was seen until the level of soil in the sample reached 32 milligrams per 100 micro liters (lane 8) where the solution becomes viscous and particle movement is difficult under the current test conditions. It is understood that by increasing the disrupting power, modifying the solution, or changing the disrupting particles size or characteristics results could be optimized for extremely contaminated samples.

Preparation of Magnetite Clusters

A first solution of ferric chloride (0.8M), ferrous chloride (0.4M) and hydrochloric acid (0.4M) was mixed and 0.2 micron filtered. A second solution was prepared with 72 ml of ammonium hydroxide (30%) with water to make 1 liter.

1 ml of the ferric/ferrous chloride solution was added with stirring to 20 ml of the ammonium hydroxide solution. Stirring was continued for 15 seconds. The solution (in a 20 ml vial) was placed on a strong magnet and allowed to stand for 1 minute, after which all the product was pulled to the bottom of the vial. The clear supernatant liquid was decanted, replaced with water, mixed, and placed near the magnet. Again the product was pulled to the bottom of the vial. This process was repeated three times to wash the product free from any residual ammonium and iron salts. The vial was then filled with 20 ml of water and ultrasonicated for 5 minutes at 4 watts power. The suspension was then filtered through a 1 micron glass filter to give a stable suspension of magnetite nanoparticles that remain in suspension until pulled down by magnetic forces or centrifugation.

Example A

Three fruit flies were placed in each of two 1.5 ml Eppendorf tubes. One was loaded with 100 microliters of a mixture of 100 mM TRIS hydrochloride (pH 7.5), 1.5% dextran sulfate and 0.2% sodium dodecylsulfate (SDS). The other was loaded with 100 microliters of isopropyl alcohol and 10 microliters of 20% sodium dodecylsulfate. Both tubes were loaded with 10 microliters of 0.6% magnetite nanoparticles in water. Both tubes were sonicated at 20 kHz for 45 seconds (2 watts). Then 1 ml of isopropyl alcohol was added to the first tube and ½ ml of isopropyl alcohol was added to the second tube. The magnetic pellet was collected by a permanent magnet, the supernatant liquid decanted and 50 µL of 100 mM sodium phosphate was added to each tube, the pellet resuspended by repetitive pipetting, then incubated at 95 degrees C. for 2 minutes. The pellet was again collected on a magnet and the eluted DNA was run on a 1% agarose gel at 77 volts in TEA buffer. A DNA ladder was also run on the gel.

Figure 39:
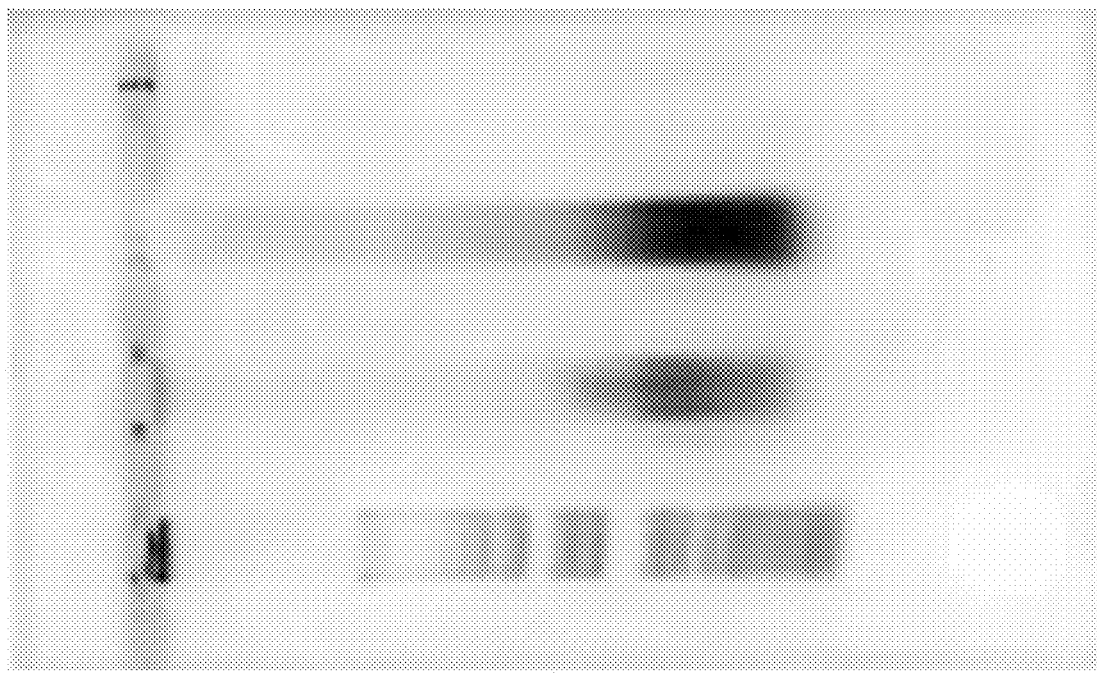
FIG. 39 demonstrates purified DNA recovered from fruit flies.

As shown in FIG. 39, the gel was stained with ethidium bromide and photographed with 302 nm excitation and a 610 nm filter over the camera. The purified DNA is clearly visible on the photograph. The top lane represents the second tube, the middle lane represents the first tube and the bottom lane represents a DNA ladder.

Example B

Four tubes, each with three fruit flies, 100 microliters of buffer and 10 µL of 0.6% magnetite nanoparticles were sonicated for 30 seconds at 5 watts at 20 kHz. The DNA was collected, eluted, run on a gel, stained and photographed as in Example A and shown in FIG. 40. The four buffers were as follows:
1. 100 mM TRIS, 1.5% Dextran sulfate and 0.2% SDS
2. Isopropylalcohol (IPA)
3. 90% IPA, 1% dodecylbenzenesulfate, 9% water
4. 90% IPA, 1% polyacrylic acid sodium salt, 9% water Example 13

Figure 41:
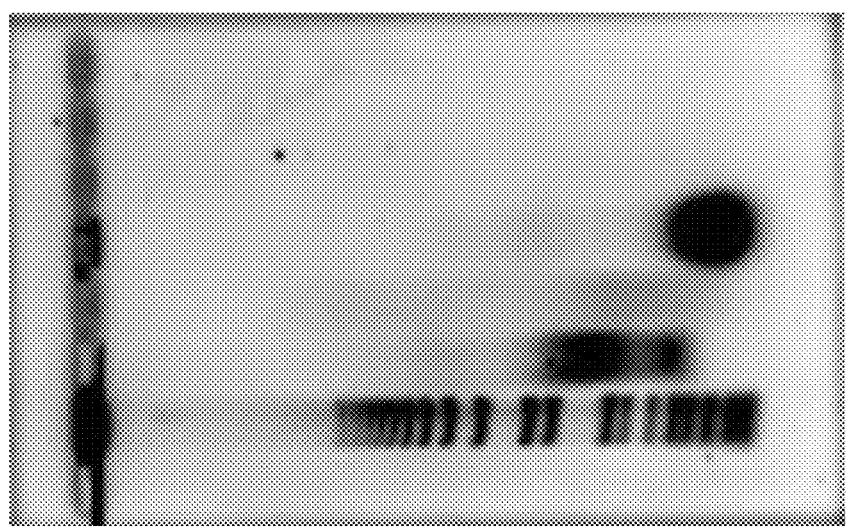
FIG. 41 demonstrates the recovery of nucleic acid molecules from yeast, grass and blueberries.

Portions of yeast, grass and blueberries were sonicated in 100 mM TRIS, 1.5% Dextran sulfate and 0.2% SDS as in Example A. The purification, gel and photograph were as in Example A and are shown in FIG. 41.

Example C

Three 1.5 ml Eppendorf tubes each containing about 10 billion *E. coli* cells and 33 mg of glass beads (100 micron diameter) and 40 microliters of 0.5 molar sodium phosphate, pH 7.5 were sonicated for 15, 30 and 60 seconds at 40 kHz, 10% amplitude with a 4 mm sonic tip inserted into the tube. The purification, gel and photograph were done as in Example A and are shown in FIG. 42.

This example shows that longer sonication times do not change the size distribution, i.e., that steady state conditions apply.

Example D

Figure 43:
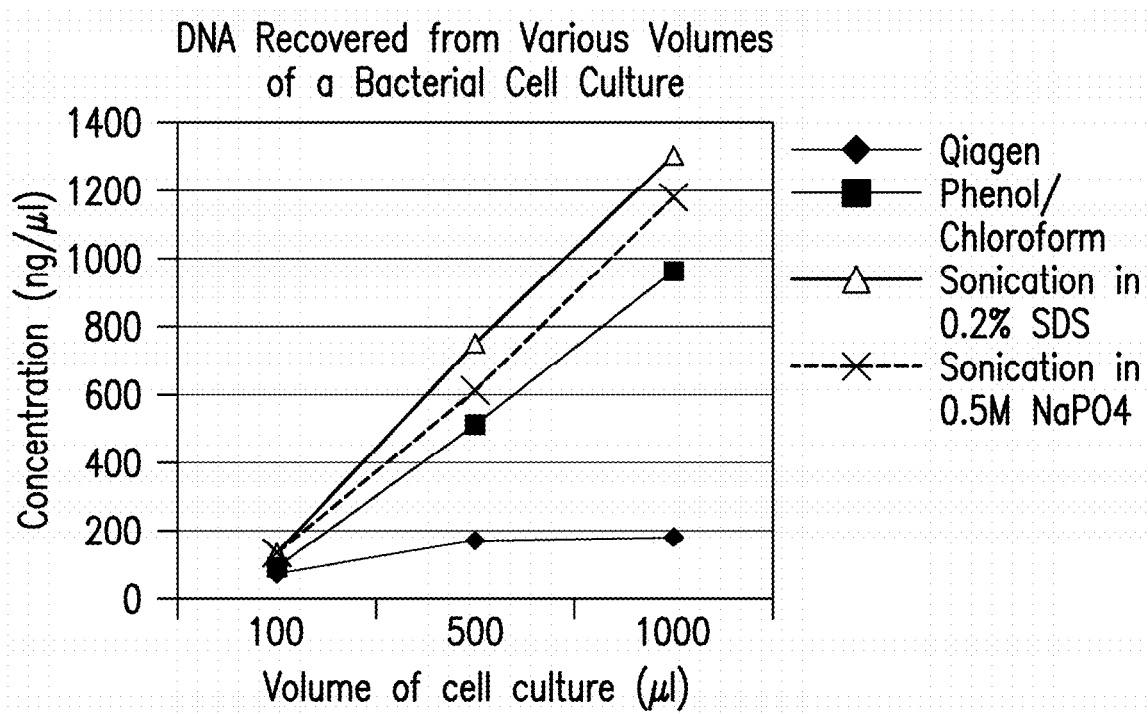
FIG. 43 is a graphical representation of DNA recovery from increasing volumes of a bacterial cell culture using the instant invention, the commercial QIAGEN kit for DNA recovery and the textbook Phenol/Chloroform method.

In this example, DNA is recovered from increasing volumes of a bacterial cell culture using two standard methods—the commercial QIAGEN kit for DNA recovery and the textbook Phenol/Chloroform method. These were compared to the method given in Example A, using 0.2% SDS and 0.5 M sodium phosphate as the buffer. The results are shown graphically in FIG. 43.

The graph shows that the method of this invention is superior to both the QIAGEN kit and the phenol/chloroform method.

Protective Buffer Example

Figure 44:
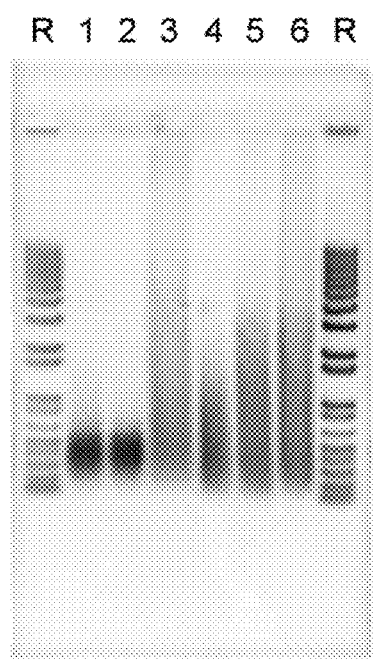
FIG. 44 demonstrates the effectiveness of high ionic strength buffer in protecting nucleic acid molecules during sonication.

In this example a comparison of protective buffers for DNA shearing by ultrasonication are shown in FIG. 44.

5 µL G1 plasmid DNA solution containing 5 µg of DNA were mixed with 50 µL buffer with 44 mg of zirconia beads of approximately 100 micron size in a 1.5 ml eppendorf tube. The tube was inserted into the socket of a Branson SLPt 40 kHz ultrasonicator. The sonicator was run at 50% amplitude for 12 minutes with a pulsed cycle of 10" on and 20" off. After sonication, a 20 µL portion of the mixture was eletrophorized on a 1% agarose gel at 100 volts in TAE buffer. All buffers were adjusted to a pH between 7 and 8. A DNA ladder was run on both sides of the sample lanes. The lanes contained:
  Lane 1. TE (Tris-(hydroxymethyl)aminomethane) with EDTA (ethylene diamine tetra-acetic acid)
  Lane 2. 10 mM Tris-(hydroxymethyl)aminomethane
  Lane 3. 500 mM sodium phosphate
  Lane 4. 50 mM sodium phosphate
  Lane 5. 60 mM sodium citrate
  Lane 6. 3% sodium chloride This example shows that high ionic strength buffers, such as metal salts are effective in protecting the DNA during sonication. The buffer allows for larger DNA fragments in a steady state sonication. Lower ionic strength buffers such as Tris-hydroxymethyl aminomethane are less protective and yield smaller DNA fragments suitable for particular applications.

In one embodiment, the size stabilizer is a protective high ionic strength buffer including soluble salts from cations including the Group 1 and Group 2 metals of the periodic table with anions from Group 7 of the periodic table as well as more complex anions exemplified by sulfates, phosphates, and acetates. In another embodiment the buffer is capable of being stable and soluble at pH values between 7 and 8. The soluble concentration of the buffers is, in one embodiment, greater than 1%. In another embodiment, the concentration is greater than 5%.

Surfactant Examples

Two fruit flies were placed in each of 3 eppendorf tubes containing 25 of 100 micron glass beads from Biospec Products. To the first tube, 100 microliters of water was added. To the second tube, 100 microliters of 1% sodium dodecylsulfate was added. To the third tube, 100 microliters of 1% sodium dodecylbenzenesulfate was added. All three tubes were sonicated for 2 minutes on power level 2 on a Branson Sonifier 150, placing the tube into the threaded orifice of the ultrasonic converter where the tips are normally threaded into the converter. The power meter showed an initial reading of about 8 watts which dropped during the 30 seconds to about 4 watts, which level continued during the remainder of the sonication time. After sonication, 20 microliters of the fluid above the glass beads was removed and placed in the wells of an agarose electrophoresis gel, made with TAE buffer. A DNA ladder was included in the first lane to determine the size of the sonicated DNA fragments. After electrophoresis at 70 volts for 90 minutes, the gel was soaked with gentle agitation with an ethidium bromide solution. Then a black light photograph of the gel was taken, as shown in FIG. 38.

Figure 45:
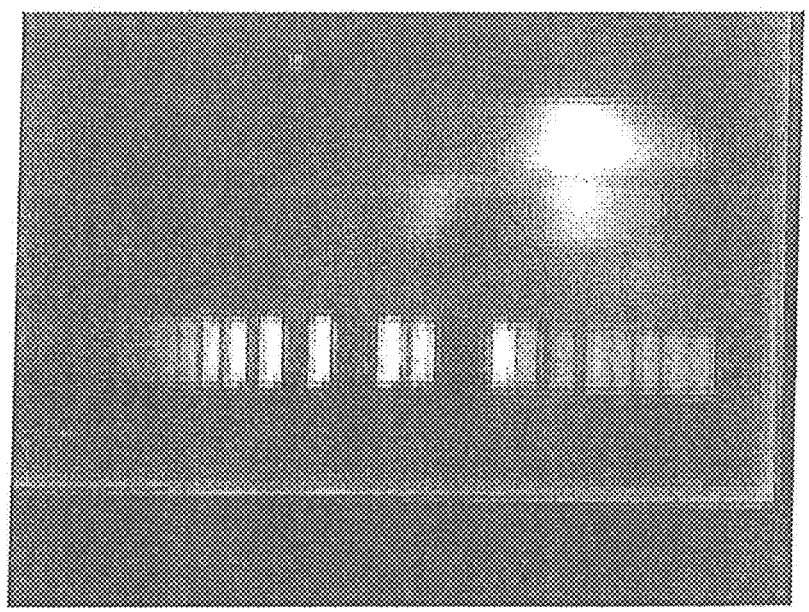
FIG. 45 demonstrates that sonication in the presence of a selected size stabilizer can provide a high yield of DNA in a limited size range.

Referring to FIG. 45, the first lane above the DNA ladder shows the water sonication result. A low yield of DNA is seen, and the fragments are smaller than 400 base pairs. The second lane above the ladder shows the sodium dodecyl sulfate sonication result. The yield of DNA is much higher, and the fragment sizes range from 300 to 2000 base pairs in size. The third lane above the ladder shows the sodium dodecylbenzenesulfate result. Again, the yield of DNA is high, evidenced by the bright spot on the photograph, and the size range is from 300 to 1000 base pairs. This example shows that sonication in the presence of a selected surfactant can provide a high yield of DNA in a limited size range from a live source such as fruit flies.

Exemplary Process

A sample in the form of a liquid or solid is loaded into the center reservoir using one of several specialized covers designed for a specific sample type or source. The cover may contain, for example, a lance for blood collection, a frit to exclude large debris, or a set of filters to pass only certain materials, cells or pathogens of within a desired size range into the cartridge central chamber.

The instrument run operation begins by extracting a sufficient amount of lysis buffer from its storage reservoir and pumping it into the center sample reservoir. Mixing with the loaded sample is performed by alternating the pumping direction of a volume slightly less than that of the combined liquid volume of the sample and lysis buffer.

For certain types of samples which are difficult to chemically lyse, an ultrasonic horn integrated within the instrument drive unit is activated to drive glass bead beating of the lysis mixture. With or without utilizing the glass-bead beating step, the lysis mixture is incubated at ambient temperature for 5-10 minutes to allow chemical lysis of the sample. While incubating the sample, certain preparative actions for downstream processing steps can be performed. For example, 100 µl of DI water is added to reconstitute dried P30 size-exclusion resin packaged inside the desalting pod.

Upon completion of the chemical lysis incubation, the lysate mixture is extracted through a 30 µm filter and loaded into a reservoir containing 15 µl ferrite magnetic particles (prepared as a suspension in a viscous liquid such as polyethylene glycol (PEG), sugars, glycerol, or other organic polymers such as PVP. The solutions are mixed and allowed to incubate for 5 minutes. During this incubation, the nucleic acids (DNA/RNA) are bound to the magnetic particles.

The sample-magnetic particle complex is extracted and passed through a channel that passes over a magnet in small volume pulses (1 to 10 µl). Each pulse is allowed to dwell for at least 2 seconds over the magnet. This ensures sufficient time for the magnetic particles to be attracted to the magnet. The residual buffer is flushed through the channel and into the cartridge waste reservoir.

The ferrite reservoir chamber is flushed with an appropriate volume of water (40 µl to 200 µl) that is then passed over the magnet to collect any residual nucleic acid-ferrite complex. This step also rinses previously bound magnetic particles of contaminates and any remaining buffer. The magnetic channel is purged with air to remove any residual rinse water.

In order to release bound nucleic acids efficiently from the ferrite, a heater is activated and allowed to stabilize at 80° C. A 22 µl volume of elution buffer (50 mM sodium phosphate with 1 to 15% organic polymer (2% PVP preferred) is withdrawn from its reservoir and then pumped into the magnetic channel to flow over the ferrite/sample pellet. The cartridge valve is rotated a few times around away and back to the magnet to loosen the ferrite/sample pellet. The ferrite/sample pellet is rotated over the heater and allowed to incubate at 80° C. for 5 minutes. During this time, the sample is released from the magnetic particles into the elution buffer.

The magnetic channel is then rotated back to position it over the magnet where the magnetic particles are once again attracted to the magnet. This step allows the released NA material to be separated from the depleted ferrite particles by extracting the eluate solution from the channel. Removal of the phosphate salts any other contaminants is achieved by pumping the eluate into the desalting pod. Because of the volume of the eluate is small, a minimal amount of DI water (10-100 µl, 55 µl utilized initially) is used to push the sample through the pod. The purified sample exits the pod through a 0.2 µm filter and spills into an overflow reservoir. The sample is now ready for PCR (or other processing that may include: restriction digests, phosphorylation, de-phosphorylation, ligation, nuclease treatment).

Nucleic Amplification

The purified material derived from the cartridge sample-prep processing is extracted out of the desalting overflow reservoir, taking a volume of 45 to 90 µl. This solution is used to set up either one or two separate amplification reactions. For example, to perform two independent PCR reactions, the purified nucleic acid material is divided by pumping half the solution into the PCR Mix 1 reservoir to reconstitute a lyophilized PCR pellet having one particular set of amplification primers; the remaining half of the solution is used to reconstitute the lyophilized PCR pellet in the PCR Mix 2 reservoir that has a different set of amplification primers.

Following PCR pellet reconstitution, 39 µl of each PCR Mix is dispensed into its designated PCR channel (mix 1 into channel 1, and mix 2 into channel 2), as viewed on the underside of the cartridge rotor valve. The instrument pre-warms and stabilizes the two heaters to a start temperature (for example, 45-65° C. for RT-PCR and 93-98° C. for PCR). Subsequently, the cartridge valve is rotated so the PCR channels are aligned over the heaters, while the inlet and outlet ports are blocked to contain pressure that arises from the heating of the PCR solution. Standard methods and variations for both Reverse Transcription -PCR (RT-PCR) and PCR reactions (i.e. two or three step PCR) can now be performed according to the process best suited for optimal product generation, and which avoids artifact products or that is least sensitive to problematic inhibitors that may be carried over from sample-prep. When PCR cycling is completed, the instrument turns off the heaters to allow the temperature in the channels to cool to ambient. The machine rotates the valve and uses the syringe pump to extract 30 µl of PCR sample 1 and 2 from their respective channels. These volumes are combined into a PCR Mix reservoir for storage and preparation for detection.

Detection Method Steps

A portion of the pooled PCR products (10-50 µl) is taken from the total volume held within the PCR Mix 2 reservoir and then dispensed into a mixing chamber. Next, hybridization buffer (250 mM $NaP_i$/0.1% SDS) is aspirated from its storage reservoir and mixed with the selected amount of PCR solution in the mixing compartment. For optimal performance, the surface of the sensor microchip must be pre-wet using a rinse of the hybridization buffer only and then be allowed to reach and maintain 60° C. for a few minutes before pumping in 70 µl of the hybridization test solution that contains the pooled PCR reaction output material.

Once dispensed into the reaction chamber, target derived PCR products hybridize to appropriate sensor electrode regions on the surface of the test microchip. Multiplexing capability is achieved due to the sequence specificity imparted by utilizing different capture oligonucleotide probes, which have been spatially addressed as an array overlaying the patterned groups of independent sensors on the microchip. The duration of hybridization reaction can be from 30 to 600 seconds, depending on preference for greater sensitivity or a shorter time to result. The test hybridization solution can be held static on the surface for the duration of the hybridization, or be flowed in a pulsed or continuous manner. Afterwards, to remove any remnants of the amplification reaction (non-hybridized nucleic acids, PCR products, or primer oligonucleotides, and dNTPs and any reaction by-products) the reaction chamber is rinsed with one 130 µl aliquot of hybridization buffer only solution, with the chip heater maintained at 60° C.

Incubation with catalyst solution (noble metal ionic compound, colloid or cluster) follows the rinse immediately. Colloid or cluster catalysts may be functionalized with oligonucleotides, antibodies, or other target generic or specific recognition molecules. The catalyst reagent may be held static, or flowed in a pulsed or continuous manner over the reaction surface for 30 to 600 s at 25-65° C. The catalyst is rinsed off with 2×100 µl aliquots of hybridization buffer. The chip surface temperature is then increased to 68° C. to prepare for development.

A lyophilized pellet of developer chemicals is hydrated in 96 µl of DI water and 10 to 60 s of mixing within the developer reservoir chamber. The reconstituted developer is aspirated and then dispensed at a very slow flow rate for 105 s. About 25 μl of developer will react with the chip surface over this time. The chip temperature is lowered to 50° C. and rinsed with 100 μl of $H_2O$. The syringe aspirates air from a designated chamber, and dispenses it over the chip surface to dry it. A 60 s delay with the heater at 50° C. ensures the surface is dry. The resistance of the sensors is measured.

Exemplary Cartridge

Figure 46:
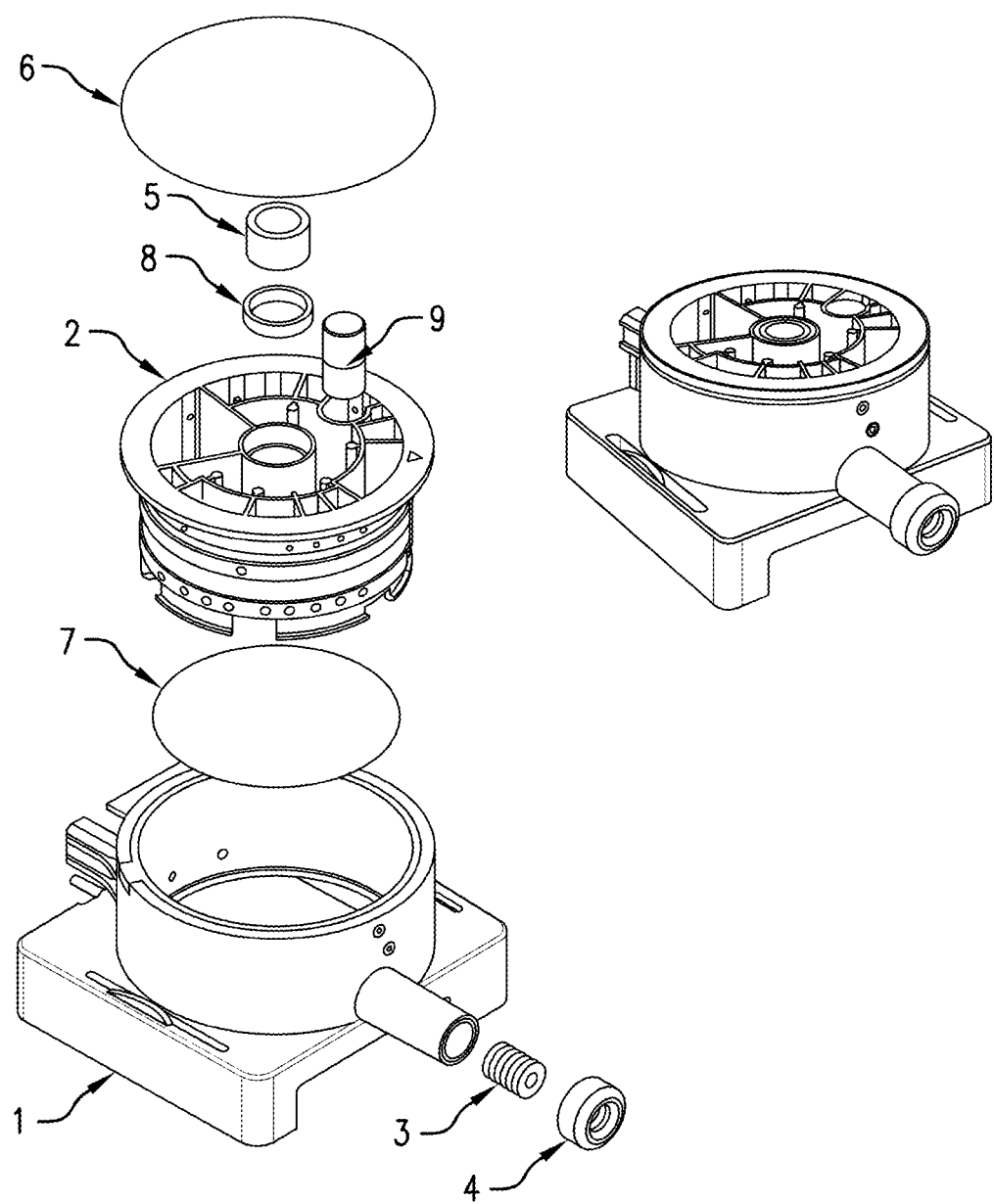
FIG. 46 depicts an exemplary cartridge.
Figure 48A:
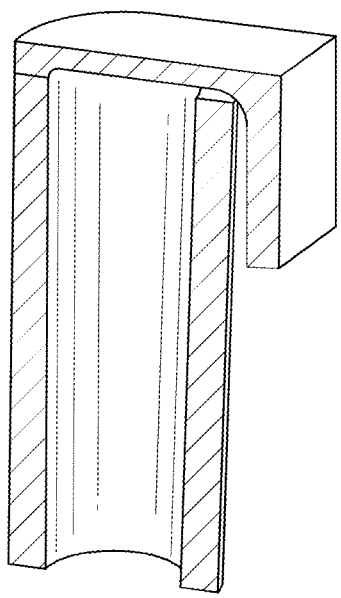
Figure 48B:
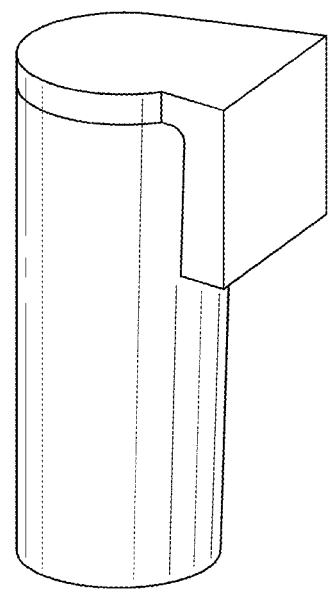
Figure 48C:
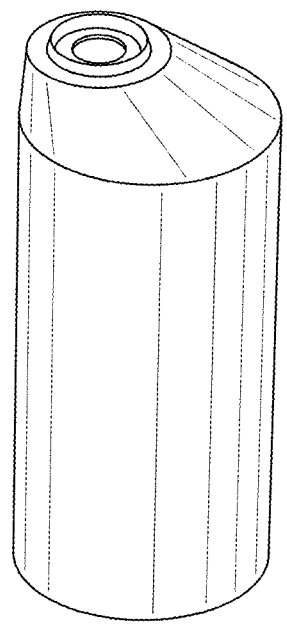
FIG. 48C and FIG. 48D are views of a second exemplary insert pod.
Figure 48D:
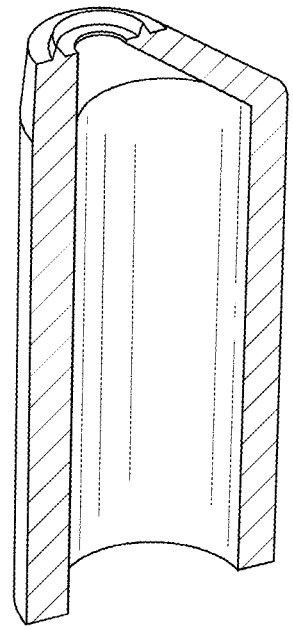

The cartridge comprises two plastic pieces: a main body and an internal rotor (see FIG. 46). The cartridge body has a syringe plunger actuated by a screw type motor to move fluids. A reaction chamber is located on the opposite side of the cartridge body with one wall of the cartridge formed by the microchip sensor. Multiple reagent chambers are built into the top of the cartridge rotor and reaction chambers and flow channels are molded into the bottom of the cartridge rotor. The chambers are sealed with plastic seals on the top and bottom of the rotor.

Figure 49:
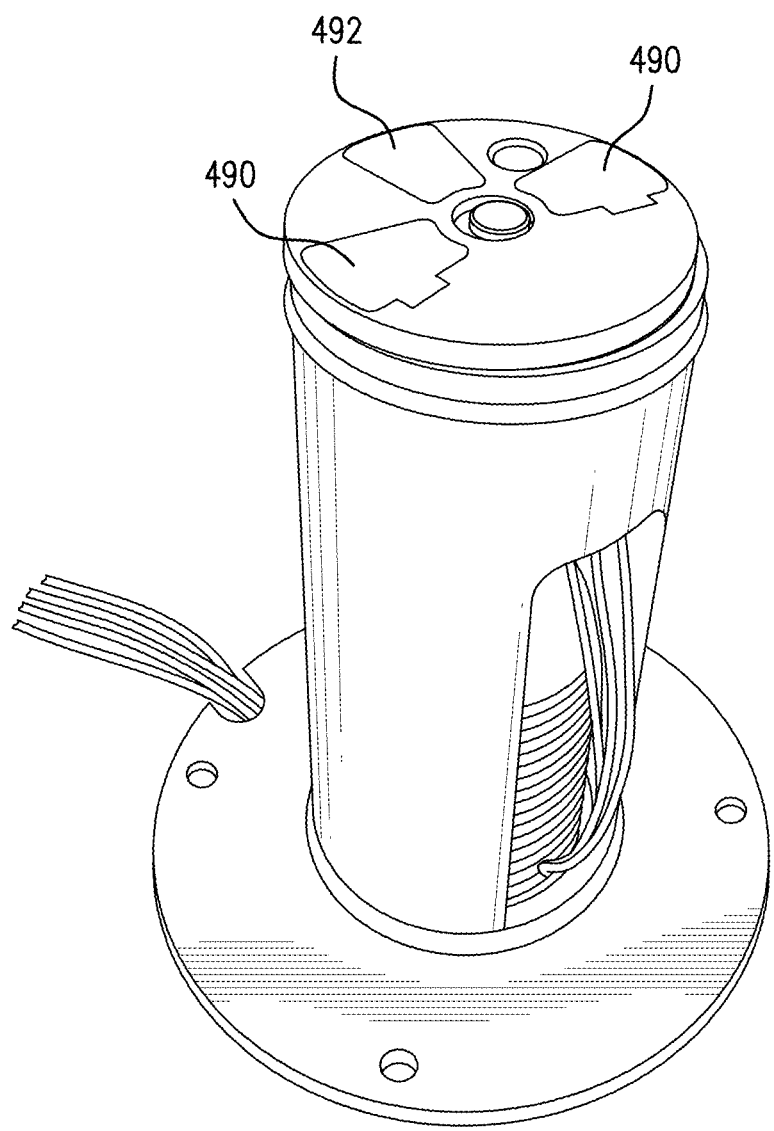
FIG. 49 is a perspective view of a drive platform.

The cartridge sits on a drive mechanism that rotates the inner plastic component to align various rotary valve channel ports with ports in the outer housing for the syringe and detection chamber. A second motor in the assembly is used to drive the cartridge syringe plunger to move reagents and solutions. The drive assembly is depicted in FIG. 47A and shown with a cutaway view. For sample and organism/cell disruption, an ultrasonic horn is integrated within the drive assembly and contacts the underside of the cartridge. The drive platform features an embedded magnet and two resistive elements. The magnet serves to concentrate biological molecules associated with paramagnetic particles, while the pair of regulated heaters 490 and a chill plate 492 (see FIG. 49) is used to heat/cool and control temperatures of specific channel areas on the bottom of cartridge for biological reactions to be performed. The chill plate is a thermally conductive material, such as a metal plate, that transfers heat away from the disposable insert.

Filtering

To provide flexibility with respect to various types of input material such as blood versus insect samples, the cartridge is designed with filtration pods (FIG. 47C) that can be varied to match the sample needs without changing the basic design. Modular pods are used to incorporate filtration and column separation into the cartridge. Filters are attached to rings and columns are prefabricated in cylinders that are then welded into the cartridge. The number and type of pods can be selected based upon the target sample. For example samples can be pre-filtered to remove large debris particles prior to disruption, whereas insect samples would not be filtered prior to disruption.

Desalting:

An insert pod can be placed into the rotor valve (see FIG. 47C) that contains a desalting resin/matrix material. Flowing partially purified sample through the insert will remove any ions that could interfere with biological reactions (i.e. iron inhibition of PCR amplification).

The insert must also manage/control the flow of fluid during the desalting process. Surface properties of the plastics, reservoir geometries, and air bubbles can affect the flow of the fluid. Alternate design concepts have been made to minimize these aberrations (FIGS. 48A-D). The left design (FIGS. 48A and 48B) utilizes a cap which directs the fluid over the side of the pod. Without the cap, the hydrophobic nature of the plastic can cause variability of the volume required to cause spill over. Similarly, the right design (FIG. 48C and FIG. 48D) utilizes a smaller exit port, which requires less volume to break surface tension.

Viral Separation

The sample preparation system should provide an ability to enrich viruses and bacteria from complex samples to improve the sensitivity of detection systems and the efficiency of gene sequencing. Automated genomic sequencing is becoming more cost effective and provides the best capability for identification of unknown pathogens. The latest generation of gene sequencers, such as Illumina's MySeq, provide the capability to sequence viruses and bacteria in a matter of hours. However, sample preparation is critical for efficient genes sequencing. In particular, it is necessary to enrich a sample for the target pathogens by isolating the viral and bacterial material away from eukaryotic material found in samples, such as human blood samples or insects. Otherwise the much larger eukaryotic genomes will dominate the sample and will necessitate sequencing much larger volumes of material to identify the viruses or bacteria. Since a key advantage of sequencing is the ability to identify previously unknown pathogens, it is important that the enrichment process does not rely on prior knowledge of the pathogens.

The disclosed approach may be selectively enrich the purification of targeted pathogens in a sample's background of genetic materials (such as host cells). The exemplary cartridge features a special chamber designed to accommodate a column insert (see FIG. 46). Originally, a desalting column was intended to be positioned into this compartment.

After disrupting the sample mechanically, the material is passed through a first filter to remove intact eukaryotic cells. For bacteria, the filter will have 2 to 4 micron pores, allowing the bacteria to pass but collecting any eukaryotic cells. For viruses, the filter can have pores as small as 200 nm. The bacteria or viruses are then separated and concentrated using a filter with smaller pores to capture the pathogens. A filter with 200 nm or less openings will be used for bacteria and a filter with 30 nm or less openings will be used to capture viruses or a combination of bacteria and viruses. In this step, the bacteria or viruses remain intact and nucleic acids released from ruptured eukaryotic cells will be washed through the filter. The washed viruses and/or viruses will then be lysed and nucleic acids can then move through the filter to be processed further.

The primary fraction of the sample will pass through a filter to remove large debris and whole eukaryotic cells, and then the bacteria or viruses will be captured using a novel filter based on a pnc-Si or track etched membrane which will capture particles greater than 30 nm in size. These membranes allow for fine control of the size of material allowed to flow through and minimizes loss due to material being trapped in the filter.

Porous nanocrystalline silicon (pnc-Si) membranes represent a revolutionary advance in membrane technology. The most significant structural characteristic of pnc-Si is its molecular scale thickness (10-50 nm), which results in transport resistances and losses that are orders-of-magnitude lower than conventional membranes that are 100-10000 times thicker than pnc-Si. Because transmembrane resistance to both convective and diffusive transport increases is proportional to membrane thickness, molecularly thin membranes effectively minimize a critical parameter that adversely affects membrane permeability. Consequently, the permeability of pnc-Si to water, gas and diffusing species are the highest reported for experimental or commercial nanoporous membrane. In many practical settings, pnc-Si membranes offer transport resistances that are so small compared to other components in the system, that they can be neglected. Despite the nanoscale thickness of pnc-Si, the membranes are mechanically robust and can be manufactured in large quantities.

The resolution of separations is also known to improve for thinner membranes, and pnc-Si membranes have been shown to separate nanoparticles and proteins with resolutions exceeding 5 nm regardless of the mode of transport. The membranes are also modifiable through silane chemistries that can be used to graft polymers to reduce protein binding and fouling, or manipulate surface charges for charge-based separations. Additionally, ultrathin membranes minimize sample loss through absorption to internal surfaces, providing a low loss membrane for processes involving low concentrations and small volumes.

Selective enrichment and cleaning of these pathogens should improve downstream assay performance by virtue of a more effective removal of inhibitors and limiting the presence of extraneous eukaryotic nucleic acids prior to a subsequent lysis step. Nucleic acid binding and elution steps with our magnetic particles perform better when clean nucleic acids has been the input.

Loaded materials in the collection column will be washed with rinse buffer, and then undergo our sample processing. The excluded, retained and passed-through column materials will be titrated into amplification reactions to determine whether certain pairings of exclusion membranes best enrich virus over arthropod material. As virus becomes enriched in the column-retained fraction, RT-PCR detection should persist or improve with the most dilute manipulations of a titrated series; detection of arthropod DNA should diminish with effective fractionation by a filter set.

Sample Input

Figure 50:
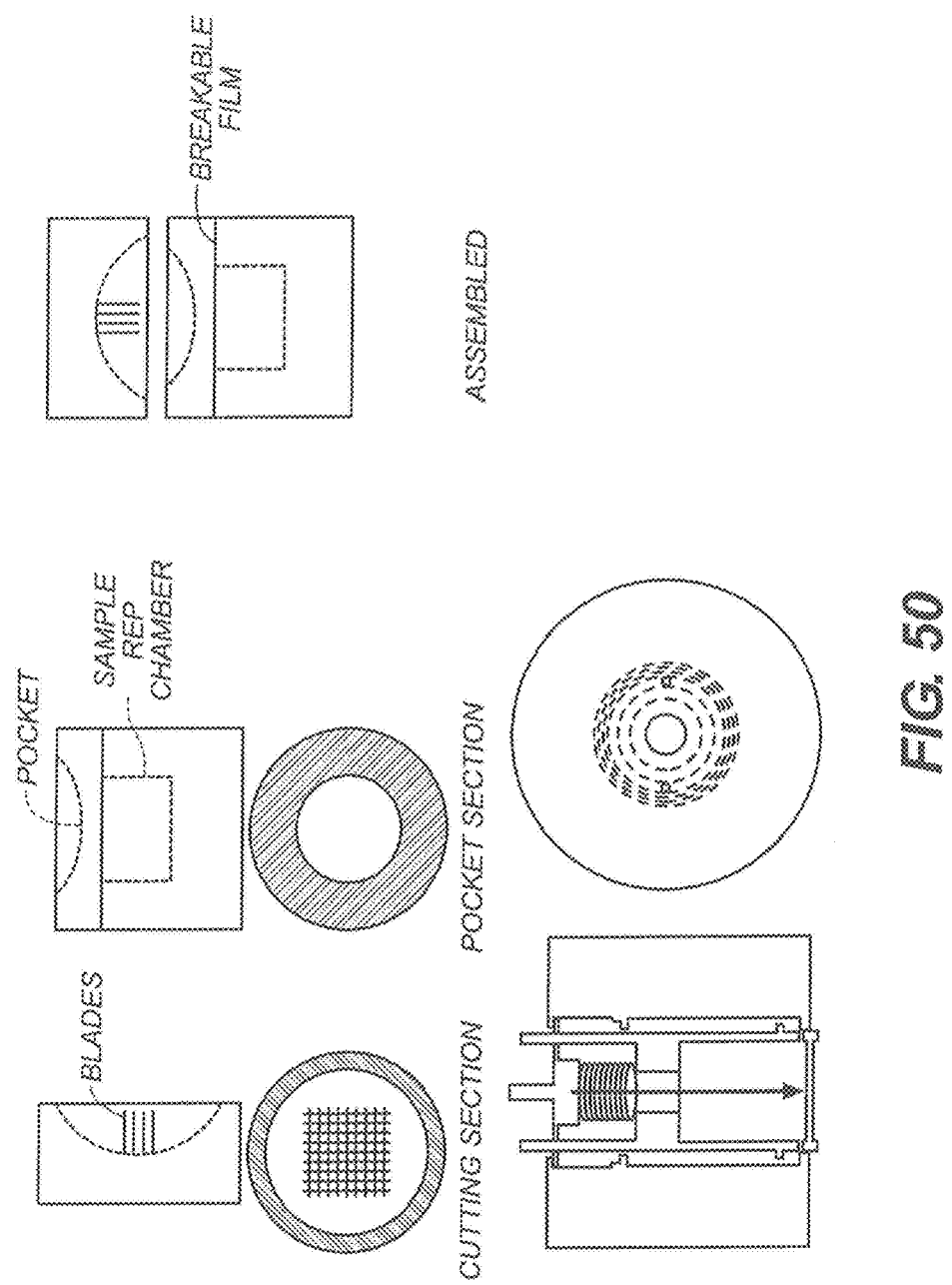
FIG. 50 is a depiction one an exemplary cover for sample pre-processing.

Different cartridge lid accessories have been designed to address varying types of sample input. For example, FIG. 50 shows a cartridge cover designed for input of insect vectors or tissue samples, where the sample material may need to be crushed prior to sonication.

Figure 51:
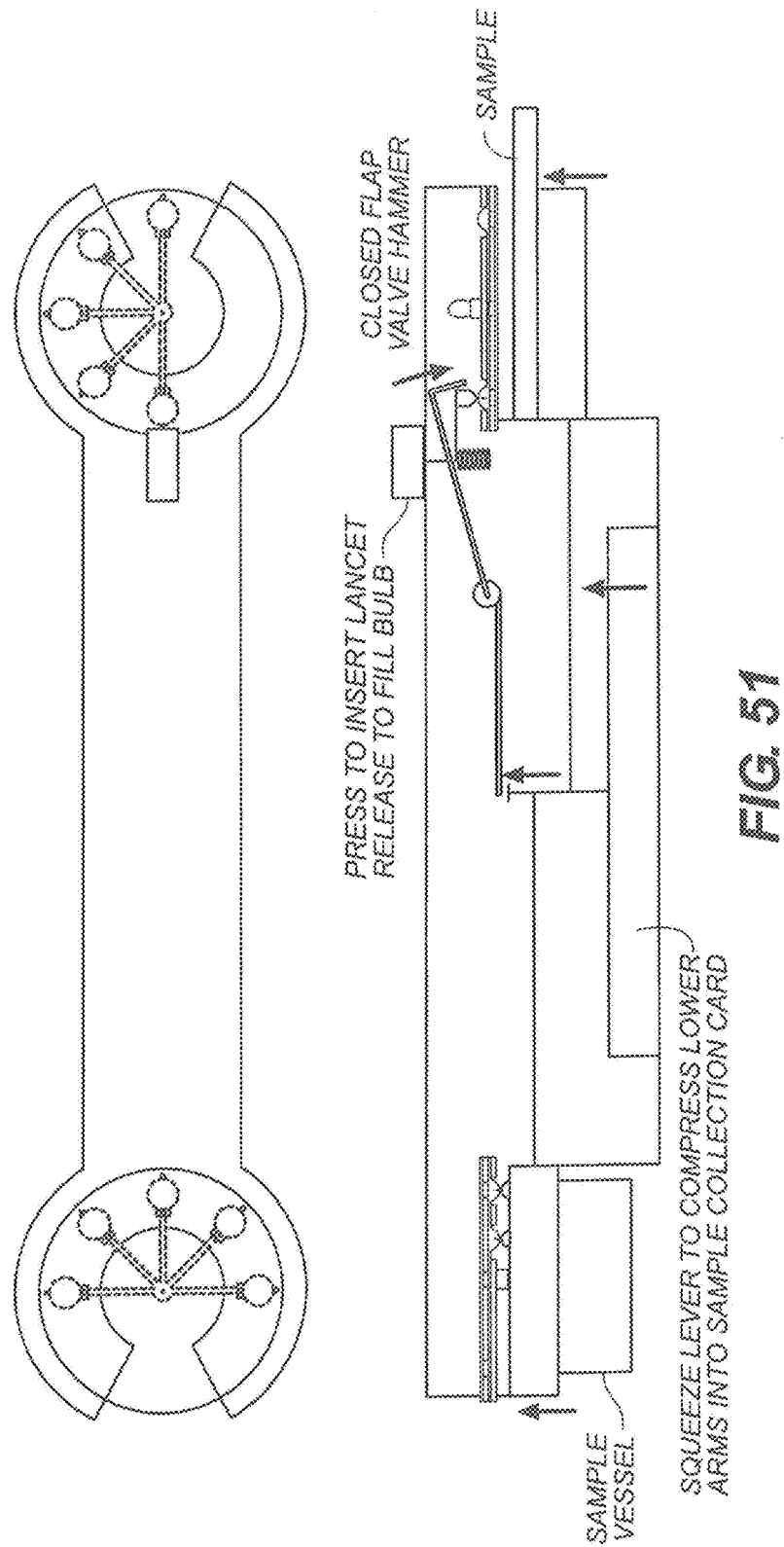
FIG. 51 shows a device for liquid sample collection.

Sample Input—Liquid (e.g. Blood) Collection:

The device shown in FIG. 51 utilizes a plastic bulb embedded with a lancet or other sharp puncturing device. When pressed, the bulb begins to deform creating pressure. A check valve on the bulb opens relieving the pressure as the bulb continues to collapse. Once the bulb as sufficiently deformed the embedded lancet pierces the thin film seal and subsequently the subject's skin/membrane. Because of the check valve, there is very little to no air in the bulb. This prevents an air pocket from forming just below the subject's skin/membrane allowing maximum fluid extraction. The bulb is then released allowing its natural tendency to return to its original shape. Doing so, the vacuum created draws in fluid from the puncture wound. The extracted volume is comparable to the displaced bulb volume (minor sealing leaks).

Dispensing the collected sample is done by simply affixing the bulb unit to the base where the check valve can be blocked. Pressing the bulb, again, creates pressure but because the check valve is blocked the sample is forced back through the original puncture hole and into a collection vessel.

The device comprises three parts; the base, the vacuum mechanism, and the plunger. The base comprises of a soft plastic ring/perimeter that acts like a gasket when in contact with a surface to insure good vacuum. One edge of the base will have a tab that is used to plug a check valve located in the vacuum mechanism. This tab prevents the check valve from opening when the device is in the load or closed position. The base may have a hinge that connects it to the vacuum mechanism or an adjacent device. The base may have a depressed region that acts to hold/contain the sample. Lastly, the floor of the base is a thin plastic film that can be easily punctured.

The vacuum mechanism comprises a soft plastic bulb that can return to its original shape after being compressed. An integrated check valve is formed at the edge of the bulb in order to prevent air pocket formation. Embedded at the apex of the bulb is a lancet that is used to puncture the subject. A thin plastic film (similar to the base) separates the base from the vacuum bulb. Above the bulb is a planar piece of plastic that is used to evenly compress the bulb. This piece is attached to the plunger. If required, a spring can be added to aid in the reformation of the bulb.

The plunger is simply a leverage tool to aid in operation. It can be modified to twist and lock in the depressed state to ensure complete compression.

A modification can be made to the device to prepare difficult mediums for analysis by replacing the lancet with a crushing or chopping edge. In this scenario, a sample such as an insect or piece of tissue is first placed in the recessed pocket in the base of the device. The vacuum mechanism is then attached to the base where the cutting/chopping blades are above the sample. Since a vacuum is not required for this operation, the seal in the vacuum mechanism is not required. The bulb is then pressed, lowering the blades onto the sample. Releasing the bulb allows the blades to rise for repeated cuts. When sufficient processing has been completed, the blades and sample can be pressed with enough force to break the bottom seal pushing the sample into another vessel.

Multiple bulbed configurations connected by a common channel can allow for grouped collection and analysis (FIG. 51). To do this, an additional check valve must be included between the bulb and the channel. This prevents air from being actuated into the channel when the bulb is pressed. To do this, an additional flap can be molded along with the bulb. This flab collapses into the channel when it is depressed preventing flow. The flap mechanism can easily be linked with the mechanism used to compress the bulb.

To combine and dispense the samples to another vessel, the apparatus is fitted into a tool similar to what is used to collect the sample (hammer/plunger compressor). The difference is that all bulbs are compressed while keeping the common channel flap valves open. The common channel leads to an output port that is mated to the collection vessel. This port is plugged until the fluid is dispensed. With the port opened, the collection vessel attached, all the bulbs are compressed at once. Because the channel flaps are left open, the fluid is pushed through the common channel and into the collection vessel. The pinholes under the collection bulbs are sealed by the tool's base when the hammer/plunger is compressed preventing leaks.

Multi-Sample Collection Tool—Sample Collection

Figure 52:
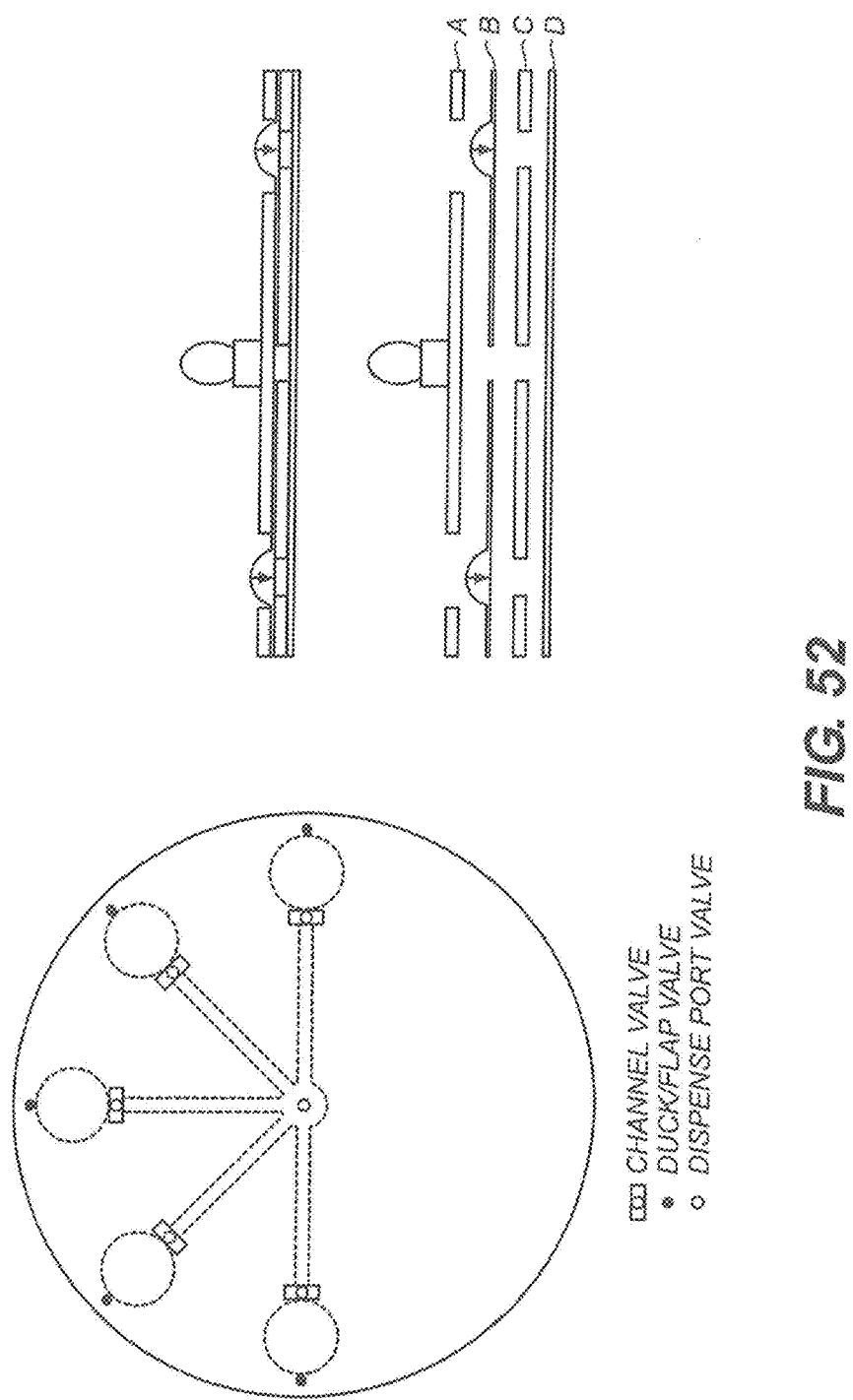
FIG. 52 illustrates an exemplary multi-sample collection disk.

As shown in FIG. 51 and FIG. 52, a multi-sample collection disk is inserted into the load side of the tool (button side) with the breakaway tab facing up. The disk is oriented so a collection bulb is beneath the hammer tab. The user inserts the sample (e.g. an animal ear) between the disk and the bottom plate and squeezes the bottom lever. This raises the bottom plate pinching the sample between it and the disk. Additionally, the compressed lever causes the channel flap valve hammer to pivot and lower onto the channel flap valve and consequently closing it. While still squeezing the lever, the top lancet button is pressed, compressing the bulb and piercing the sample with the embedded lancet. The button is released (spring assisted) and the bulb returns to its original form creating a vacuum and drawing in the sample. The lever is release, the channel flap valve hammer is raised, and the bottom plate is released from the sample. The disk is then rotated to the next available bulb for further collection.

Multi-Sample Collection Tool—Sample Transfer

The full, multi-sample collection disk is inserted into the transfer side of the tool with the breakaway tab facing down. The disk is aligned so that all the bulbs are under a compression hammer. The breakaway tab is removed creating an open port. An appropriate vessel is attached to the bottom plate (twist and lock). The lever is squeezed and the lower plate/vessel is raised and compressed against the disk bottom (the dispense port has a piercing edge allowing thin film seals to be broken). As the lower plate is forced against the disk, the hammers compress the bulbs and the duck/flap valves forcing the samples through the common channel and into the vessel. The lever is released and the disk is removed.

First Exemplary Sample Prep Lid (Solid)

Referring to FIG. 53, this method uses traditional capillary action to wet an absorbing solid with the sample (blood) before being transferred to a subsequent vessel. Like many blood analyzers, this apparatus contains a lancet for puncturing the skin which allows the sample to be absorbed into the material. The material can be anything that absorbs and retains a liquid sample (paper, cellulose matrix, etc). The material can be cut, pleated or woven in any manner to adjust the collected volume.

The device comprises four parts; the body, the sample ring, the lancet and the sample ring ejector. The body contains and braces the three components inside providing structural integrity. The sample ring is a small frame that the absorbent material is stretch around holding it in place. The sample ring is press fitted into the body but is intended to be removed with sufficient force. The lancet is spring loaded and connected to a handle/button. The lancet also has a unique key type piece that allows it to toggle between actuating the lancet and ejecting the sample ring. The sample ring ejector is a cylinder shaped piece that sits directly upon the sample ring. The lancet and its key piece, pass through the center. Under static and lancing conditions, the key piece slides inside the lock housing in the sample ring ejector. However, if the user pulls up and rotates the handle 90°, the key piece is removed from the lock housing and rests on top of the sample ring ejector. The user can then press down on the handle, forcing the sample ring ejector onto the sample ring, which causes the sample ring to dislodge. To maintain a sterile environment, each end of the housing can be sealed using a traditional heat film. The film is removed prior to lancing the subject.

An alternate design can be employed that does not use a key and lock method. Rather, the lancet spring is placed between the handle, now button, and the sample ring ejection piece (instead of the body). The spring still actuates when the button is pressed but is no longer used to eject the sample ring. To eject the sample ring, the sample ring ejector piece is connected to a separate button/lever through ports on the button plate.

This method can be modified to be used in multi sample collection disks. The tool would comprise of a sample clamp and two buttons to actuate the lancet and sample ring ejector. Additionally, an auto indexer and a vessel clamp can be added.

Explanation of Operation

For the first device, the user removes the protective film from the filter ring and places the sample ring side of the device onto the subject. The user then presses down on the handle to actuate the lancet and puncture the subject. As the sample leaks from the wound, the sample ring absorbs a fixed amount of liquid. The device is then placed over a collection vessel. The user pulls and rotates the handle 90° and then presses down forcefully causing the sample ring to eject into the vessel. The method is the same for the alternate device except for the sample ring ejection, which requires just a press of a button.

Second Exemplary Sample Prep Lid (Solid)

The cover of FIG. 54 is very similar to the previous design with the exception that the filter ring is not ejected into the sample prep chamber. Instead, the lid is reaffixed to the cartridge wherein the filter matrix is submerged into the chamber where it can be extracted. To maintain a sterile environment, the lid is stored separately and a plastic sleep is placed over the syringe/filter region (syringe cap).

Third Exemplary Sample Prep Lid (Solid)

Figure 55A:
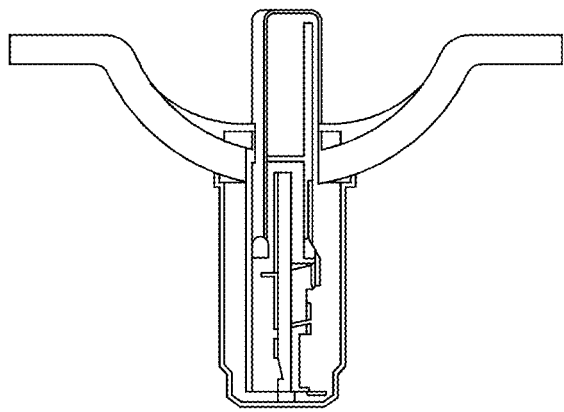
FIG. 55A, FIG. 55B and FIG. 55C are depictions of a lance-based system for collecting a liquid sample.
Figure 55B:
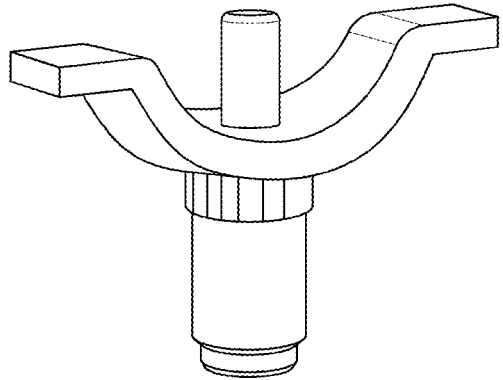
Figure 55C:
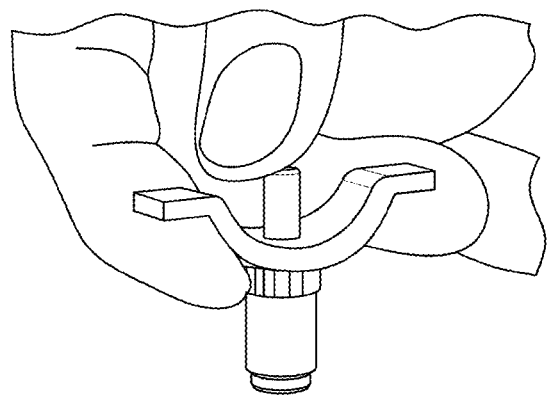

As shown in FIGS. 55A, 55B and 55C, this cover is very similar to the second exemplary sample preparation lid in terms of mechanical operation. The sample is still collected by the prick, absorb, and load method as outlined above. The first difference is the ergonomic design. The collection tool has been contoured to a more "syringe-like" form factor to simplify handling and use (FIGS. 49A, 49B and 49C). The second modification comes in the way of the mechanical actuation of the lancet. To ensure single use only, the actuation mechanism has been designed to actuate once. A cover with a build-in lance is shown in FIG. 56 that does not use a syringe-like form factor.

Multi Sample Collection (Solid) v.1B

As mentioned earlier, the solid sample prep v.1B apparatus can be modified to collect multiple samples. This is done by incorporating multiple syringe/ejector/sample ring modules into a single, disposable disk. The disk can be loaded into a collection tool similar to the design in FIG. 53. Like the tool in FIG. 53, the tool has a pair of clamps for stabilizing the sample. The lancet and the ring ejector are actuated via a button. The tool is also capable of indexing the disk to the next free position after collecting a sample. To collect/combine/remove the samples, a vessel is attached to the tool. As the tool indexes through available positions, the used regions rotate and eventually pass over the collection vessel where they can be ejected into the vessel. Once all the free regions have been used, the user continues to index/eject the disk until all the collected samples are loaded into the vessel. Once this occurs, the disk can be removed and stored/discarded. To ensure all the samples are collected, the user is unable to remove the disk until it indexes to the "complete/unload" position. For simplicity, the lancet, the ring ejector, and the index functions can be combined.

Sample Prep Lid (Liquid Concentrator)

In order to handle liquid samples that are larger than the 100 µL, a modification to the absorbent method can be used. Assuming the desired sample has been collected in a vacuum tube (i.e. blood) or some other vessel; the sample can be extracted and passed through a series of filters (10 µm and 0.2 µm). The final (smallest) filter acts a trap and contains the desired nucleic acids, spores, etc. And like the absorbent method, the trap filter can be ejected into an external collection vessel.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

What is claimed is:

1. A disposable cartridge for preparing an assay fluid, comprising:
    a cartridge body including (i) a cylindrical surface defining a fixed port and (ii) a syringe barrel defining a bore for receiving a moveable plunger, the fixed port disposed in fluid communication with the bore of the syringe barrel; and
    a rotor mounting to the cartridge body and including a surface slideably engaging the cylindrical surface of the cartridge body along a mating interface, the rotor including:
        a plurality of chambers each configured to facilitate at least one operation on the assay fluid, and
        a plurality of moveable ports disposed along the surface of the rotor and in fluid communication with at least one of the plurality of chambers;
    wherein the rotor is rotationally indexed about an axis parallel to the cylindrical surface such that the plurality of moveable ports are selectively aligned with the fixed port of the cartridge body.

2. The disposable cartridge of claim 1 wherein the moveable plunger is caused to translate within the bore to effect a flow of assay fluids from one chamber to another chamber to perform the at least one operation on the assay fluid.

3. The disposable cartridge of claim 1 wherein the cylindrical surface of the cartridge body includes at least one surface to close at least one of the plurality of moveable ports.

4. The disposable cartridge of claim 2 wherein the rotor further comprises a reaction chamber in fluid communication with one of the plurality of moveable ports.

5. The disposable cartridge of claim 4 wherein the at least one of the plurality of moveable ports is indexed to one of a plurality of radial positions each corresponding to alignment with the fixed port of the cartridge body and with a variety of other chambers of the rotor so that the assay fluid can be: (i) drawn into the syringe barrel, (ii) injected into one of the other chambers containing at least one processing compound, and (iii) injected into the reaction chamber for evaluating a test result associated with the assay fluid.

6. The disposable cartridge of claim 2 wherein the at least one of the plurality of moveable ports is indexed: (i) to a first radial position corresponding to alignment with the fixed port of the cartridge body, (ii) to another radial position corresponding to a reaction chamber of the cartridge body.

7. The disposable cartridge of claim 1, wherein the assay fluid travels through at least one chamber formed along a bottom panel of the rotor to provide a passageway for fluid flow from one chamber to another chamber.

8. The disposable cartridge of claim 4, wherein the assay fluid travels through chambers formed along a bottom panel of the rotor to provide a passageway for fluid flow from one chamber to the reaction chamber.

9. The disposable cartridge of claim 8, further comprising a signal processor disposed in the reaction chamber to detect the presence of a nucleic acid sequence.

10. The disposable cartridge of claim 2, wherein at least one of a plurality of ports is disposed at a predetermined height from the bottom panel of the rotor to prevent a backflow of assay fluid into one of the chambers.

11. The disposable cartridge of claim 2, further comprising a washing channel disposed along the bottom panel of the rotor, the washing channel including a first portion defining a first width dimension and a second portion defining a second width dimension which is greater than the first width, the second portion of the washing channel configured to concentrate magnetic nanoparticles.

12. The disposable cartridge of claim 1, wherein one of the rotor and the cartridge body includes an identifying marker from the group of: a barcode label and a Radio Frequency Identification (RFID) tag.

13. The disposable cartridge of claim 1, further comprising a chip including a biological probe.

14. The disposable cartridge of claim 1 wherein the chambers of the rotor have at least one open end defining an upper rim, and further comprising a thin film disposed over, and heat sealed to, the upper rim.

15. A method for preparing an assay fluid, including the steps of:
    configuring a cartridge body with: (i) a cylindrical surface defining a fixed port and (ii) a syringe barrel defining a bore for receiving a moveable plunger, the fixed port disposed in fluid communication with the bore of the syringe barrel;
    configuring a rotor for mounting to the cartridge body and including (i) a cylindrical surface for slideably engaging the cylindrical surface of the cartridge body along a mating interface, (ii) a plurality of chambers, and (iii) a plurality of movable ports disposed in the cylindrical surface and in fluid communications with the plurality of chambers;
    rotationally indexing the rotor about an axis parallel to the cylindrical surface of the cartridge body; and
    displacing the moveable plunger in the syringe barrel to cause the assay fluid to translate from the fixed port to one or more of the moveable ports, the assay fluid being moved from the chambers of the rotor to a reaction chamber where properties of the assay fluid are evaluated.

16. The method of claim 15 wherein a printed circuit board within the reaction chamber detects for the presence of a nucleic acid sequence.

17. The method of claim 15 comprising the steps of configuring the rotor with a washing channel along a bottom panel of the rotor such that the washing channel includes a first portion defining a first width dimension and a second portion defining a second width dimension which is greater than the first width dimension, and concentrating magnetic nanoparticles in the washing channel to prepare the assay fluid.

18. The method of claim 15, including the step of configuring the rotor with an identifying marker.

19. The method of claim 18 wherein the identifying marker is a barcode label.

20. The method of claim 18 wherein the identifying marker is a Radio Frequency Identification (RFID) tag.

* * * * *